US011013833B2

(12) United States Patent
Hasan

(10) Patent No.: US 11,013,833 B2
(45) Date of Patent: May 25, 2021

(54) COATINGS FOR MEDICAL DEVICES

(71) Applicant: ADVANCED ENDOVASCULAR THERAPEUTICS, Iowa City, IA (US)

(72) Inventor: David Hasan, Iowa City, IA (US)

(*) Notice: Subject to any disclaimer, the term of this patent is extended or adjusted under 35 U.S.C. 154(b) by 0 days.

(21) Appl. No.: 15/746,606

(22) PCT Filed: Jul. 18, 2016

(86) PCT No.: PCT/US2016/042825
§ 371 (c)(1),
(2) Date: Jan. 22, 2018

(87) PCT Pub. No.: WO2017/023527
PCT Pub. Date: Feb. 9, 2017

(65) Prior Publication Data
US 2018/0207325 A1    Jul. 26, 2018

Related U.S. Application Data

(60) Provisional application No. 62/213,979, filed on Sep. 3, 2015, provisional application No. 62/200,476, filed on Aug. 3, 2015.

(51) Int. Cl.
*A61F 2/90* (2013.01)
*A61L 31/08* (2006.01)
(Continued)

(52) U.S. Cl.
CPC ............ *A61L 31/088* (2013.01); *A61L 27/04* (2013.01); *A61L 27/306* (2013.01); *A61L 27/54* (2013.01); *A61L 31/022* (2013.01); *A61L 31/08* (2013.01); *A61L 31/16* (2013.01); *B82Y 5/00* (2013.01); *A61F 2/90* (2013.01);
(Continued)

(58) Field of Classification Search
CPC ...... A62L 31/088; A62L 31/022; A62L 31/08; A62L 31/16; A61L 27/04; A61L 27/306; A61L 27/54; A61L 2300/414; A61L 2300/42; A61L 2420/08; A61F 2/90; A61F 2210/0076; A61F 2240/001; A61F 2250/0067
See application file for complete search history.

(56) References Cited

U.S. PATENT DOCUMENTS 4,588,624 A    5/1986    Nygren et al.
5,052,777 A    10/1991   Ninnis et al.
(Continued)

FOREIGN PATENT DOCUMENTS

EP    2609941 A1    7/2013
WO    2005082277    9/2005
(Continued)

OTHER PUBLICATIONS

International Search Report and Written Opinion dated Oct. 4, 2016 for counterpart PCT Application No. PCT/US2016/42825.
(Continued)

*Primary Examiner* — Christopher D. Prone
*Assistant Examiner* — Tiffany P Shipmon
(74) *Attorney, Agent, or Firm* — Shuttleworth & Ingersoll, PLC; Jason R. Sytsma

(57) ABSTRACT

The present invention is directed to improved coatings and coating methods for medical devices.

9 Claims, 48 Drawing Sheets

(51) Int. Cl.
  *A61L 31/16* (2006.01)
  *A61L 31/02* (2006.01)
  *A61L 27/54* (2006.01)
  *B82Y 5/00* (2011.01)
  *A61L 27/04* (2006.01)
  *A61L 27/30* (2006.01)

(52) U.S. Cl.
  CPC . *A61F 2210/0076* (2013.01); *A61F 2240/001* (2013.01); *A61F 2250/0067* (2013.01); *A61L 2300/414* (2013.01); *A61L 2300/42* (2013.01); *A61L 2420/08* (2013.01)

(56) References Cited

U.S. PATENT DOCUMENTS

| | | | |
|---|---|---|---|
| 5,356,433 A | 10/1994 | Rowland et al. | |
| 5,384,194 A | 1/1995 | Deusser et al. | |
| 5,543,158 A | 8/1996 | Gref et al. | |
| 5,665,277 A | 9/1997 | Johnson et al. | |
| 5,919,570 A | 7/1999 | Hostettler et al. | |
| 6,290,721 B1 | 9/2001 | Heath | |
| 6,575,969 B1 | 6/2003 | Rittman et al. | |
| 6,612,012 B2 | 9/2003 | Mitelberg et al. | |
| 6,673,106 B2 | 1/2004 | Mitelberg et al. | |
| 6,818,013 B2 | 11/2004 | Mitelberg et al. | |
| 6,833,003 B2 | 12/2004 | Jones et al. | |
| 6,955,685 B2 | 10/2005 | Escamilla et al. | |
| 6,960,227 B2 | 11/2005 | Jones et al. | |
| 6,960,228 B2 | 11/2005 | Mitelberg et al. | |
| 7,001,422 B2 | 2/2006 | Escamilla et al. | |
| 7,037,330 B1 | 5/2006 | Rivelli et al. | |
| 7,037,331 B2 | 5/2006 | Mitelberg et al. | |
| 7,306,624 B2 | 12/2007 | Yodfat et al. | |
| 7,329,638 B2 | 2/2008 | Yang et al. | |
| 7,459,145 B2 | 12/2008 | Bao et al. | |
| 7,524,630 B2 | 4/2009 | Tan et al. | |
| 7,541,048 B2 | 6/2009 | DeWitt et al. | |
| 7,572,290 B2 | 8/2009 | Yodfat et al. | |
| 7,695,507 B2 | 4/2010 | Rivelli et al. | |
| 7,942,925 B2 | 5/2011 | Yodfat et al. | |
| 7,942,926 B2 | 5/2011 | Benco et al. | |
| 8,029,554 B2 | 10/2011 | Holman et al. | |
| 8,066,763 B2 | 11/2011 | Alt | |
| 8,357,179 B2 | 1/2013 | Grandfield et al. | |
| 8,419,787 B2 | 4/2013 | Yodfat et al. | |
| 8,431,149 B2 | 4/2013 | McMorrow et al. | |
| 8,506,615 B2 | 8/2013 | Leynov et al. | |
| 8,529,596 B2 | 9/2013 | Grandfield et al. | |
| 8,795,317 B2 | 8/2014 | Grandfield et al. | |
| 8,795,345 B2 | 8/2014 | Grandfield et al. | |
| 2004/0171280 A1 | 9/2004 | Conley et al. | |
| 2005/0089694 A1 | 4/2005 | Moffatt et al. | |
| 2005/0221072 A1* | 10/2005 | Dubrow | A61F 2/30767 428/292.1 |
| 2006/0204738 A1* | 9/2006 | Dubrow | A61F 13/02 428/292.1 |
| 2008/0044638 A1 | 2/2008 | Ratel | |
| 2009/0319035 A1* | 12/2009 | Terry | A61L 29/085 623/1.46 |
| 2011/0208023 A1* | 8/2011 | Goodall | A61L 2/00 600/310 |
| 2012/0034572 A1* | 2/2012 | Piascik | A61L 27/306 433/8 |
| 2012/0226093 A1 | 9/2012 | Creighton | |
| 2012/0232329 A1 | 9/2012 | Creighton | |
| 2012/0296149 A1 | 11/2012 | Creighton | |
| 2012/0310034 A1 | 12/2012 | Creighton et al. | |
| 2014/0135564 A1 | 5/2014 | Creighton | |
| 2015/0099919 A1 | 4/2015 | Creighton | |
| 2015/0107476 A1 | 4/2015 | Perez et al. | |

FOREIGN PATENT DOCUMENTS

| | | |
|---|---|---|
| WO | 2007133520 | 11/2007 |
| WO | 2011019401 | 2/2011 |
| WO | 2014169959 A1 | 10/2014 |
| WO | 2015107476 | 7/2015 |

OTHER PUBLICATIONS

Examination Report issued by the Canadian Intellectual Property Office dated Jan. 15, 2019 for counterpart Canadian Patent Application No. 2993,785.

Search Report issued by the European Intellectual Property Office dated Mar. 7, 2019 for counterpart European Patent Application No. 16833502.4.

Bastian, Ohler et al.: "DFT Simulations of Titanium Oxide Films on Titanium Metal", Journal of Physical Chemistry, vol. 117, No. 1, Dec. 24, 2012, pp. 358-367, ISSN: 1932-7447.

Gupta et al., Biomaterials, vol. 26, Issue 18, Jun. 2005, pp. 3995-4021.

* cited by examiner

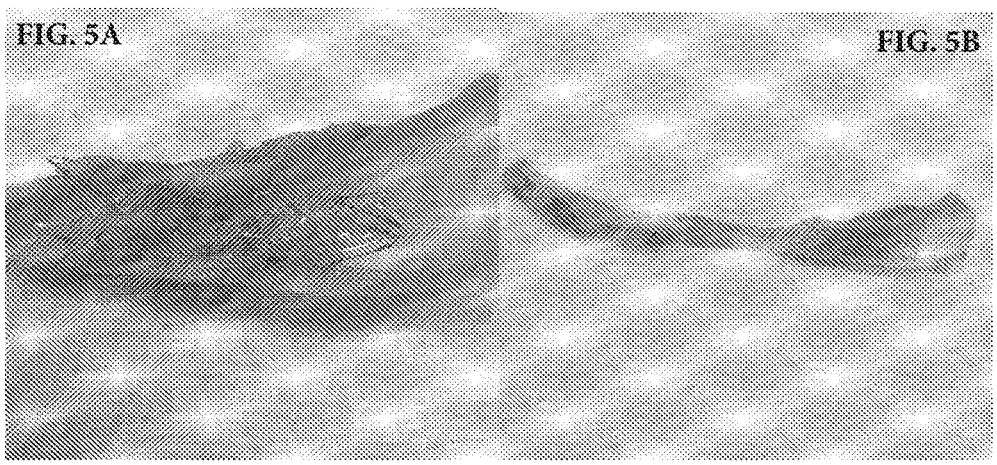
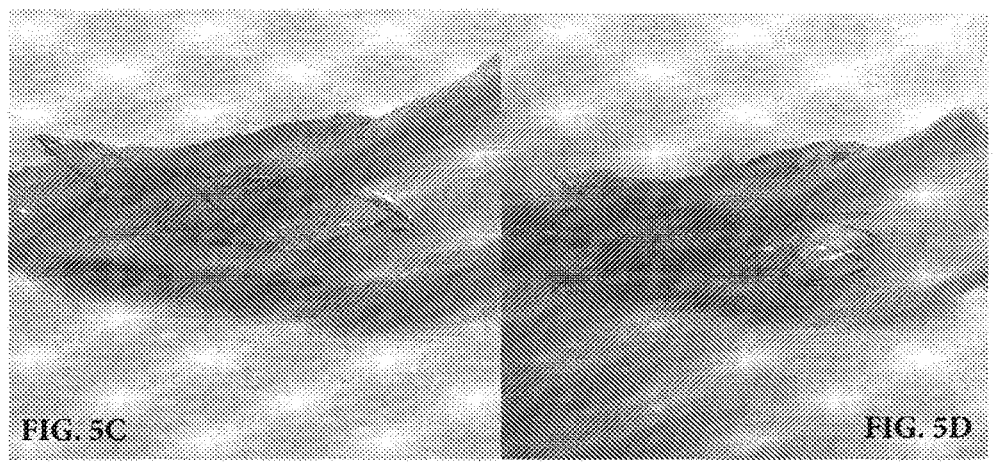
FIGS. 5A-5D

|  | Microplate Column | | |
|---|---|---|---|
| Time (hh:mm:ss) | 1 | 2 | ... |
| 0:00:00 | A1-0 | A2-0 | ... |
|  | B1-0 | B2-0 | ... |
|  | C1-0 | C2-0 | ... |
|  | D1-0 | D2-0 | ... |
|  | ... | ... | ... |
| 0:00:23 | A1-1 | A2-1 | ... |
|  | B1-1 | B2-1 | ... |
|  | C1-1 | C2-1 | ... |
|  | D1-1 | D2-1 | ... |
|  | ... | ... | ... |

FIG. 34

| Time (hh:mm:ss) | Microplate Well | | |
|---|---|---|---|
| | 1 | 2 | ... |
| 0:00:00 | A1-0 | A2-0 | ... |
| 0:00:23 | A1-1 | A2-1 | ... |
| 0:00:46 | A1-2 | A2-2 | ... |
| 0:01:09 | A1-3 | A2-3 | ... |
| 0:01:32 | ... | ... | ... |

COATINGS FOR MEDICAL DEVICES

CROSS-REFERENCE TO A RELATED APPLICATION

This application is the National Phase of International Application PCT/US2016/42825 filed Jul. 18, 2016 which designated the U.S. This application claims priority to U.S. Provisional Patent Application Ser. No. 62/200,476, entitled "Novel Coatings For Medical Devices," filed Aug. 3, 2015, and U.S. Provisional Patent Application Ser. No., 62/213,979, entitled "Novel Coatings For Medical Devices," filed Sep. 3, 2015, the disclosures of which are hereby incorporated by reference in their entirety.

BACKGROUND

Medical devices are widely used in modern healthcare industry. Numerous medical devices have been developed for implantation or inserting into human body, and as such, need to be biocompatible. It is often desirable that medical devices that are in constant contact with blood, such as stents, flow diverters, etc. should be haemocompatible and resist clot formation. Some of these devices are often composed in whole or in part of metallic alloys, which have the advantage of mechanical durability and stability in the body, but may need to be coated with a biocompatible or haemocompatible coating, for example in order to prevent the formation of clots, improve wettability, promote endothelialization, etc. Such coatings can contain active pharmaceutical ingredients (APIs) which elute from the coating after implantation to provide a desired therapeutic effect such as inhibit infection, reduce inflammation, inhibit or reduce clot formation, etc. However, the duration of the therapeutic effect of such APT eluting coatings is limited by the amount of API that can reasonably be incorporated into the coating, and the fact that the reservoir of such API is quickly depleted as it diffuses out of the coating. Further, the characteristics of the bio- or haemocompatible coating are circumscribed by various functional or material requirements of the device itself. Also, the components of some medical devices move or flex during operation or implantation, which necessitates a thin, compliant and/or durable coating which will not delaminate or break during use, or impede the operation of the device in use or during implantation. For example, stents are typically compressed to allow their insertion into a blood vessel, and require coatings that are robust and can resist delamination and fracturing as the stent is compressed prior to insertion, as well as upon expansion after insertion. Furthermore, the coating should not inhibit the expansion of the stent after insertion, or increase friction as the stent is guided through blood vessels. Coatings which crack and delaminate during or after insertion of the device (such as a stent) can release particles or flakes into the bloodstream, raising the risk of emboli which could adversely affect the health of the patient.

Inter alia, the methods and articles of the present invention provide improved coatings which are thin, compliant, bio- and/or haemocompatible, wettable, low friction, and only minimally, if at all, impair the mechanical properties of a medical device or component of a medical device. Further, the coatings of the present invention can provide for the attachment or binding of APIs to provide a long-lasting therapeutic effect, and improved efficacy of the device itself. The methods of the present invention also provide for coatings with improved adhesion, durability, and more effective coverage of the device surface.

SUMMARY

In various non-limiting embodiments, the present invention is directed to coated medical devices having at least one metal for at least a portion of which is coated with a metal oxide nanolayer. At least a portion of the metal oxide nanolayer is coated with covalently bonded organosilane groups substituted with at least one reactive organic substituent. Optionally, an active pharmaceutical agent is bonded to or complexed with at least a portion of the reactive organic substituents of the organosilane groups. In other embodiments, the present invention is directed to methods of coating the coated medical devices, and methods of implanting such coated medical devices in a mammal, for example a human.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale: in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIGS. 5A-5D are images showing an inventive coated stent removed from a pig carotid artery after an in-vivo study.

FIG. 34: An example of the organization of the raw fluorescent signal intensity data outputted from a Spectra-Max M5 fluorimeter.

FIG. 35: An example of the organization of the raw fluorescent signal intensity data required for data analysis.

DETAILED DESCRIPTION

Figure 1:
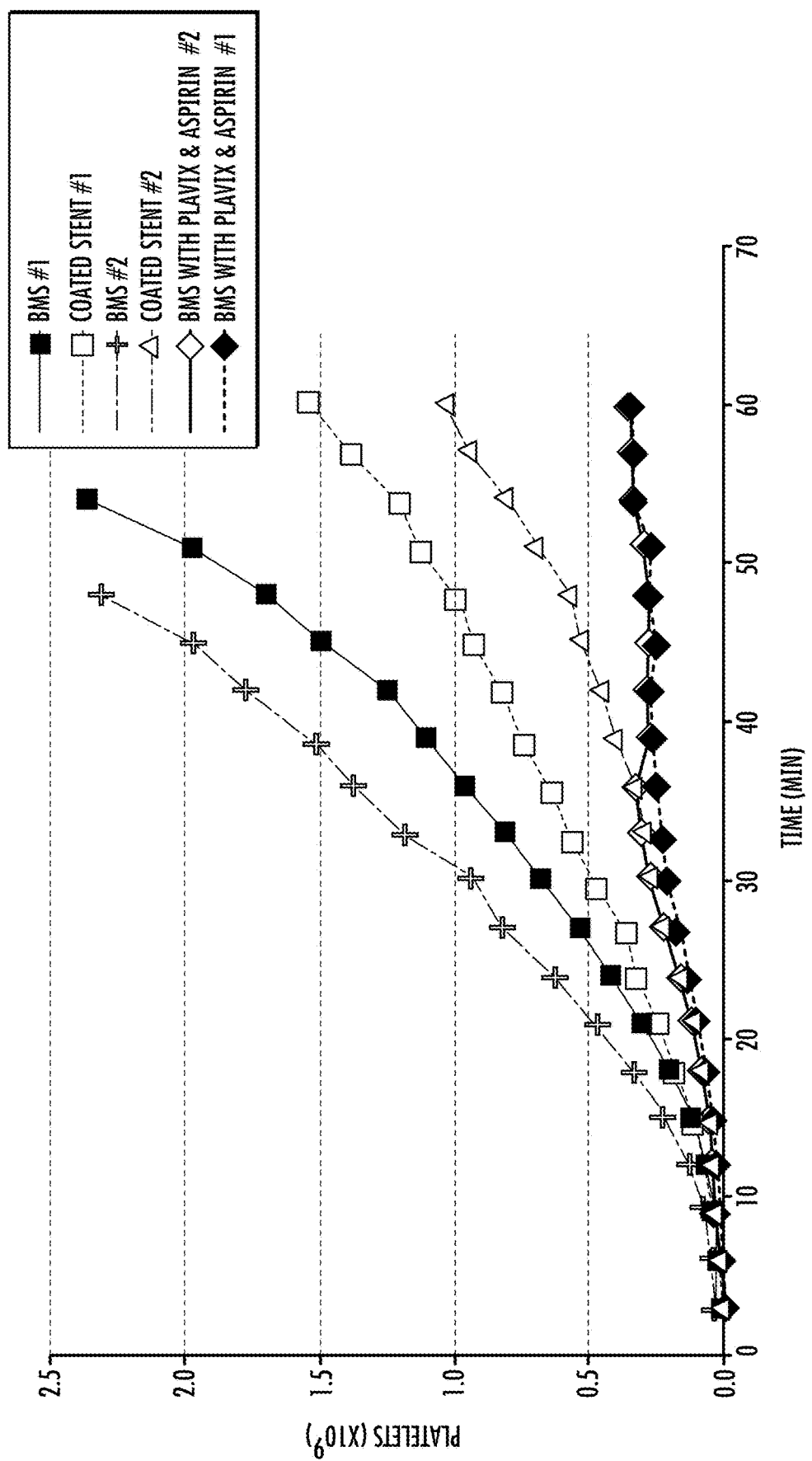
FIG. 1 is a plot of accumulated platelet counts from an ex-vivo study comparing the effectiveness of the inventive coated stents to those of bare metal stents (BMSs) and BMSs treated with the standard Plavix and Aspirin protocol.

In various embodiments, the coating technology of the present invention provides bio- and/or haemocompatible coatings which are capable of uniformly coating the surface of a medical device, particularly metallic surfaces, can help prevent the formulation of dots, improve wettability, and reduce the friction associated with insertion (e.g., during the insertion of stents or flow diverters in blood vessels) In some embodiments, the coatings and devices of the present invention can also provide an API on the surface of the coating which provides a useful therapeutic effect, such as promoting the endothelialization of an implantable medical device in blood-contacting environments. The coatings of the present invention are particularly useful for devices in contact with the circulatory system, and which require a haemocompatible surface. For example, the implantable medical devices of the present invention can include, but are not limited to stents, such as intra-cranial stents, carotid stents, cardiac stents, and peripheral vascular stents. Other devices which benefit from the coatings and methods of the present invention include vascular grafts, cardiac valves, and intravascular devices. In other embodiments, the coatings of the present invention can be applied to nanoparticles, for example nanoparticles comprising iron oxide, which can be infused into the bloodstream or other areas of the body, and manipulated magnetically. In the present disclosure, implantable stents are used as exemplary devices for demonstration purposes, but the inventive technology can be widely applicable to any and all implantable and/or blood-contacting medical devices. The following passages will describe embodiments of the coating technology of the present invention, beginning with the uncoated device, e.g, an implantable bare metal stent, followed by exemplary application of an exemplary metallic oxide ceramic coating that can be silanized with exemplary functional reactive groups to which desired exemplary APIs such as therapeutic drugs and/or pharmaceutical agents can be attached or adhered to produce a desired therapeutic effect (e.g., clot inhibition or prevention, epithelialization, etc.) after implantation.

Any suitable stent structure known in the art can be used to provide coated stems according the present invention. Exemplary implantable stents typically comprise biomedical grade metals and metallic alloys, including biomedical grades of titanium, iron, nickel magnesium, cobalt niobium, tantalum, and chromium (including any alloys thereof). Some of the more widely used alloying materials in commercially available stents include stainless steel, nickel-based super-elastic alloys, nonmagnetic alloys, and other alloys with similar mechanical and physical properties. An example of stainless steel alloy used is a medical grade 316L stainless steel. Some examples of nickel-based super-elastic alloys are chrome (nickel-chromium alloy), and nitinol (nickel-titanium alloy). Nitinol (typically nickel and titanium in equal ratio) is highly biocompatible, decreases the rate of corrosion, is very flexible and has excellent shape memory when heated to a certain temperature. Unfortunately, nitinol can be difficult to manufacture; as little as a 0.01% change in composition can drastically alter the temperature at which the alloy is transformed. In addition, the alloy must be created in a vacuum as the titanium component is highly reactive to oxygen. An example of nonmagnetic alloy is nickel-cobalt-chromium-molybdenum alloy (MP35N), which is particularly suitable if future medical diagnosis might involve the use of magnetism and magnetic imaging techniques.

Additional examples of super-elastic alloy materials include, for example, silver-cadmium, gold-cadmium, gold-copper-zinc, copper-aluminum-nickel, copper-gold-zinc, copper-zinc, copper-zinc-aluminum, copper-zinc-tin, copper-zinc-xenon, iron-beryllium, iron-platinum, indium-thallium, iron-manganese, nickel-titanium-vanadium, iron-nickel-titanium-cobalt, and copper-tin. Additional suitable stent materials and stent designs are described in the U.S. Pat. No. 6,290,721 (also referred to as the '721 patent), entitled "Tubular Medical Endoprostheses," the content of which is hereby incorporated herein by reference in its entirety for all purposes. These stents can have many shapes and form factors known in the art, and structural designs depending on their utility and functional purposes, and deploying environment. There are generally two broad classes of stent designs, including laser-cut, folded stents that can be opened up once placed inside a blood vessel such as an artery, and wire-mesh, compressed stents that can be expanded after placement at the targeted site. For example, suitable stents designs include those tor commercially available stents sold under the trade names Enterprise™ (Cordis), Neuroform EZ® (Stlyker), Neuroform 3® (Stryker), Silk (Balt), Pipeline (Covidien), FRED™ (MicroVention/ Terumo), Lvis (MicroVention/Terumo), Lvis Jr (MicroVention/Terumo), Surpass™ (Stryker), Bravo Cervical Asophageal (Ottomed), Trevo® XP Provue Retriever (Stryker), Solitaire™ AB (ev3 Inc.), and disclosed in, for example U.S. Pat. Nos. 6,612,012, 6,673,106, 6,818,013, 6,833,003, 6,955,685, 6,960,227, 6,960,228, 7,001,422, 7,037,331, 7,037,330, 7,695,507, 8,506,615, 6,575,969, 7,306,624, 7,572,290, 7,942,925, 8,419,787, 8,357,179, 8,529,596, 8,795,317, 8,795,345, each of which is incorporated by reference herein in its entirety.

Some of the more commonly used stents are built using a stainless steel material, the least-expensive stent material available. Unfortunately, stainless steel is not fully compatible with the human body and implantation usually is followed closely by restenosis and thrombosis. In addition, some stainless steel alloys can be magnetized, and thus can pose difficulties in diagnosis that involves a medical imaging technology that relies on magnetic resonance effect.

As discussed above, stents are typically folded or compressed (usually inside of a catheter) before implantation, inserted through a blood vessel until located in the desired implantation site, and subsequently expanded, any coating on the metal surface must not interfere with the compression and expansion of the device, and should not delaminate, crack, or otherwise damaged before, during, or after use. Cracking or delamination could result in partial exposure of the underlying surface of the stent, and thereby compromise the bio and/or haemocompatibility of the surface. Alternatively, or in addition, damage to the coating could increase the friction as the stent is inserted through the blood vessel, or otherwise make implantation more difficult or dangerous for the patient, and/or cause subsequent complications or adverse events for the patient after insertion. Finally, if particles of the coating break free in use, these particles could cause emboli or other obstructions in the circulatory system of the patient.

In addition, because intercranial stents must typically be inserted through the carotid artery, the long and relatively tortuous insertion path (compared to e.g. coronary stents) requires that the stent itself be small, very pliable (flexible), low profile and provide low friction during the insertion process. Conventional coatings typically add too much bulk, friction, and compromise the mechanical flexibility of the stent and therefore conventional intercranial stents are typically uncoated.

However, the coatings and methods of the present invention provide relatively thin, compliant stent coatings, in particular for intercranial stents, which have little, if any impact on the flexibility of the stent upon compression or expansion, resist cracking and delamination, and can reduce the friction or force required during insertion, as well as provide the option of incorporating APIs on the surface of the stent which persist (i.e., have a long lasting effect over a period of weeks or more) which can prevent or inhibit clot formation, and/or promote endothelialization.

An initial step in the process of the present invention is to coat the metal/metallic alloy surface of a stent with a metal oxide layer. In various embodiments, the metal/metal alloy surface can be pre-treated, cleaned, etched, or otherwise prepared for deposition of the metal oxide/ceramic coating prior to application of the metal oxide/ceramic coating. The coating step can passivate the toxic metal and alloy surface to create a bio- or haemocompatible surface, and as described herein, serve as a substrate for treatment with an organosilane.

In most embodiments, the metal oxide/ceramic coating is a nanolayer. Nanolayers are advantageous in that the thinness of the coating does not interfere with the mechanical performance characteristics of the medical device. For example, in wire-mesh type stent designs, during compression and expansion the wire elements of the mesh flex and slide against each other. A metal oxide/ceramic coating which is too thick can reduce the flexibility of the wire mesh itself, or can potentially adhere wires to each other so as to prevent or inhibit sliding and flexing. Accordingly, the nanolayer metal oxide/ceramic coatings of the present invention provide for improved performance (e.g. minimal or no change in the mechanical properties of the coated stent relative to the uncoated stent).

The term nanolayer refers to layers having a thickness of about 1 micron or less. The thickness of the metal oxide/ceramic nanolayer can range from about 1 nm to about 1 μn (e.g., about 1 nm, about 2 nm, about 3 nm, about 4 nm, about 5 nm, about 6 nm, about 7 nm, about 8 nm, about 9 nm, about 10 nm, about 15 nm, about 20 nm, about 25 nm, about 30 nm, about 35 nm, about 40 nm, about 45 nm, about 50 nm, about 55 nm, about 60 nm, about 65 nm, about 70 nm, about 75 nm, about 80 nm, about 85 nm, about 90 nm, about 95 nm, about 100 nm, about 150 nm, about 200 nm, about 250 nm, about 300 nm, about 350 nm, about 400 nm, about 450 nm, about 500 nm, about 550 nm, about 600 nm, about 650 nm, about 700 nm, about 750 nm, about 800 nm, about 850 nm, about 900 nm, about 950 nm, about 1000 nm), inclusive of all ranges and subranges therebetween.

In some embodiments, the coating of metal oxide/ceramic nanolayer covers essentially the entire surface of the medical device (e.g, stent). In other embodiments, the ceramic/metal oxide coating covers only a portion of the medical device (e.g, stent). For example the portion of the surface area of the device (e.g, stent) covered by the metal oxide/ceramic layer can range from about 50% to about 100% (e.g., about 50%, about 55%), about 60%, about 65%, about 70%, about 75%, about 80%, about 90%, about 95%, about 100%, inclusive of all ranges and subranges therebetween).

The metal oxide/ceramic coating can include any metal oxide or ceramic that provides hydroxyl (—OH) groups on its surface, capable of reacting with suitable organosilanes as described herein, can be deposited as a nanolayer as described herein, are bio- and/or haemocompatible, and have physical properties (e.g, sufficient adhesion to the metal surface, etc.) suitable for use with implantable devices. Suitable metal oxides/ceramics include, but are not limited to materials from the group consisting of silicon oxide, aluminum oxide, titanium oxide, iridium oxide, niobium oxide, tantalum oxide, ruthenium oxide, hafnium oxide, zirconium oxide, zinc oxide, tin oxide, strontium oxide, ytterbium oxide, $Zn_{1-x}Sn_xO_y$, ZTO (zinc-tin oxide), $SrTiO_3$, $SrCO_3$, and combinations thereof. For example, the metal oxide/ceramic coating can be a metal oxide containing only one type of metal atom such as silicon oxide, aluminum oxide, titanium oxide, etc., or can include a mixture of different types of metal atoms such as e.g ZTO, SrTiO3, etc. "Mixed" metal oxide compositions such as $Zn_{1-x}Sn_xO_y$ include a wide range of compositions in which x is a fraction ranging from 0 to 1 When x is 1 $Zn_{1-x}Sn_xO_y$ is $SnO_2$.(i.e., y=2); when x is 0, $Zn_{1-x}Sn_xO_y$ is ZnO (i.e., y=1). When x is between 0 and 1, y is a real number between 1 and 2 such that, overall, $Zn_{1-x}Sn_xO_y$ is formally electroneutral.

The metal oxide coating can also include physical mixtures of different metal oxides/ceramics. For example, the coating can include one or more chemically distinguishable layers in which different metal oxides/ceramics are sequentially deposited. Alternatively, the metal oxide/ceramic coating can include regions with different chemical compositions, e.g, provided by implanting, doping, reactively processing, or co-depositing different metal oxide/ceramic materials, or precursors of such materials.

The metal oxide/ceramic coating can be applied by any suitable technique which is compatible with the materials and structure of the medical device to be coated, provided that the coating method provides a nanolayer of the metal oxide/ceramic. Some of the available materials deposition techniques include physical vapor deposition (PVD) and chemical vapor deposition (CVD) techniques. PVD techniques, such as direct-current and radio-frequency magnetron sputtering techniques, and thermal evaporation and electron-beam evaporation techniques are some of the widely used deposition techniques that can be utilized to produce the coatings. These techniques usually rely on direct line-of-sight deposition of atoms physically ejected from a solid source of the metal and/or metal alloy onto a given medical device. As such, the film coatings produced via a physical vapor deposition technique are usually not conformal, can include voids, and sometimes possess a thickness variation across the coated surface. On the other hand, most of the chemical vapor deposition techniques offer conformal coating over an entire coated surface. CVD techniques rely on the chemical reaction process of depositing individual atoms or molecules via a vapor phase. Several flavors of the CVD techniques, such as plasma-enhanced CVD, low-pressure CVD, catalytic CVD, and atomic layer CVD are some of the widely used CVD techniques that can produce conformal coatings on a medical device. The atomic layer CVD, also known as atomic layer deposition (ALD), offers conformal pinhole-free coatings with a precise control of the coating thickness at the nanometer scale, which is perfectly suitable for producing thin uniform conformal coatings on medical devices.

Silanization, i.e., reacting a suitable organosilane with at least some of the hydroxyl groups on the surface of the metal oxide/ceramic coating can provide improved bio- or haemo-compatibility during or after implantation. Suitable organosilanes have at least one group capable of reacting with the surface hydroxyls of the metal oxide/ceramic coating. In various embodiments, such hydroxyl-reactive groups include, but are not limited to alkoxy and halo groups, for example, methoxy, ethoxy, propoxy, butoxy, etc. and chloro. After treatment, the alkoxy or halo groups are displaced, and the silane is bonded to the metal oxide nanolayer surface, e.g, covalently via silicon-oxygen bonds.

Suitable organosilanes, after reaction with the surface of the metal oxide/ceramic coating can optionally have at least one functional group capable of reacting with or binding (e.g., covalently, ionically, etc.) to a suitable API. For example, an API having amino functionality could react with a suitable carboxylic acid, epoxy, etc. functional organosilane; an API having carbon-carbon double bonds could react with an Si—H functional organosilane (via hydrosilation); carboxy or halo functional APIs could react with amino-functional organosilanes.

In various embodiments, suitable organosilanes have the general formula: $(X-R)_nSi-Y_{4-n}$ or $Y_3Si-R-Z-R-SiY_3$, wherein n is an integer from 1-3, each X is independently H, substituted or unsubstituted vinyl, halo, hydroxyl, substituted or unsubstituted amino, acryloxy, methacryloxy, —SH, or substituted or unsubstituted ureido, each R is independently alkyl, aryl or arylalkyl, Z is disulfide or tetrasulfide, and each Y is independently halo or a hydrolyzable group, such as an alkoxy group (e.g., methoxy, ethoxy, isopropoxy) or an acetoxy group that can react with various forms of hydroxyl groups present on the surface of the metal oxide/ceramic coating. Non-limiting examples of commercially available organosilanes that can be used for surface silanization according to the methods of the present are as followed: XIAMETER® OFS-6070 (methyltrimethoxysilane), Dow Corning® 1-6383 (methyltriethoxysilane), XIAMETER® OFS-6194 (dimethyldimethoxysilane), Dow Corning® Z-6265 (propyltrimethoxysilane), XIAMETER® OFS-2306 (isobutyltrimethoxysilane), XIAMETER® OFS-6124 (phenyltrimethoxysilane), XIAMETER® OFS-6341 (n-octyltriethoxysilane), Dow Corning® Z-6011 (aminopropyltriethoxysilane), XIAMETER® OFS-6020 (aminoethylaminopropyltrimethoxysilane), XIAMETER® OFS-6094 (aminoethylaminopropyltrimethoxysilane) (high purity), Dow Corning® Z-6137 (aminoethylaminopropylsiloxane oligomers) (aq), XTAMETER® OFS-6032 (vinylbenzylated aminoethylaminopropyltrimethoxysilane), XIAMETER® OFS-6224 (low Cl version of XIAMETER® OFS-6032 Silane), Dow Corning® Z-6028 (benzylatedaminoethylaminopropyltrimethoxysilane), XIAMETER® OFS-6030 (Y-methacryloxypropyltrimethoxysilane), XIAMETER® OFS-6040 (y-glycidoxypropyltrimethoxysilane), XIAMETER® OFS-6076 (y-chloropropyltrimethoxysilane), Dow Corning® Z-6376 (y-chloropropyltriethoxysilane), Dow Corning® Z-6300 (vinyltrimethoxysilane), XIAMETER®) OFS-6075 (vinyltriacetoxysilane), Dow Corning® Z-6910 (mercaptopropyltriethoxysilane), XIAMETER® OFS-6920 (bis-(triethoxysilylpropyl)-disulfide), XIAMETER® OFS-6940 (bis-(triethoxysilylpropyl)-tetrasulfide), Dow Corning® Z-6675 (y-ureidopropyltriethoxysilane), and IAMETER® OFS-6106 (epoxy silane modified melamine resin).

In some embodiments, the organosilane groups reacted onto the surface of the metal oxide/ceramic coating cover essentially the entire surface of the metal oxide/ceramic coating. In other embodiments, the organosilane groups reacted on the surface of the metal oxide/ceramic coating cover only a portion of the surface of the metal oxide/ceramic. Since the organosilane groups are presumed to attach to the metal oxide/ceramic surface by reacting with one or more surface hydroxyl groups, the percentage of surface coverage can be approximated by determining the percentage of reactive surface hydroxyl groups that have been reacted with the organosilane. In some cases, due to the surface topography or chemical composition of the surface, not all of the detectable surface hydroxyl groups may be available for reaction with the organosilane. The percentage of organosilane coverage can therefore be estimated by comparing the percentage of reactive surface hydroxyl groups present before and after silanization using appropriate surface analytical techniques, for example, via electron spectroscopies, such as Auger electron spectroscopy and X-ray photoelectron spectroscopy, via surface vibrational spectroscopies, such as high resolution electron energy loss spectroscopy and reflection-absorption infrared spectroscopy, and via surface sensitive desorption techniques, such as secondary ion mass spectrometry.

The silane may be applied to the metal oxide/ceramic coated surface using any suitable technique. For example, the metal oxide/ceramic surface (optionally pretreated e.g, by washing, acid etching, oxidation by e.g. ozone or peroxides, etc.) can be dipped, sprayed, roller coated, or otherwise contacted with a solution of the organosilane(s), as described herein, in a suitable solvent (e.g. a hydrocarbon or other inert solvent in which the organosilane is soluble) to effect reaction of the surface hydroxyl groups of the metal oxide/ceramic with the organosilane, whereby one or more of the hydroxyl-reactive functional groups of the organosilane react and bond the organosilane to the surface. Alternatively, the reaction of the organosilane with the surface hydroxyl groups could be effected by contacting the organosilane in the form of a organosilane liquid or vapor—i.e. without a solvent or inert gas diluent—with the metal oxide/ceramic surface. As needed, the surface can be heated or otherwise treated to accelerate the reaction rate and/or remove volatile byproducts from the reaction of the organosilane with the surface hydroxyls (e.g., alcohol if the organosilane is an alkoxy-substituted silane, or HCl if the organosilane is a chloro-substituted silane. After the reaction is complete, the residual unreacted organosilane and/or byproducts can be removed by washing the surface with a suitable solvent, by heating to remove volatile impurities, etc.

The percentage of surface coverage of the organosilane can range from about 50% to about 100% of the available hydroxyl group of the metal oxide/ceramic coating (e.g., about 50%, about 55%, about 60%, about 65%, about 70%, about 75%, about 80%, about 90%, about 95%, about 100%), inclusive of all ranges and subranges therebetween. Partial coverage of the surface can include embodiments in which only a selected region of the metal oxide/ceramic coating is silanized (and other portions are not silanized).

For example, 50% of the metal oxide/ceramic surface is 100% silanized. In alternative embodiments, partial coverage of the surface means partially silanizing the entire surface of the metal oxide/ceramic coating. For example, 100% of the metal oxide/ceramic surface is 50% silanized.

It may be desirable to incorporate different organosilanes, in varying percentages onto the surface of the metal oxide/ceramic surface. For example, the different organosilanes may have different reactive groups capable of bonding or complexing to different APIs such that a combination of different APIs can be incorporated in suitable amounts on the surface of the medical device, either distributed evenly over the silanized portion of the surface, or in specific regions or areas of the silanized surface, If two or more different organosilanes are incorporated onto the metal oxide/ceramic coated portions of the medical device, the organosilanes may be added sequentially, so that, e.g., a first organosilane is reacted at the desired percentage on the desired portions of the metal oxide/ceramic surface (suitably masked as needed to provide selective coverage), followed by reaction of a second organosilane, and so forth. Alternatively, a mixture of different organosilanes may be reacted with the desired portions of the metal oxide/ceramic coated surface of the device (e.g, stent).

Optionally, an active pharmaceutical agent (API) can be bonded to or complexed with the reactive organic groups that are attached to the organosilane bonded to the metal oxide nanolayer that is coated onto a metal surface of the medical device. Any suitable API that has a desirable therapeutic effect can be used. Some examples of suitable APIs include, but are not limited to the group consisting of hepatocyte growth factors, anti-thrombotic agents, for example thrombomodulin (TM) in all forms, activated protein C (aPC), heparin, antiplatelet agents, tissue plasiminogen activator (tPA), polyethylene glycol (PEG), Hirudin, etc., and combinations thereof.

In some embodiments, the API when present, is bonded or complexed directly to the reactive functional groups on the organosilane layer. In other embodiments, the API is attached to the organosilane by means of a poly functional linker. The polyfunctional linker is a compound with two or more reactive groups that can react with both the reactive functional groups of the organosilane layer, as well as the API, so that the API is "tethered" to the organosilane layer of the coating. Suitable polyfunctional linkers can include TCT (2, 4, 6-trichloro-1,3,5-triazine) as described herein, and other polyfunctional linkers such as polyacrylates, epichlorohydrin, polyepoxides, polyacrylates, etc. In some embodiments it is not desirable to include the API, and the organosilane, or the organosilane/polyfunctional linker layer may serve as a "passive" layer which provides improved surface characteristics for the coated devices, such as improved anti-thrombogenicity, improved lubricity to facility insertion into, e.g., an artery or vein of a subject, etc.

The metal oxide/ceramic layer(s) and organosilane coatings can be combined in any suitable manner. For example, in one embodiment an initially uncoated medical device (e.g stent) can be fully coated with metal oxide/ceramic nanolayer and the resulting metal oxide/ceramic nanolayer can be fully silanized. In other embodiments, the medical device (e.g. stent) can be fully coated with metal oxide nanolayer and the metal oxide nanolayer can be partially silanized (e.g., only a portion of the metal oxide/ceramic surface is silanized, or the entire metal oxide/ceramic coated surface is partially silanized). In still other embodiments, the medical device (e.g stent) can be partially coated with metal oxide/ceramic nanolayer and the metal oxide/ceramic nanolayer is completely silanized over the entire metal oxide/ceramic coated portion of the medical device (e.g stent). Yet in other embodiments, the medical device (e.g stent) can be partially coated with metal oxide/ceramic nanolayer and the metal oxide nanolayer is also partially silanized (e.g, only a portion of the metal oxide/ceramic surface is silanized, or the entire metal oxide/ceramic coated surface is partially silanized) In all of these embodiments, the coated and silanized medical device (e.g stent) can be either partially or fully functionalized with an API. In other embodiments, there is no API.

In another embodiment the coatings of the present invention, as described herein, can be applied to magnetic nanoparticles, for example comprising iron oxide in U.S. Pat. Nos. 5,543,158, 5,665,277, 7,052,777, 7,329,638, 7,459, 145, and 7,524,630, and Gupta et al., Biomaterials, Volume 26, Issue 18, June 2005, Pages 3995-4021, each of which is herein incorporated by reference in its entirety for all purposes. Specifically, the magnetic nanoparticles can be coated with a metal oxide/ceramic nanolayer as described herein (covering all or a portion of the nanoparticle), then silanized with a suitable organosilane as described herein having a functional group capable of reacting with or binding to a suitable API. Antithrombotic agents such as TM or tPA, or any of the APIs disclosed herein can then be bonded or complexed with the reactive organic groups on the silane moieties bonded to the metal oxide layer on the nanoparticles. Such API functionalized nanoparticles can then be used therapeutically by infusing them into the bloodstream of a patient having a clogged artery. The nanoparticles can then be induced, by means of a magnetic field, to flow towards the clot whereby the API on the surface of the nanoparticles is brought into close proximity to the clot, facilitating dissolution of the clot and restoration of blood flow. Suitable magnetic manipulation methods and devices are described, for example in U.S. Patent Publication Nos. 2012/0226093, 2012/0232329, 2012/0296149, 2012/0310034, 2014/0135564, and 2015/0099919, each of which is herein incorporated by reference in its entirety for all purposes.

The following passages describe some exemplary manufacturing processes pertinent to the present inventive coating technology.

Example 1: Atomic Layer Deposition Process

The following processing steps are carried out to execute an exemplary deposition method utilized for coating a thin metal oxide nanolayer on a medical device.
1. Follow proper gowning protocol to enter cleanroom
2. Once inside clean room, fill sonicator with deionized water.
3. Rinse four small glass Pyrex containers with acetone, as well as one small covered petri dish. Dry all completely with nitrogen gas.
4. Using forceps, place one device into one cleaned Pyrex glass container. Fill with enough acetone to fully submerge the device.
5. Place acetone-filled container with device into the sonicator and let the sonicator run for 3 minutes.
6. Remove container with device from sonicator. Using forceps remove device and place in an empty, clean Pyrex container. Fill the Pyrex container with enough isopropanol to fully submerge the device.
7. Place the isopropanol-filled container with device into the sonicator and let the Sonicator run for 3 minutes.

8. Remove the container with device from sonicator. Using forceps remove device and place in an empty, clean Pyrex container. Fill this Pyrex container with enough methanol to fully submerge the device.
9. Place the methanol-filled container with device into the sonicator and let the sonicator run for 3 minutes.
10. Remove the container with device from sonicator. Using forceps remove the device and place in an empty, clean Pyrex container. Fill this Pyrex container with enough deionized water to fully submerge the device.
11. Place the water-tilled container with device into the sonicator and let sonicator run for 3 minutes.
12. Remove the container with the device from sonicator. Using forceps remove device. Hold the device in the forceps under a nitrogen gas stream for at least 3 minutes, until the device is completely dry.
13. Place the dry device in a covered, clean petri dish and take it to an atomic layer deposition (ALD) apparatus.
14. Place the device in the ALD chamber using forceps and evacuate the chamber.
15. Once the chamber is evacuated, rw1 the ALD with plasma injection using a TMA (trimethyl-aluminum) precursor and keep the chamber at 25° C. throughout the deposition process. Repeat the deposition step 300 times (total run time of approximately 36 minutes).
16. Vent the ALD chamber to atmosphere pressure.
17. Once vented, remove the device with forceps from the ALD chamber and place the device in a clean, covered petri dish.

Example 2: Silanization Process

The following processing steps are from an exemplary silanization protocol to silanize the $Al_2O_3$ nanolayer coated on a medical device of Example 1.
1. Heat 60 mL of toluene (in an oil bath) to 65° C.
2. In a 20 mL without touching the $Al_2O_3$ coated device, transfer it into a vial. Fill the vial with enough acetone to completely submerge the device.
3. Fill a sonicator with water, and sonicate the acetone-filled vial containing the device for 3 minutes.
4. Decant the acetone from the vial, and fill with enough methanol to completely submerge the device.
5. Sonicate the methanol-filled vial containing the device for 3 minutes.
6. Decant the methanol from the vial, and fill with enough ethanol to completely submerge the device.
7. Sonicate the ethanol-filled vial containing the device for 3 minutes.
8. Decant the ethanol from the vial, and fill with enough deionized water to completely submerge the device.
9. Sonicate the water-filled vial with the device for 3 minutes.
10. Decant the deionized water from the vial and dry the device with clean, filtered nitrogen.
11. Add 0.6 mL of (3-aminopropyl)triethoxysilane (APTES) to the stirring, heated toluene along with the device (1% (v/v) solution). Allow the device to react in the heated solution for 20 minutes.
12. Decant the cooled solution and rinse the device with toluene 3 times, followed by acetone 3 times.
13. Turn on the nitrogen and use the glass pipet to dry the inside of the flask and the stent. Use tin foil to partially cover the flask opening while this is done so the stent does not bounce out. When the stent is dry it will start bouncing around the flask. Continue to blow nitrogen onto the stent for another 3 minutes from this point to ensure the stent is completely dry.
14. Note: in addition to doing this reaction with 1 stent, we've also done a batch reaction with 4 stents together. For the hatch reaction we added 3 mL of (3-aminopropyl) triethoxysilane (APTES) to the stirring toluene, so as to yield a 5% (v/v) solution.

Example 3: TCT-(or Cyanuric Chloride) Preactivation Process

The following steps are exemplary process steps during the preactivation.
1) Measure and dissolve cyanuric chloride in toluene to make a 0.27M solution in a Schlenk flask equipped with a stirbar.
2) Bubble nitrogen gas through this solution for at least 20 minutes before adding a stent, for example comprising any suitable medically acceptable metal or metal alloy (for example as disclosed herein).
3) Cap the Schlenk flask and maintain under flowing $N_2$. Partially submerge the flask in an oil bath at 70° C. and allow the stent to react for 4 hours and 15 minutes.
4) Lift the flask from the oil bath and allow to cool. Decant the solution and wash the stent 3 times with toluene and 3 times with methanol.
5) Dry the stent under a stream of nitrogen for at least 3 minutes until completely dry.
6) Process the treated stent in an ALD process as in Example 1.

Example 4: Protein Reaction Process

The following process steps are carried out to dispose a pharmaceutical agent on the surface of a medical device.
1) UV Sterilization: working under a sterile fume hood, turn on the UV lamp. Using sterile forceps set the stent horizontally in the hood and let sit for 10 minutes. Next use the forceps to set the stent vertically and let sit for 10 minutes.
2) Remove the vials of protein from the refrigerator. Each vial of TM (recombinant human thrombomodulin) contains 10 µg of lyophilized protein, contains only the extracellular domain of TM). Each vial of HGF (human recombinant hepatocyte growth factor), contains 25 µg of lyophilized protein (from human plasma).
3) Making the protein solutions: TM only solution: reconstitute 1 vial TM (10 µg) in 500 uL of PBS. Use vortexing unit to completely dissolve. TM+HGF solution: reconstitute 10 µg TM with 25 µg HGF in 500 µL of PBS. Use vortex device to completely dissolve.
4) Using forceps, place the stent in the appropriate protein solution
5) Close the vial tightly and place in a Styrofoam test tube holder. Tape vial in holder to ensure it remains upright and does not spill.
6) Place in refrigerator for 24 hours
7) Afterward move vial to a sterile hood. Working under the hood, remove the stent from the solution via sterile forceps and place under a nitrogen stream until completely dry (dry for at least 3 minutes).
8) Place back into cleaned test tube.

Example 5: Ex-vivo Platelet Accumulation Test

Figure 2:
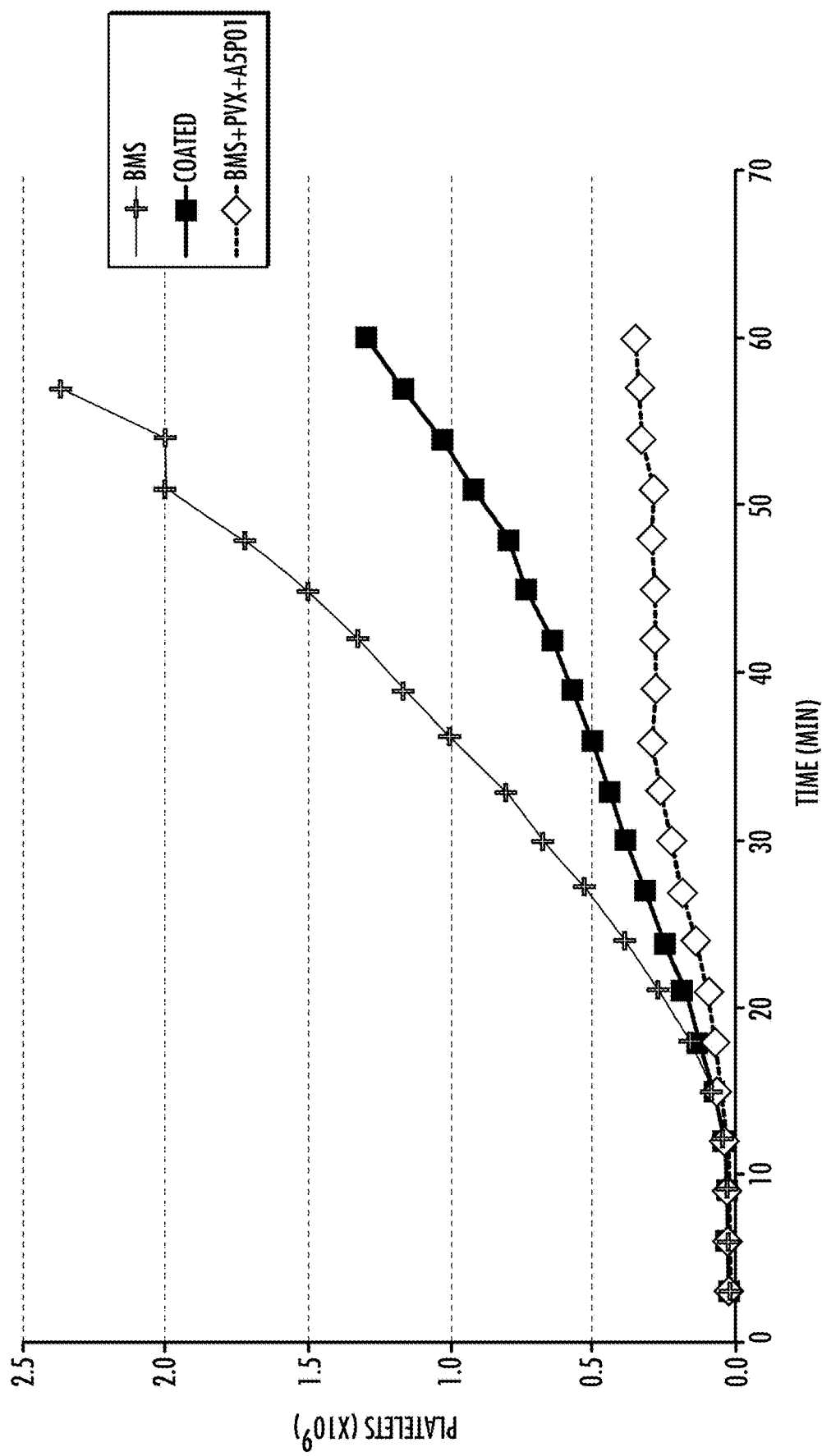
FIG. 2 is a plot of average ex-vivo platelet counts of the 3 different types of stents in the ex-vivo study of FIG. 1: Bare metal (uncoated) stent (BMS), inventive coated stents, bare metal stent with coadministered Plavix and aspirin.

Baboons were treated with radio-tagged platelets. Stents (uncoated, bare metal ("BMS"), inventive ("coated") or BMS with coadministration of Plavix and aspirin) were placed inside of a silicone shunt between the femoral artery and femoral vein. Both the BMS and coated were FRED™ stents made by MicroVention/Terumo. The coated stents were ALD coated with aluminum oxide and silanized with APTES as described above. The accumulation of platelets on the stent was monitored for 60 minutes by measuring the amount of labeled platelets entering and leaving the silicone shunt. The difference was attributed to accumulation of platelets on the stent. The accumulated labeled platelets versus time are plotted in FIG. 1 (FIG. 2 shows the average platelet accumulation). Both BMS samples showed complete occlusion and lack of blood flow before 60 minutes. The coated stents according to the present disclosure continued to show blood flow, and exhibited substantially less platelet accumulation. The BMS samples tested with concurrent Plavix and aspirin administration showed the lowest platelet accumulation. The platelet accumulation for the coated stent samples was statistically indistinguishable from the BMS+Plavix and aspirin samples. The platelet accumulation for the coated stent samples was statistically, significantly different from that of the BMS samples. This shows that the coated stents according to the present disclosure are substantially improved compared to conventional uncoated (BMS) stents, and are not statistically significantly different from conventional uncoated stents employing coadministration of Plavix and aspirin. Based on this data, the coated stents of the present disclosure can be used without Plavix coadministration, and would provide a significant (e.g. ~5-fold) drop in post implantation stroke incidence.

Example 6: In-vitro Thrombin Accumulation Test

Figure 3:
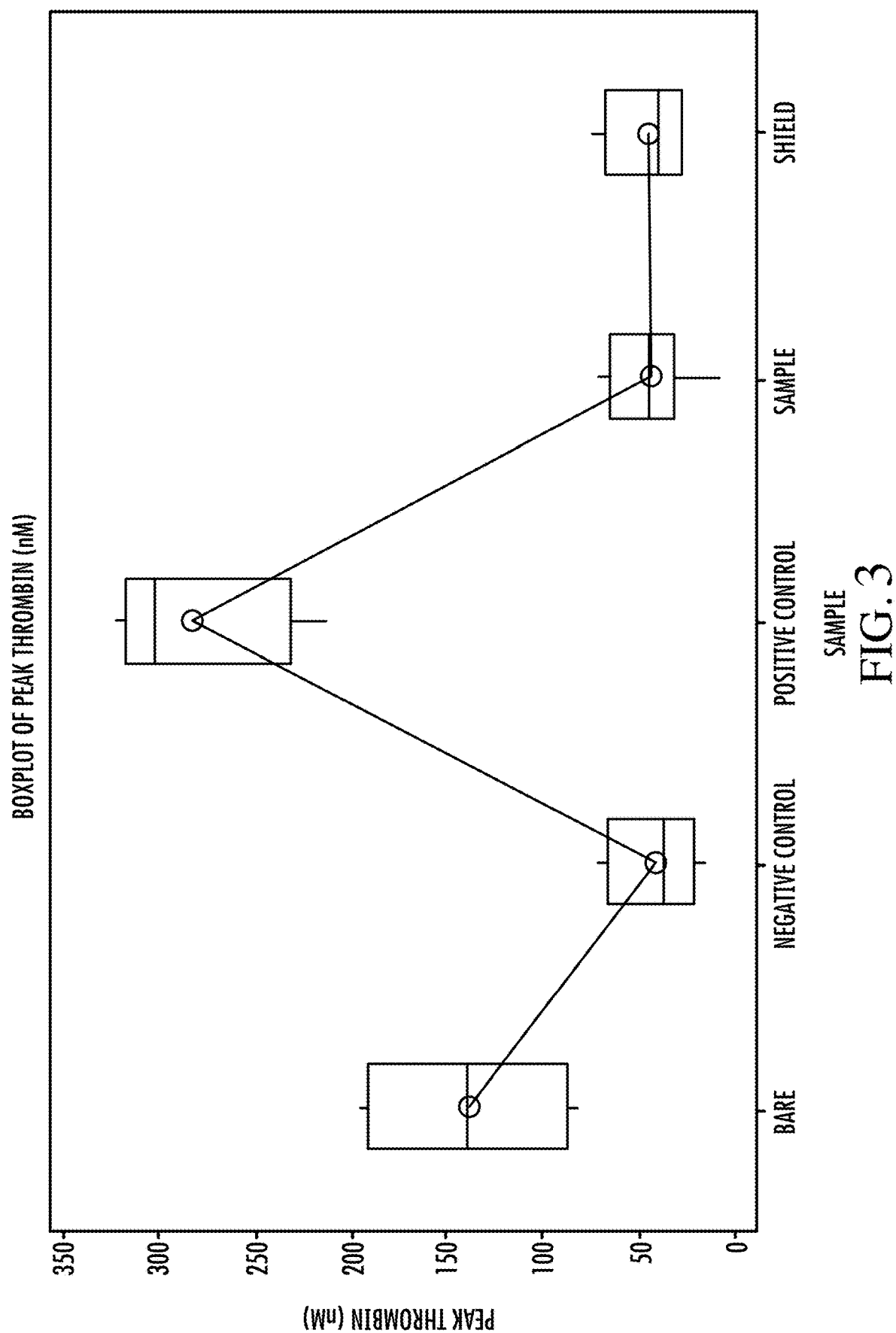
FIG. 3 is a box plot from an in-vitro study showing Peak Thrombin accumulations for 5 types of stent: BMS, negative control, coated stent, positive control, the inventive coated stent and commercially available vProtect Luminal Shield stent (Covidien/Medtronic).
Figure 4:
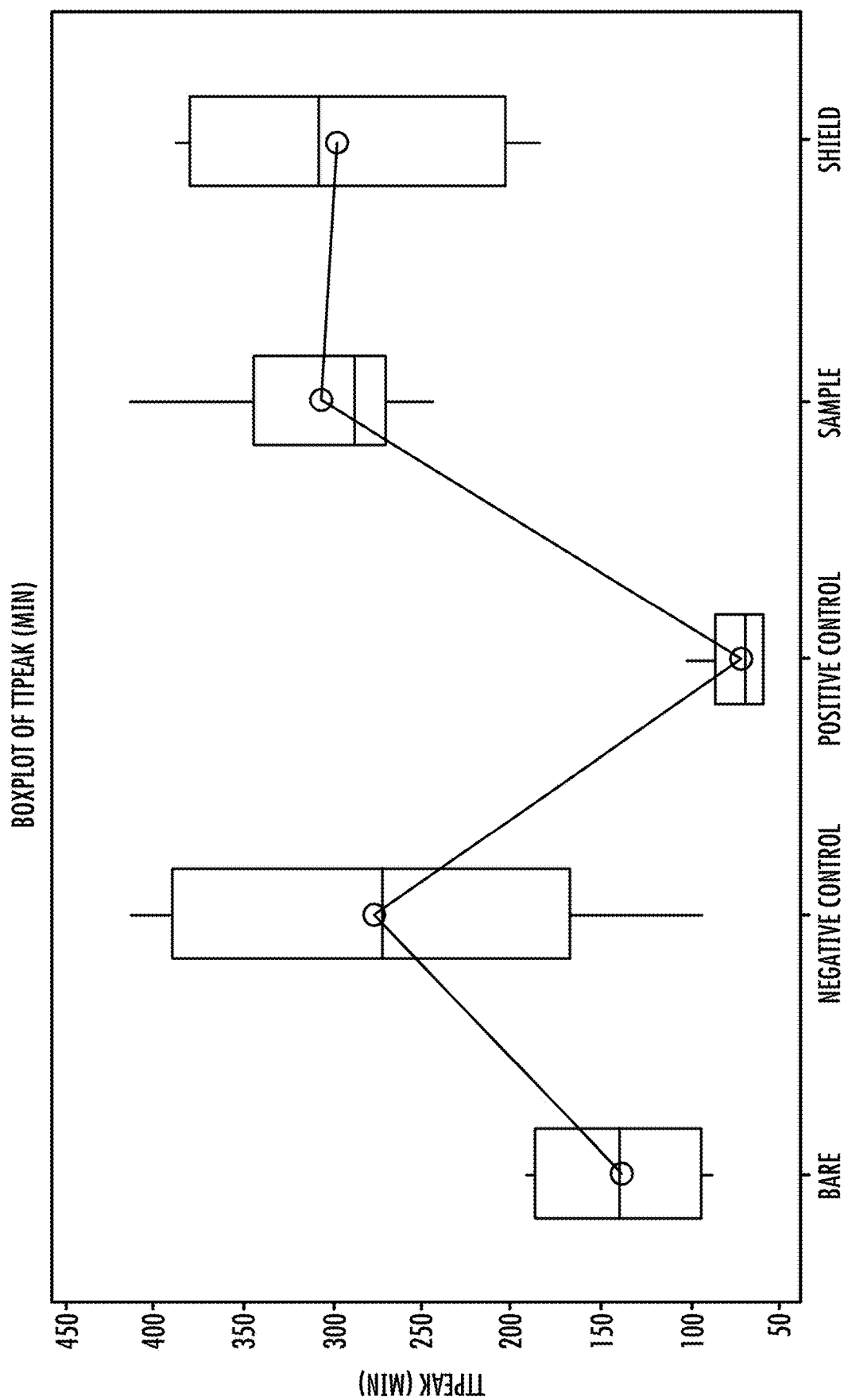
FIG. 4 is a box plot from an in-vitro study showing the time to Peak Thrombin accumulation (ttPeak times) for 5 types of stent: BMS, negative control coated stent, positive control, our inventive coated stent and commercially available vProtect Luminal Shield stent.

An in-vitro thrombogenicity study of various stent samples was conducted using millimeter-sized wells drilled in a glass substrate filled with blood. Each sample (e.g., a portion of a stent) was placed inside the well, and the time to peak amount, and peak amount of thrombin accumulated on the sample was measured using standard methods. FIGS. 3 and 4 are, respectively, box plots showing peak thrombin accumulation and time to peak thrombin accumulation for 5 types of samples: BMS ("bare"), negative control, positive control (glass), the inventive coated stent ("sample", aluminum oxide and APTES treated stent as described above) and commercially available vProtect Luminal Shield ("Shield") stents. The BMS sample (without any treatment or coating), shows an accumulation average Peak Thrombin of about 150 nM with a range from 90 nM to 190 nM. The negative control shows an average of about 30 nM with a range from 20 nM to 70 nM, whereas the positive control shows an average of about 270 nM with a range from 230 nM to 320 nM. The coated stents according to the present invention show an average of about 35 nM with a range from 30 nM to 65 nM. And lastly, a commercially available next generation stem, vProtect Luminal Shield, shows an accumulation average of about 30 nM with a range from 25 nM to 70 nM. From the side-by-side comparisons shown in FIG. 3, the coated stents perform as well as a next generation commercially available stents, with a substantially better peak thrombin performance compared to BMS. FIG. 4 (time to peak thrombin accumulation) shows that BMS samples take about 140 minutes to achieve peak thrombin accumulation (ttPeak) with a range of about 100 minutes to 190 minutes. The negative control shows a wide range of ttPeak with an average of about 270 minutes and a range of from about 170 minutes to about 390 minutes. The positive control shows an average of about 70 minutes with a narrow range of from about 60 minutes to 80 minutes. The inventive coated stent shows remarkably longer ttPeak times with an average of about 290 minutes and a very narrow and range of from about 280 minutes to about 340 minutes, whereas the conventional Shield stent a longer average ttPeak time of about 300 minutes, and a substantially larger range than the inventive coated stent. Thus, the claimed coated stents provide substantially lower peak thrombin levels, and substantially longer time to peak thrombin levels compared to convention bare metal stents. In addition, the inventive stents have a narrower range of time to peak thrombin compared to BMS, controls, and Shield stents, which demonstrates more reproducible anti-thrombotic performance.

Example 7: In-vivo Proof-of-Concept

An in-vivo experiment was conducted as a proof-of-concept type experiment using 10 stents that are coated using our invented coating technology. In this experiment, a coated stent was implanted in each of the carotid arteries of 5 pigs (i e, 2 stents per pig). The implanted stents were left in the pigs for 5 days and removed. 8 of the removed stents were found to be without thrombosis, which indicated that the inventive coating technology provides an 80% reduction of thrombosis. FIGS. 5A-5D are images showing coated stents removed from the pigs subsequent to the test.

Example 8: Baboon Study—Preliminary Results

As stated above, bare metal intracranial stents suffer an inherent lack of blood compatibility resulting in adverse events such as acute thrombosis/occlusion. As a result, patients are often treated with systemic dual anti-platelet therapy (clopidogrel/aspirin), which can lead to significant hemorrhagic complications. In this experiment, the coating technology described herein (and referred to in this example as AET-coated stents), was deposited on metallic intracranial stents, and is shown to be durable, withstands crimping and expansion, and has low thrombogenicity. In vitro tests indicate a 90% reduction in thrombus formation.

The study was conducted to perform haemocompatibility testing of the AET-coated stents alone and with aspirin compared to the clinical standard of bare metal control stents with and without dual anti-platelet therapy.

For the thrombosis experiments, an established baboon model of arterial-type thrombosis was used. The model has been used extensively to quantify the haemocompatibility of biomaterials, including stents, and the antithrombotic efficacy of various established and novel antithrombotic agents. The primary efficacy endpoint was the combined platelet and fibrin accumulation within the graft. The experiment was conducted to determine whether the AET-coated stent (with or without co-administered aspirin) will reduce the extent of platelet aggregation, the rate of platelet aggregation, and fibrin accumulation rate of thrombus propagation. Comparisons of haemocompatibility were made between pairs of stents including AET-coated stents, AET-coated stents with aspirin, bare metal stents without anti-platelet therapy, and bare metal stents with dual anti-platelet therapy.

The laboratory has extensive historical data on bare metal stents without antiplatelet therapy and will therefore use this to control for animal variability.

All baboon experimentation was performed at the OHSLJ West Campus on the grounds of the Oregon National Primate Research Center (ONPRC, Beaverton, Oreg.). The experiments were performed under the umbrella of the IACUC-approved OHSU protocol #0681, entitled "Thrombosis: Mechanisms and Interventions." Treatments and controls were tested in the same animals to limit variability and to act as internal controls.

The baboons (*Papio anubis*) used in these experiments were male, 3-5 years old and weigh 8-12 kg. The stents were provided by Stryker for coating (as discussed herein, the coating can be applied to any other stents and the present example is not intended to be limiting). They were sterilized using an E-Beam technique. The stents were deployed in silicone tubes provided by Stryker under sterile conditions. The inner diameter of the tubes was 4 mm. The Stryker stents used in these experiments were 4.2 mm×50 mm in their undeployed state (72 microwires).

Protocol Modification based on Stryker Stents and the Pre-Study Observations are as follows. Before initiating the experiments, several key features of the stents were noted that required protocol adaptation. The stents were noted to be "stretched" to about 80-85 mm (from an undeployed length of 50 mm) in the tubes and were substantially longer than stents tested in previous experiments. The ends of all stents were "crimped" and not fully opened, leaving gaps between the stent and the inner wall of the tubes (incomplete apposition).

Protocol Modifications based on Pre Study Observations are as follows. The experiment proceeded even though the length of these stents was not typical for this experiment For comparison, previous experiments were performed using stents 20 mm in length. Further, it was determined that the "crimped" ends of the stents should be positioned proximally in the shunt to give the longest entry length for the tubing. Because of these conditions, it was anticipated that the bare metal stents would more likely thrombose at an earlier time compared with previously studied shorter stents. Finally, due to the greater length of these stents (80-85 mm), it was determined to measure platelet accumulation in only the middle 60 mm of the stent as a means of standardizing data collection among all the stents used in this experiment.

The results of the experiment are listed as follows.

In experiment 8a, one bare metal stent first and then the AET-coated stent were evaluated. The bare metal stent occluded within 45 minutes, and it migrated distally due to the elevated intra shunt pressure. Because of this finding and to standardize testing conditions, a decision was made to stop all experiments at 45 minutes. The AET-coated stent was open and unobstructed throughout the 45-minute observation period without visible thrombus in the inner part of the stent.

In experiment 8b, one bare metal stent was tested first, followed by an AET coated stent. Both stents were open and 1 unobstructed at 45 minutes. Subsequently, the shunt occluded entirely and was '?rescued" with a heparin infusion over the following 48 hours. The study was then resumed 5 days later.

In experiment 8c, the baboon was loaded with aspirin 24 hours prior to initiating testing. In this experiment two AET-coated stents were tested in the presence of aspirin alone. The two stents were open and unobstructed at 45 minutes. Of note, the second AET-coated stent (labeled ASA2 in the subsequent graphs) was positioned with the crimped end distally, opposite to all of the other stents tested (proximal).

In experiment 8d, the baboon was loaded with Plavix immediately after the end of experiment 8c to allow 24 hours of Plavix in the baboon system, in addition to aspirin which was infused 24 hours prior to experiment 8c. Two BMS were tested under these conditions and they were patent at the end of 45 minutes.

Figure 6:
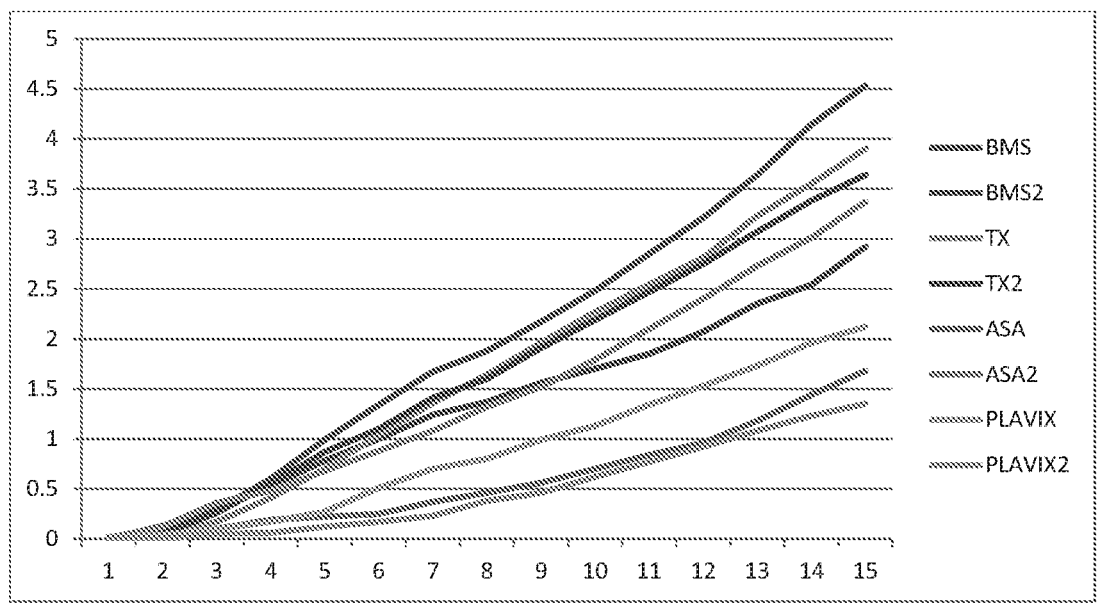
FIG. 6 is a plot of accumulated un-adjusted platelet counts from individual bare metal stent (BMS), AET coated stent (TX), AET coated stents+aspirin (ABA), and BMS+aspirin+Plavix (Plavix).
Figure 7:
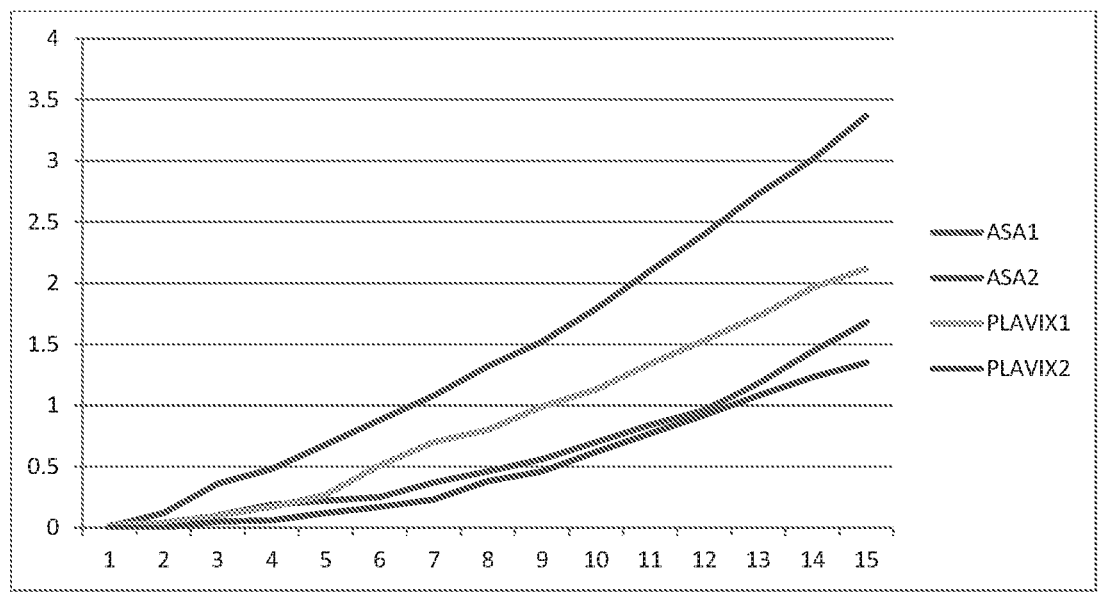
FIG. 7 is a plot of accumulated un-adjusted platelet counts from individual stents in both the coated+ASA vs. BMS+ASA+Plavix, where AET coated stents+aspirin is ASA and BMS+aspirin+Plavix is Plavix.

Analysis of platelet accumulation was conducted in the middle 60 mm (unadjusted) of the stents and the results of the platelet accumulation as a function of time were plotted as shown in FIG. 6. The 8 curves as shown in FIG. 6 are two of each from BMS: bare metal stent; TX: AET coated stent; ASA: AET coated stents+aspirin; and Plavix: BMS+aspirin+Plavix. FIG. 7 shows the results only of the medicated coated stents; two of ASA: AET coated stents+aspirin; and two of Plavix: BMS+aspirin+Plavix. The methodology of measuring platelet accumulation only in the middle 60 mm (described in methods above) precluded evaluating the platelet accumulation near the ends of the stents. The units for X axis is time in minutes and Y axis is the number of platelets in billions ($10^9$) in FIGS. 6-11.

Platelet accumulation is normalized for platelet count In reviewing the data, it was noted that the platelet counts were very low throughout the study compared to previous experiments. As a result, the data were normalized to a platelet count of 300, a technique used in the past when the circulating platelet counts throughout the study are this different compared to historical data. The following figures show the time platelet data 1) normalized to a count of 300 and 2) with and without the ASA2 data since this stem was positioned in an orientation opposite to all other stents in the study.

Figure 8:
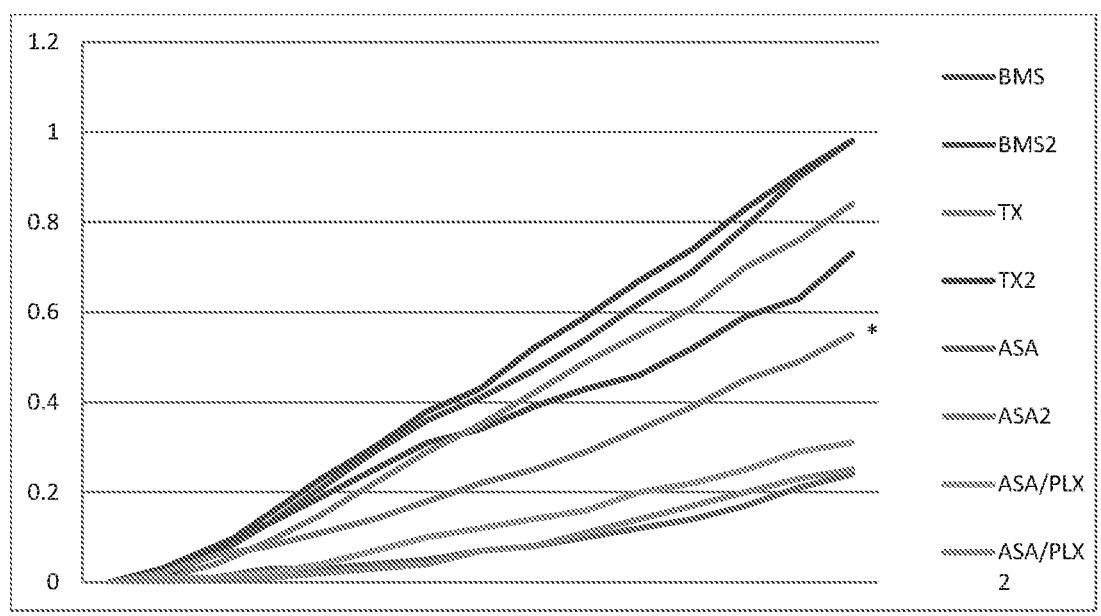
FIG. 8 is another plot of accumulated adjusted platelet counts from individual stents including BMS (bare metal stent), TX (AET-coated), ASA (AET-coated+aspirin), and ASA/PLX (bare metal stent+aspirin+Plavix), where* means the ASA2 stent is oriented in the opposite direction compared to the other stents.
Figure 9:
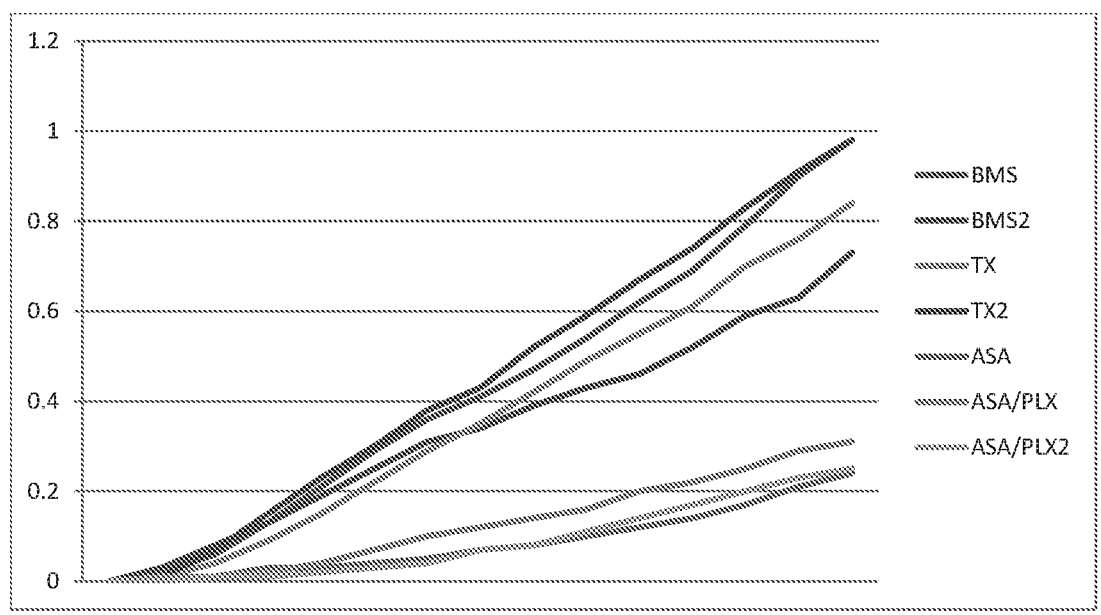
FIG. 9 is a plot of accumulated adjusted platelet counts from individual stents excluding ASA2, including BMS, TX, ASA and ASA/PLX (BMS: bare metal stent; TX: AET coated stent: ASA: AET coated stents+aspirin; ASA/PLX: BMS+aspirin+Plavix).
Figure 10:
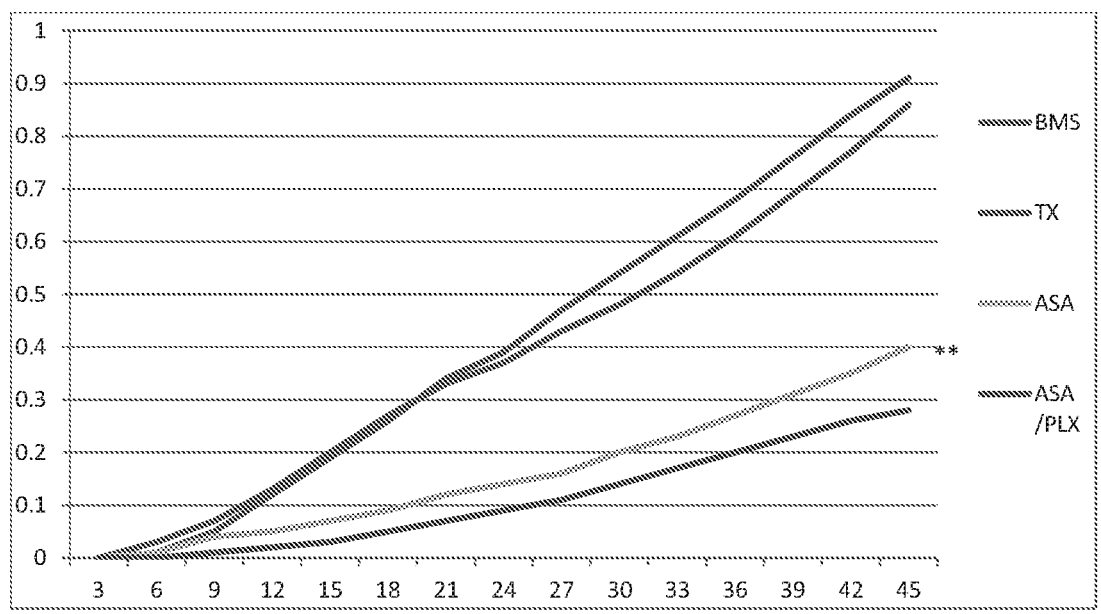
FIG. 10 is a plot showing the mean of two stents and includes ASA2 (adjusted platelets), including BMS, TX ASA, and ASA/PLX where** means the ASA2 stent is oriented in the opposite direction compared to the other stents (BMS: bare metal stent; TX: AET coated stent; ASA: AET coated stents+aspirin; ASA/PLX: BMS+aspirin+Plavix).
Figure 11A:
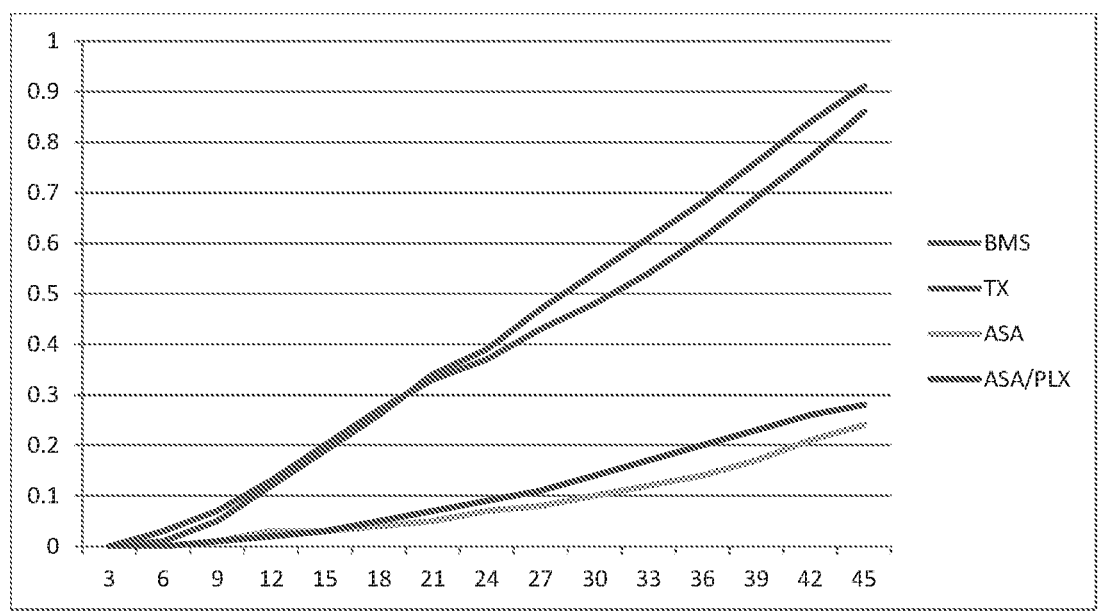
FIGS. 11A and 11B are a plot and a bar graph, respectively, showing the means for each pair of stents except the AET+ASA where only ASA1 is shown and ASA 2 (directionally opposite stent) was excluded (adjusted platelets). The plot also includes BMS, TX, ASA and ASA/PLX (BMS: bare metal stent; TX: AET coated stent; ASA: AET coated stents+aspirin; ASA/PLX: BMS+aspirin+Plavix)
Figure 11B:
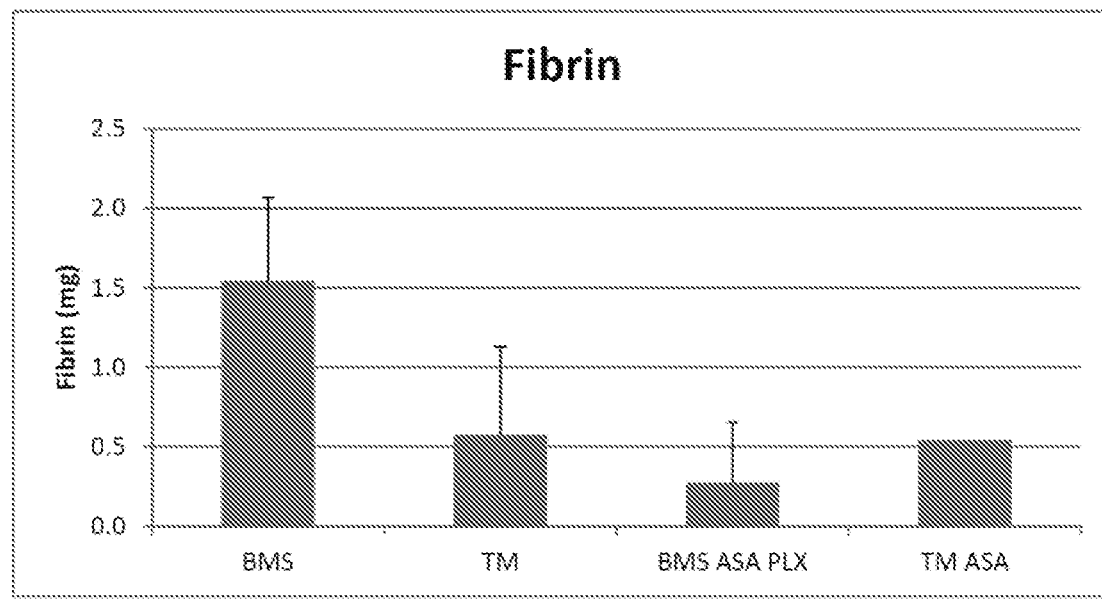

FIG. 8 shows all stents with platelets normalized to a count of 300. As plotted, the adjusted curves in FIG. 8 are as follows: BMS: bare metal stent; TX: AET coated stent; ASA: AET coated stents+aspirin; and ASA/PLX: BMS+aspirin+Plavix. Note that ASA2 stent was oriented in opposite direction, which may have affected the trend. In addition, FIG. 9 shows a plot of adjusted curves showing stents without those of ASA2: BMS.bare metal stent; TX: AET coated stent; ASA: AET coated stents+aspirin: and ASA/PLX: BMS+aspirin+Plavix. Normalizing the platelet counts reveals that the second AET which was coated stent studied with aspirin was positioned opposite to all other stents, with the crimped end distal, not proximal.

The analysis of the results is as follows. The substantially longer stents used in this experiment (80-85 mm vs. 20 mm) likely caused thrombosis as a consequence of the accumulation of platelets and thrombus despite the co-administration of aspirin and Plavix, and therefore appear to have overcame the beneficial effects of the AET-coating. Prior experiments using 20 mm stents showed that platelet and thrombus accumulation plateaued at an early stage and maintained a horizontal line, as shown in FIG. 1. This plateau was not seen in the experiments 8a-8d, which suggests ongoing accumulation of thrombus.

In addition to longer stents, the "crimped" ends of the stents also appeared to contribute to accelerated stent thrombosis due to incomplete wall apposition. In this experiment, AET-coated stents functioned the same as BMS, which suggests that in long stents, especially when crimped, the effects of thrombus accumulation overcomes the improved properties of the AET-coating, as shown in FIG. 6. The AET-coated stent in the presence of aspirin (ASA1) functioned as well as BMS with dual anti-platelets (aspirin and Plavix), shown in FIG. 7. The ASA2 stent was an outlier, probably because the crimped end was placed distal, not proximal and accumulation of thrombus at the early stage of the experiment FIGS. 8-11 show the curves and bar graph in FIGS. 6 and 7 after platelet counts are adjusted.

Example 9: Haemocompatible and Antithrombotic Coatings for Stents and Diverters

Figure 12:
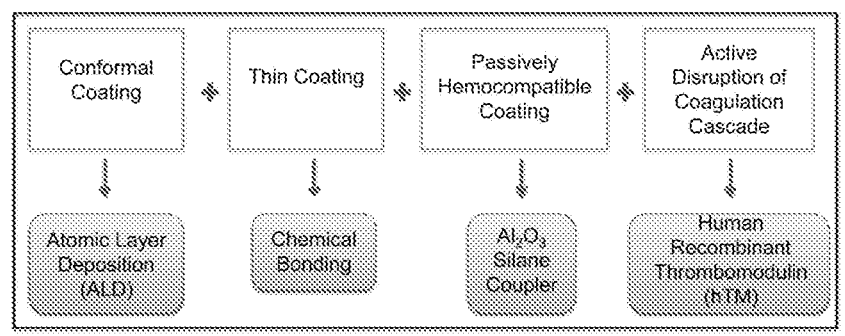
FIG. 12: Design attributes of the inventive coating chemistry and deposition technique for neurovascular devices.

In this study, the following preliminary work was done to assess each of the coating design attributes given in FIG. 12.

In specific, the work was done to assess the conformity of the inventive coating using the analytical chemistry techniques of Scanning Electron Microscopy (SEM) and X-ray Photoelectron Spectroscopy (XPS). To characterize coating layer thicknesses, both XPS and spectroscopic ellipsometry, a non-contacting thin film measurement technique, were used. To assess the haemocompatible and antithrombotic functionality of the inventive coating the Calibrated Automated Thrombogram (CAT) Assay and the Protein C Activation Assay, both in-vitro assays, were used. To assess device stiffness and device-associated friction on the delivery microcatheter two independent mechanical test methodologies were developed. Additionally a discussion of the coating chemistry and deposition technique, briefly outlined in FIG. 13, is given in what follows.

Coating Chemistry and Deposition Technique

Figure 13:
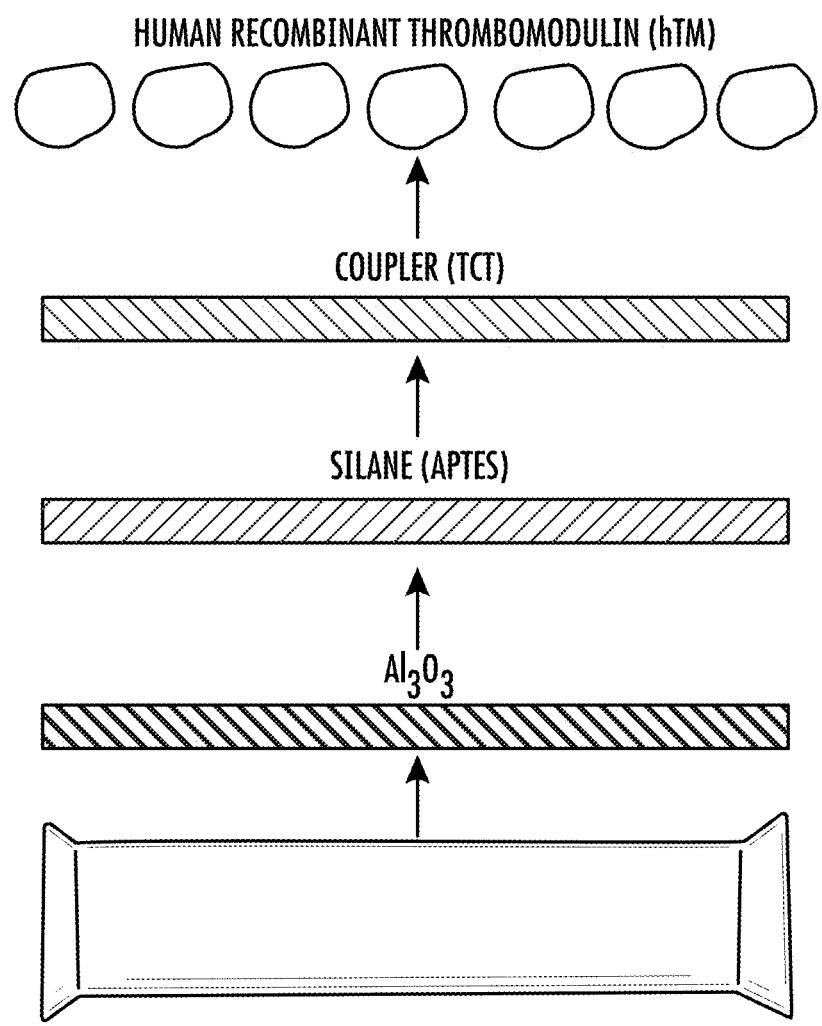
FIG. 13: Schematic of the inventive haemocompatible and antithrombotic coating chemistry for neurovascular devices, according to an embodiment.

The deposition method for the inventive coating is a layer-by-layer technique and is succinctly outlined in FIG. 13. As shown in FIG. 13, the aluminum oxide is initially deposited on the neurovascular stent or flow diverter surface. This layer provides a uniform oxide surface, on which each subsequent layer is deposited. This is especially important in the case of flow diverting devices, which can be composed of wires made from two or more metal alloys. With such a device, coating deposition would require functionalization of each wire type separately—a challenge. Deposition of the aluminum oxide layer therefore provides a uniform oxide surface that can be functionalized in a consistent manner, regardless of the material composition of the underlying device.

As the first layer in the inventive multi-layer coating, aluminum oxide is the foundation on which each subsequent layer is deposited. As a result, it is vital that it is deposited in a thin and conformal manner relative to the underlying stent or diverter wires. If this layer is too thick, or else non-conformal, addition of each subsequent layer will only increase coating thickness or the degree of non-conformality, leading to increased device stiffness. Such a change in device mechanics would compromise the ability of (or in the worst case prevent) the device from being loaded into its deployment catheter, promoting cracking and chipping of the deposited coating in the process.

To avoid these problems, atomic layer deposition (ALD) is used to deposit the aluminum oxide layer. ALD is a technique for depositing thin, conformal films on 2D and 3D substrate geometries and was originally developed in the 1970's for manufacturing thin film electroluminescent displays. Since then it has been used extensively in the semiconductor industry as a means to fabricate integrated circuits. ALD is able to achieve highly conformal film deposition due to the fact that it utilizes two surface reactions to deposit a binary compound film; in other words, film growth occurs by sequentially exposing the substrate to two individual gaseous precursors, and purging the ALD chamber between exposure steps to remove active source gas. The sequential precursor exposure steps are self-limiting surface reactions.

The ALD process begins by placing a substrate in the ALD chamber and evacuating it. Next the chamber is pumped with the first gaseous precursor, trimethylaluminum (TMA). TMA reacts with the substrate according to the scheme shown in Equation 1:

$$OH^* + Al(CH_3)_3 \rightarrow AOAl(CH_3)_2^* + CH_4 \quad (1)$$

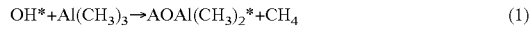

In Equation 1, the asterisks denote the surface species, also note that metallic surfaces are naturally oxidized by hydroxyl groups due to lattice imperfection, as well as the natural surface adsorption of water by van der Waals forces. Next argon gas is used to purge the chamber of TMA and reaction by-products; oxygen plasma is then pumped in. The oxygen plasma reacts with the substrate in a combustion-like process yielding primarily —OH groups on the substrate surface, but also a very small concentration of surface carbonates, as confirmed by in-situ Attenuated Total Reflection Fourier Transform Infrared Spectroscopy (ATR-FTIR). The carbonates are short-term reaction intermediates and decompose according to the series reaction when exposed to prolonged oxygen plasma, as shown in Equation 2.

$$CH_3 \rightarrow carbonates \rightarrow Al_2O_3 \quad (2)$$

Pseudo first-order kinetics govern how the surface methyl ligands, shown in Equation 1, combust to yield surface —OH groups and $Al_2O_3$ (forming CO, $CO_2$, and $H_2O$ reaction products). Additionally a second reaction mechanism is possible during the oxygen plasma exposure step and is shown in Equation 3. This mechanism is initiated upon formation of $H_2O$ 2 in a chamber, which is a product of combustion:

$$AlCH_3^* + H_2O \rightarrow AlOH^* + CH_4 \quad (3)$$

In Equation 3, the asterisks denote the surface species. Note that this secondary reaction can only occur when —$CH_3$ groups are present on the surface and therefore becomes insignificant when most —$CH_3$ groups are reacted away by the combustion-driven reaction mechanism. It should be noted that a third reaction mechanism is possible during the oxygen plasma exposure step and is one that generates higher order hydrocarbon ($C_2H_x$) reaction products, which have been observed by mass spectroscopy. Furthermore, first principles density functional theory calculations suggest that this mechanism is favored over the combustion reaction mechanism. Together, these three reaction mechanisms are thought to explain the primary surface reactions that occur in the oxygen plasma exposure step; nevertheless, additional reaction mechanisms cannot be excluded. Next the chamber is purged of oxygen plasma, again by argon gas, and the ALD cycle is complete. Following this the chamber is again pumped with TMA and the entire cycle is repeated.

The use of oxygen plasma in the ALD cycle is characteristic of plasma enhanced-ALD (PE-ALD), which enables lower chamber temperatures to be used, relative to and distinct from thermal ALD processes. This is because oxygen plasma is a more reactive oxidant than $H_2O$, or the oxidant used in thermal ALD processes; thus, the surface reactions in PE-ALD are less reliant on thermal activation.

Alternatively exposing an initially oxidized substrate surface to two, individual gaseous precursors and purging in-between allows each surface reaction to be driven to completion each cycle. This is because an individual precursor will adsorb and subsequently desorb from substrate surface areas in which the reaction has reached completion, and instead proceed to react with tm-reacted surface areas. This yields uniform and pinhole-free film deposition. Repetition of the two self-limiting surface reactions allows for near linear growth of aluminum oxide with the number of PE-ALD cycles. Aluminum oxide cycle growth has been characterized by both spectroscopic ellipsometry and quartz crystal microbalance measurements and found to be between 1.1-1.2 angstroms per ALD cycle. Notwithstanding, aluminum oxide cycle growth is temperature dependent and decreases with temperatures between 177-300° C.

Deposition of aluminum oxide on a neurovascular stent or flow diverter surface is carried out in this coating protocol with the OpAL ALD Instrument (manufactured by Oxford Instruments) at the University of Iowa Microfabrication Facility (UIMF) in an ISO 5 (Class 100) clean room. The PE-ALD process with oxygen plasma, previously described, is the aluminum oxide deposition method. In this protocol, the ALD chamber temperature is kept constant at 200° C. and the ALD cycle number is set to 300. Choice of 300 cycles of aluminum oxide deposition in this protocol was, in some sense, arbitrary. Depositing an oxide coating in the tens of nanometers thick on these devices seemed like a reasonable starting point, with the intent to optimize this thickness at a later time if necessary. The PEALD process begins when the chamber reaches a base pressure of 10 mTorr. This base pressure was suggested by Oxford Instruments based on the capacity of the vacuum pump installed with the UIMF ALD instrument.

Figure 14:
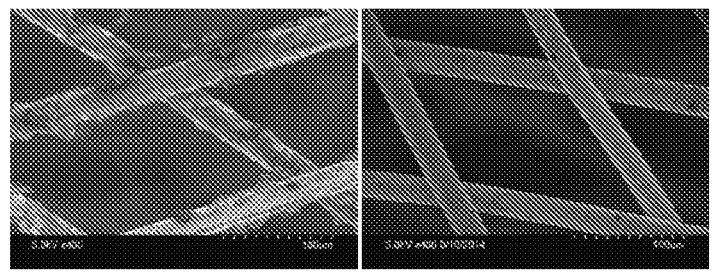
FIG. 14: (Left) SEM image of a Pipeline® Flow Diverting Device prior to ultrasonic cleaning with the established protocol. (Right) The same device after ultrasonic cleaning.

Prior to placement of the stent or diverter in the ALD chamber, the device is ultrasonically cleaned in a Branson Sonicator. This is done under a chemical hood in the UMIF ISO 5 clean room. Sonicators use ultrasound waves to produce cavitation bubbles. When these bubbles burst close to the device surface local high pressure results, leading to an instantaneous and local temperature increase. The combination of the local high pressure and temperature removes surface contan1inants at the cost of etching the surface. The sonication cleaning protocol followed is to submerge the device in the solvents acetone, isopropyl alcohol, methanol, and de-ionized (DI) water and sonicate in each for three minutes. The device is then dried under a stream of ultra-high purity (99.999°1( )) nitrogen gas for three minutes. Validation of this cleaning protocol was done qualitatively, via SEM imaging. FIG. 14 shows a Pipeline® Flow Diverting Device before and after ultrasonic cleaning with the aforementioned protocol.

The aluminum oxide cycle growth rate for the OpAL ALD instrument in the UIMF has been determined with spectroscopic ellipsometry thickness measurements on 10 individually coated one centimeter square silicon wafers exposed to 300 PE-ALD cycles. This data indicates that the aluminum oxide growth rate is ~0.095 nm per cycle at 200° C. Researchers at the UIMF have also independently tested the aluminum oxide growth rate characteristic of this instrument across a range of cycles. Spectroscopic ellipsometry thickness measurements on individual silicon wafers exposed to 100, 200, and 300 PE-ALD cycles suggest an instrument aluminum oxide growth rate of ~0.09 nm per cycle at 200° C.

Figure 15:
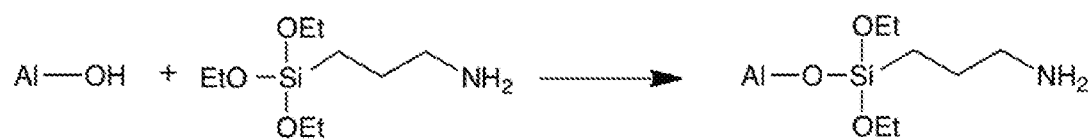
FIG. 15: A schematic of the APTES silanization chemical reaction used to functionalize the PE-ALD deposited $Al_2O_3$ layer on a stent or flow diverter device.

After deposition of the aluminum oxide layer on the neurovascular stent or flow diverter surface, the coating process proceeds by salinization of the $Al_2O_3$ layer with an amino-terminated silane, as shown in FIG. 12. Silanization of a metal oxide is not novel. Therefore reaction parameters like temperature, time and silane concentration were adapted from Ploetz et al. Specifically toluene is heated to 65° C. in an oil bath. Next the amine-containing silane, 3-aminopropyl-triethoxysilane or APTES, is added to the toluene to yield a 1% v/v solution. After the device is cleaned via the established ultrasonic cleaning protocol, it is placed in this mixture and allowed to react for 20 minutes (while stirring). A schematic of the silanization chemical reaction is shown in FIG. 15.

Upon reaction for 20 minutes, the device is removed from the toluene-APTES solution and rinsed with toluene three times, to dilute the silanization surface reaction, and finally rinsed with methanol three times to remove toluene residue. The device is then dried under a stream of ultra-high purity (99.999%) nitrogen gas for five minutes. Ultimately this reaction procedure provides an activated device surface; in other words, a device surface with free amino groups for subsequent functionalization (as shown in FIG. 15).

Figure 16:
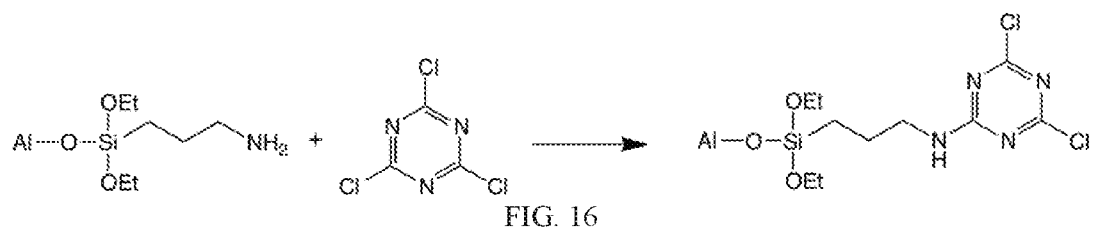
FIG. 16: A schematic of the TCT chemical reaction used to functionalize the APTES layer on a stent or flow diverter device.

The silanized device surface is further functionalized by TCT, which provides surface -Cl groups that act as coupling agents to attach the hTM. Using TCT to attach hTM is not novel and was first reported by Yeh and Lin in 2009 on a nitinol substrate. Therefore reaction parameters like temperature, time and TCT concentration were adapted from Yeh and Lin. Specifically a Schlenk flask is put under flowing nitrogen gas overnight. Next a 0.27M solution of TCT-toluene solution is made and nitrogen gas is allowed to bubble through for 20 minutes. This toluene-TCT solution is added to the Schlenk flask, still under nitrogen purge, and heated to 70° C. in an oil bath. The device, clean and dry from the silanization step, is added to the Schlenk flask and allowed to react for 4 hours and 15 minutes (while stirring). A schematic of the TCT chemical reaction is shown in FIG. 16.

Upon reaction for 4 hours, 15 minutes the device is removed from the toluene-TCT solution and rinsed with toluene three times, to dilute the TCT surface reaction, and finally rinsed with methanol three times to remove toluene residue. The device is then dried under a stream of ultra-high purity (99.999%) nitrogen gas for five minutes and placed in a clean, plastic test tube.

Figure 17:
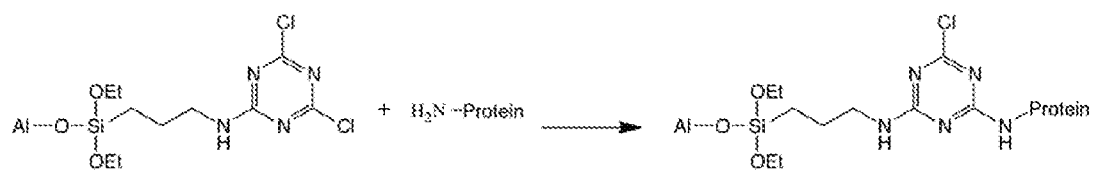
FIG. 17: A schematic of the hTM protein reaction that couples to the TCT layer on a stent or flow diverter device.

Immobilization of the hTM protein to the TCT-activated device surface is then done by following the generic protocol outlined by Yeh and Lin. This protocol consists of dissolving the hTM in PBS solution and reacting with the device at 4° C. for 24 hours. A schematic of the hTM protein reaction is shown in FIG. 17.

Figure 18:
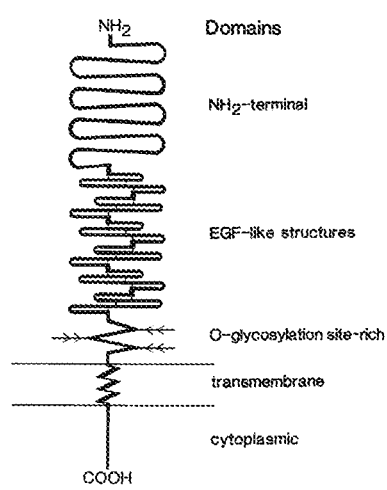
FIG. 18: A schematic of the structure of human thrombomodulin (hTM).

The hTM protein used in this protocol is human recombinant, contains only the extracellular domain, and is purchased from Sigma-Aldrich. The decision to use recombinant hTM containing only the extracellular domain is based on the fact that hTM binds thrombin in the extracellular domain. In a 1987 paper K. Suzuki et al. showed that hTM likely binds thrombin in its EGF-like extracellular domain, containing amino acid residues 227-462. The structure of hTM is shown in FIG. 18.

10 ug hTM was dissolved in 0.500 µL PBS (yielding a 0.02 mg/mL concentration of hTM in PBS). This concentration was based on considerations of cost and the volume need to submerge the device; other concentrations can be used. The specific protocol followed to carry out the protein reaction is to first UV sterilize the device in a standard cell culture hood for 15 minutes. Next the 0.02 mg/mL solution of hTM is prepared by dissolving 10 µg lyophilized hTM in 500 µL PBS in a 1 mL plastic vial and vortex to dissolve. Under the sterile cell culture hood, the sterilized device is placed in the hTM solution in a straight configuration and kept at 4° C. for 24 hours. Upon completion of the reaction, the device is removed from the hTM solution in the sterile cell culture hood, rinsed with PBS, and allowed to air-dry for half an hour.

Special consideration must be made for devices both 30 mm in length or longer, and devices 20 mm in length but with diameters greater than 4.2 mm. This is because these devices are either too long or too wide to be fully submerged in the 500 µL of 0.02 mg/mL hTM solution. In the case of devices 20 mm in length with diameters greater than 4.2 mm, the hTM solution has been diluted two-fold and the devices allowed to react for two days (at 4° C.); nevertheless, these devices can still be reacted in a straight configuration in a 1 mL plastic vial. In the case of devices 30 mm in length or longer, the hTM solution has been diluted four-fold and the devices have been coiled within individual wells of a 24-well plate; these devices were allowed to react for two days (at 4° C.).

Characterization of the Coating Layer Composition and Uniformity:

To characterize the coating layer uniformity, SEM imaging was used. In SEM imaging an electron gun generates electrons, which are focused into a beam, and accelerates them toward the sample (to an energy in the range of 0.1-30 keV). When the electron beam enters the specimen chamber it interacts with the specimen (to a depth of approximately 1 um) and generates many types of signals, the most common of which are secondary electrons and backscattered electrons. To generate the image and control magnification, two pairs of electromagnetic deflection coils raster the electron beam across the specimen—the first coil pair deflects the beam off the microscope's optical axis, while the second coil pair bends the beam back to the optical axis at the pivot point of the scan so that it can pass through the final lens aperture and interact with the sample. The signals generated from the backscattered and secondary electrons are then collected by a detector to form the image. It should also be noted that the image magnification in SEM is the ratio between the length of the raster on the viewing screen and the corresponding length on the specimen. When increased magnification is desired, the scan coils deflect the electron beam across a smaller distance on the sample. Contrast in the SEM image is the result of spatial changes in signal intensity from the beam-specimen interaction. Furthermore, the image sharpness and feature visibility in SEM are dependent upon the electron probe size, current, and convergence angle on the sample, as well as the electron beam accelerating voltage.

SEM imaging has been done on an uncoated Pipeline® Flow Diverter device and also on a Pipeline® device coated with 300 cycles of PE-ALD deposited aluminum oxide. The acquired images are shown in FIG. 19.

Figure 19:
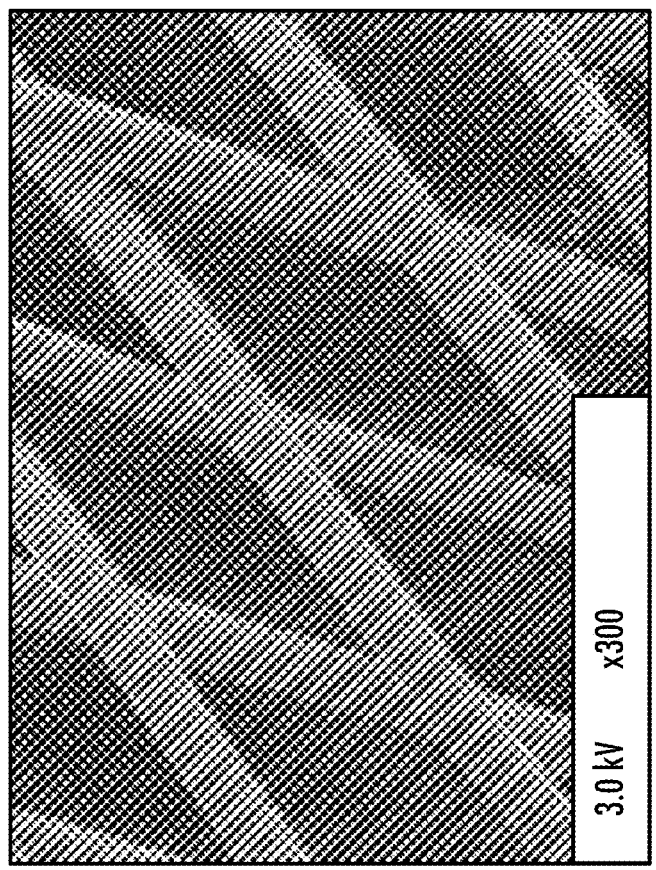
FIG. 19: (Left) SEM image of an uncoated Pipeline® Flow Diverting Device. (Right) SEM image of a Pipeline® device coated with 300 cycles of PE-ALD deposited $Al_2O_3$.
Figure 19:
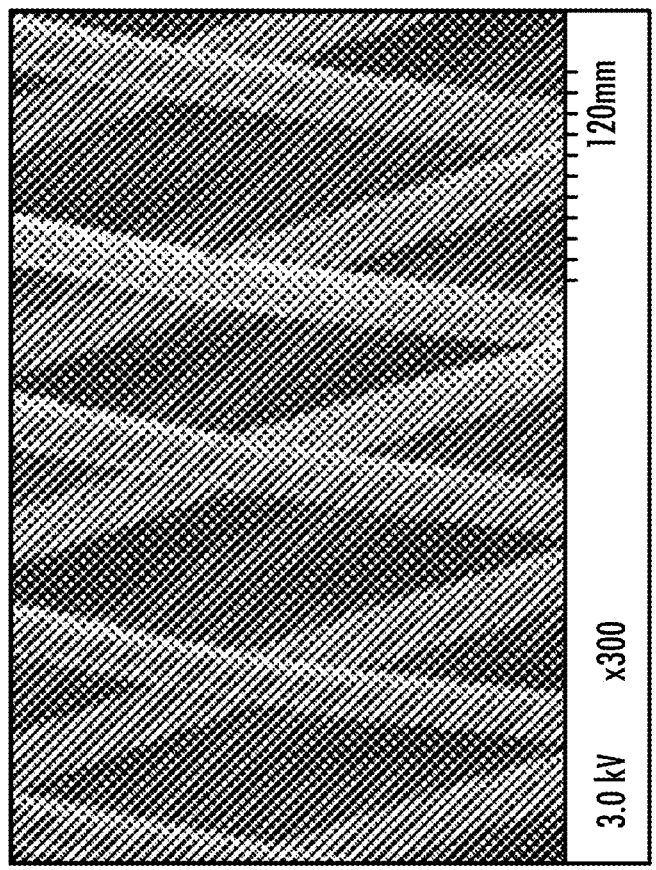

FIG. 19 shows that, at least qualitatively, the PE-ALD deposition of aluminum oxide does not significantly change the wire thickness of the Pipeline® device, nor does it significantly alter the device's mesh size; in other words, it appears that the aluminum oxide coating is conformal to the device wires. Furthermore, FIG. 19 reveals that the deposited aluminum oxide coating seems to cover wire surface scratches and smooth the wire surface.

This is in direct contrast to a coating of copolymer poly(lactic-co-glycolic acid) or PLGA that was sprayed on a Pipeline® device, which lacked conformity to the device wires. Specifically this coating formulation consisted of PLGA 50:50 (PLGA comprised of 50% lactic acid and 50% glycolic acid) dissolved in dichloromethane (DCM) in a 2% w/v solution. Glycerol and polyethylene glycol 200 (PEG, with an average molecular weight of 200) were used as surfactants. This formulation was then sprayed on a Pipeline® device via a nebulizer. SEM images of the spray-coated device and an uncoated, bare device were acquired and are shown in FIG. 20.

Figure 20:
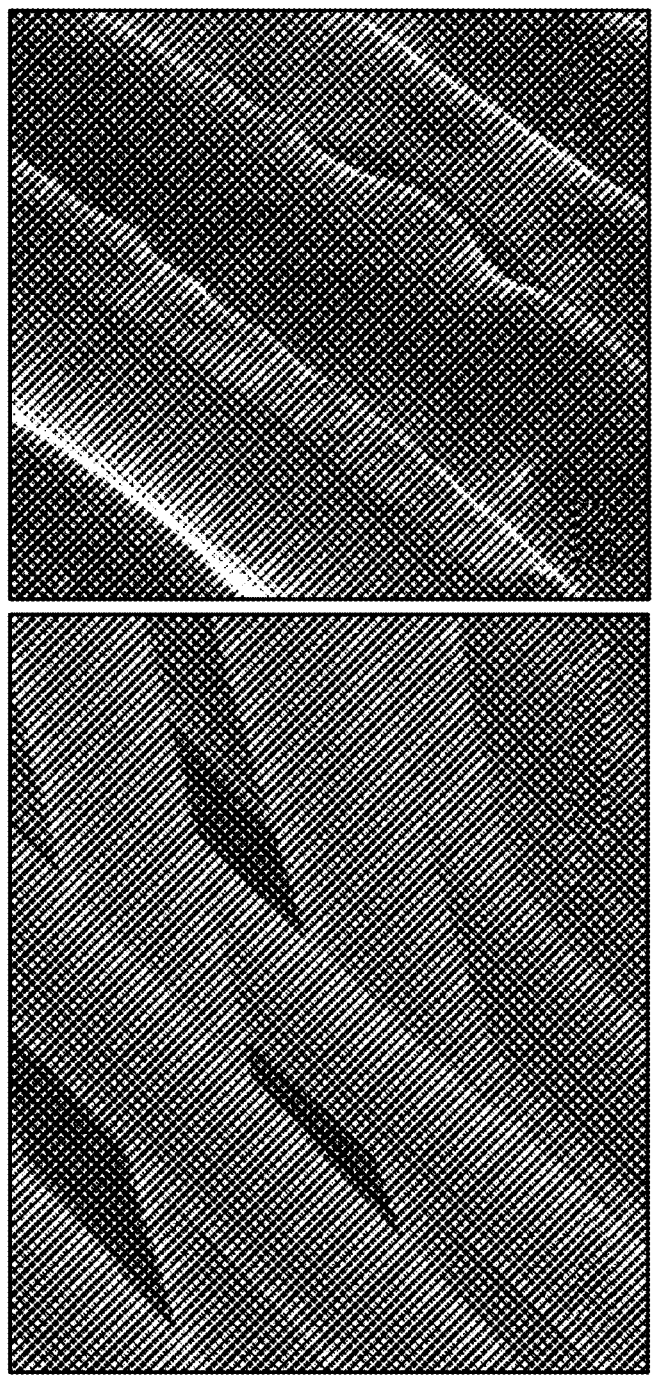
FIG. 20: (Left) Schematic of the Pipeline® Flow Diverting Device orientation on the SEM stage during image acquisition. (Middle) Acquired SEM image of an uncoated Pipeline® device. (Right) Acquired SEM image of a Pipeline® device spray-coated with PLGA 50:50 in DCM (2% w/v solution), with glycerol and PEG 200 as surfactants.
Figure 20:
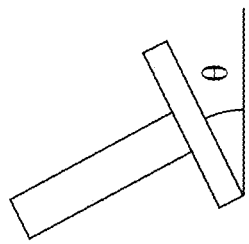

FIG. 20 reveals that the PLGA spray-coating significantly alters the wire thickness of the Pipeline® device, in addition to decreasing the device's mesh size; in other words, it appears that the PLGA spray-coating is not conformal to the device wires. Manual manipulations of devices coated in this manner indicated increased device stiffness; hence work on optimizing this spray-coating formulation was stopped in favor of pursuing the layer-by-layer coating technique previously described.

In order to assess the composition of the coating deposited by the layer-by-layer technique, X-ray Photoelectron Spectroscopy (XPS) was used. Analysis of the kinetic energies of the detected electrons enables calculation of the corresponding electron binding energies. Since each element has a unique set of binding energies, XPS can be used to identify elements on the sample surface, as well as determine their relative concentration. Furthermore, the chemical state of a sample's surface elements can be determined through XPS by identifying characteristic shifts in binding energy.

XPS was used to assess the elemental composition of an uncoated Pipeline® device. The number of detected surface electrons versus kinetic energy is shown in the XPS survey scan given as FIG. 21.

Figure 21:
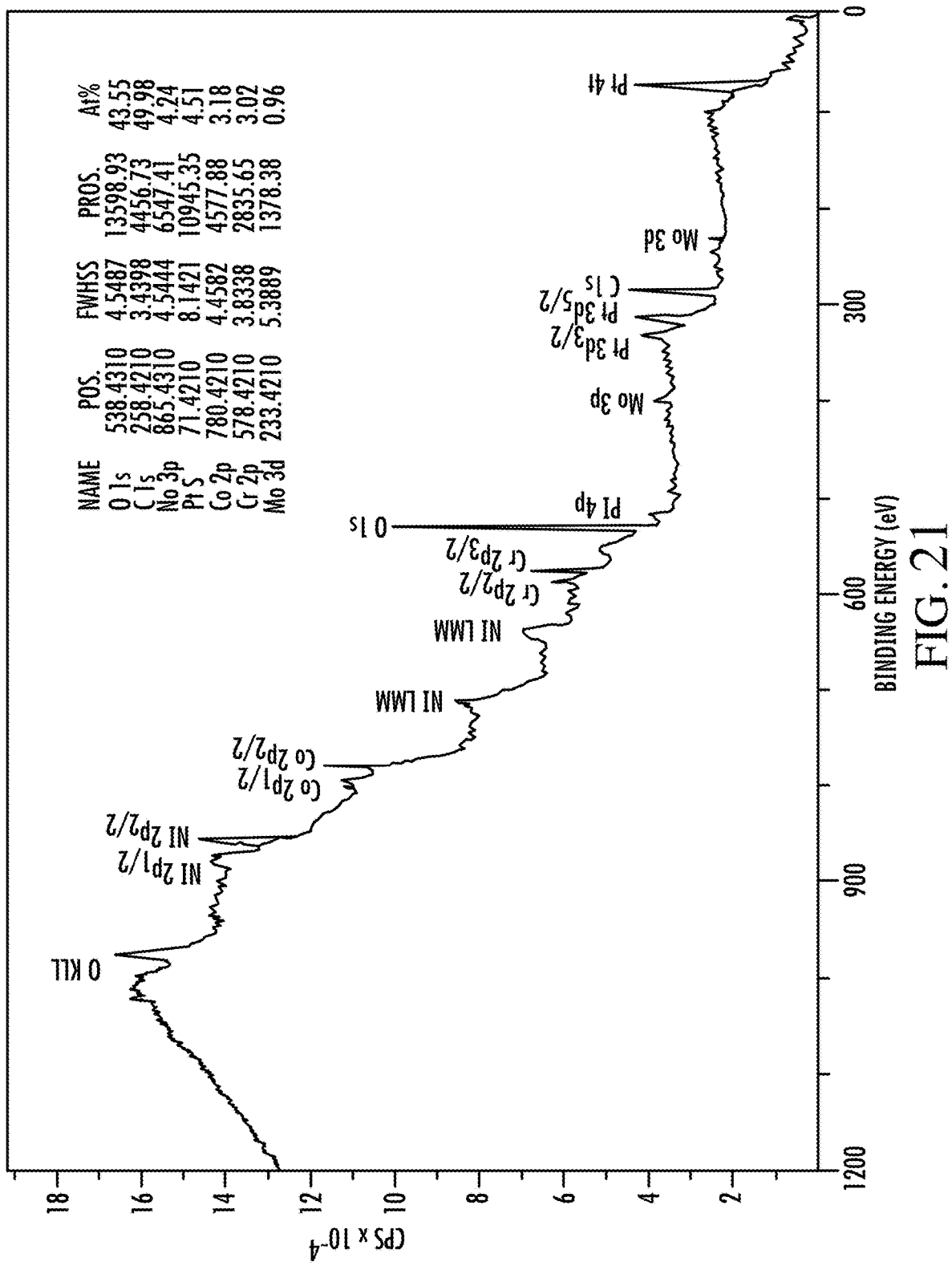
FIG. 21: XPS survey scan associated with an uncoated Pipeline® Flow Diverting Device.

FIG. 21 indicates that the metals present, and their electronic states, in a bare Pipeline® device are nickel (2p), platinum (4f), cobalt (2p), chromium (2p), and molybdenum (3d) These results support information released by Medtronic-Covidien, the device manufacturer, stating that the Pipeline® is a bimetallic design consisting of 25% platinum-tungsten and 75% cobalt-chromium—though the specific alloy compositions are unknown. With XPS it is also possible to generate intensity maps of the elemental composition of the sample surface. This is done by directing the irradiating x-rays through an aperture and limiting the detection electron spectrometer to output only the signal from electrons detected within an energy range characteristic of an element of interest Intensity maps like these give a sense for the uniformity of surface elements on a sample. XPS elemental intensity maps were generated for the metals comprising an uncoated Pipeline® device (cobalt, chromium, nickel, platinum and tungsten) and are shown as FIG. 22.

Figure 22:
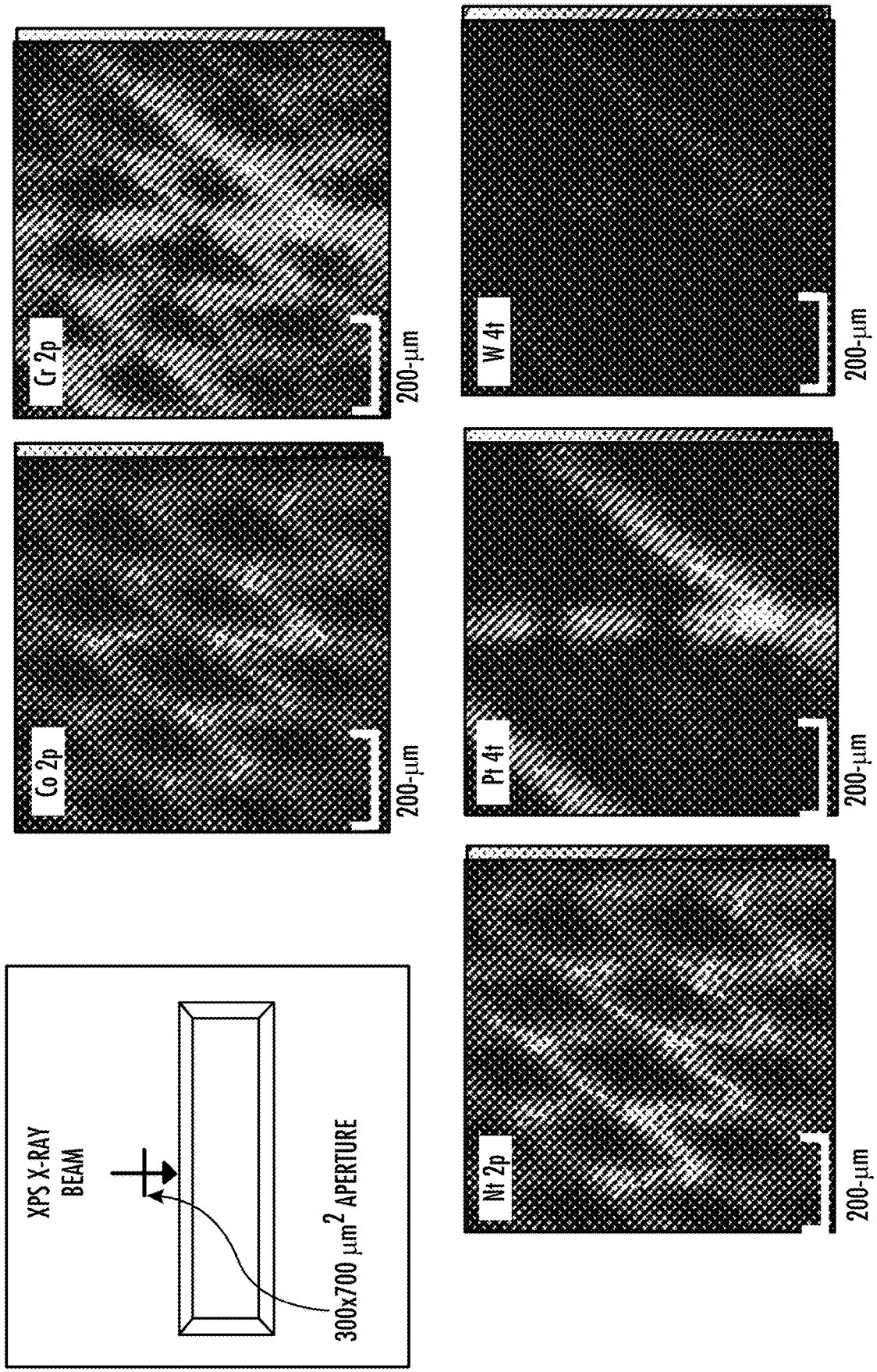
FIG. 22: XPS elemental intensity maps generated for an uncoated Pipeline® Flow Diverting Device.

FIG. 22 indicates that cobalt chromium, and nickel seem to be prevalent across the entire device surface, while platinum and tungsten comprise only certain wires of the device. This also supports the literature on device composition provided by Medtronic-Covidien, but further suggests that nickel is alloyed with both platinum-tungsten and cobalt-chromium.

Figure 23:
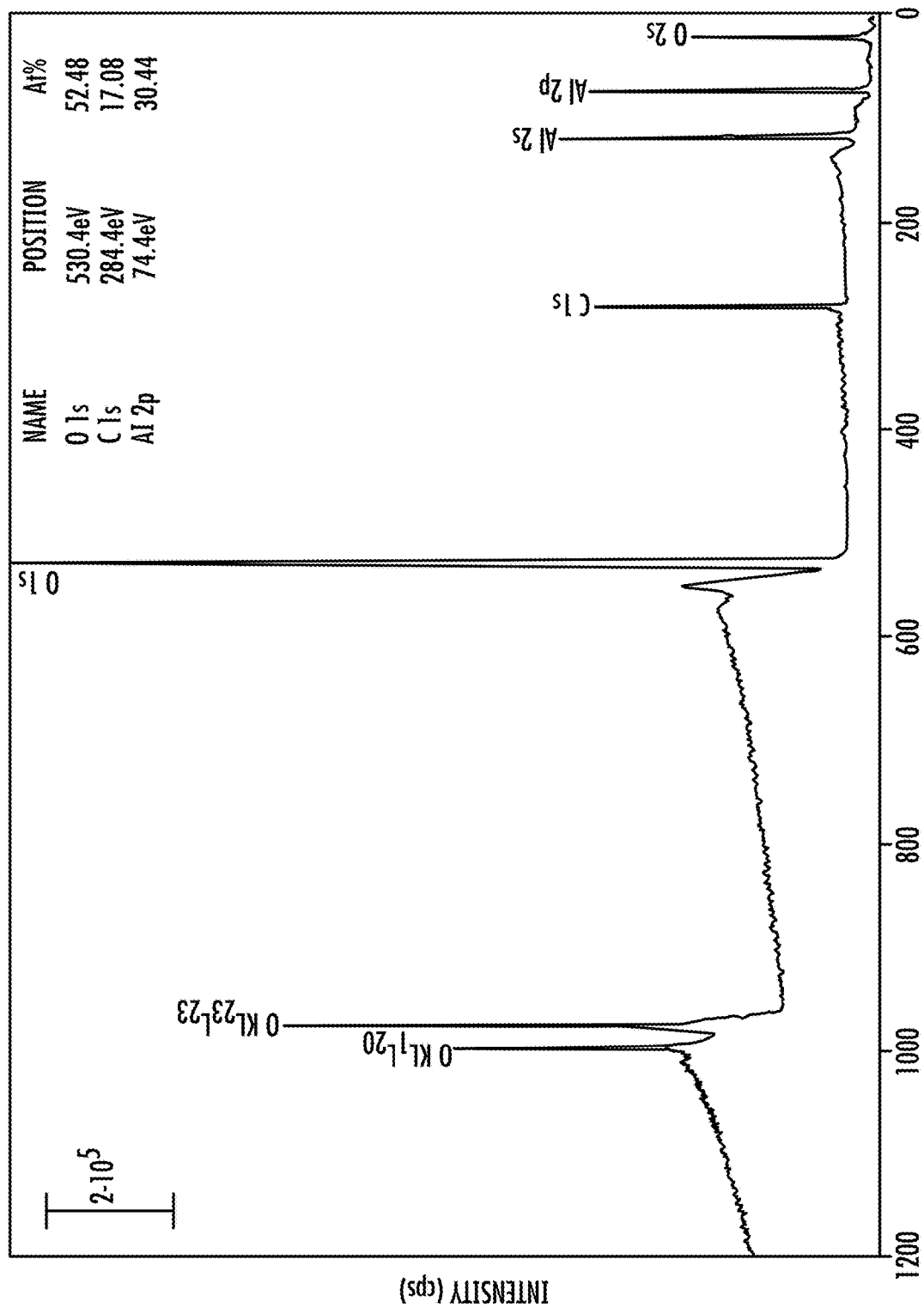
FIG. 23: XPS survey scan associated with a Pipeline® Flow Diverting Device coated with 300 cycles of PE-ALD deposited $Al_2O_3$.

XPS was also used to assess the elemental composition of a Pipeline® device coated with 300 cycles aluminum oxide by PE-ALD The number of detected surface electrons versus kinetic energy is shown in the XPS survey scan given as FIG. 23.

FIG. 23 indicates that only aluminum (Al 2s and Al 2p peaks) and oxygen (0 1s and 0 2s peaks), characteristic of aluminum oxide, are surface elements on the PE-ALD coated device. Since none of the energy peaks characteristic of the metals comprising the device show up in FIG. 13, it can be deduced that the aluminum oxide coating deposited by PEALD is greater than 10 nm, which is the approximate maximal depth that XPS can detect electrons from. To supplement this data, XPS elemental intensity maps were generated for this aluminum oxide coated device and are shown in FIG. 24.

Figure 24:
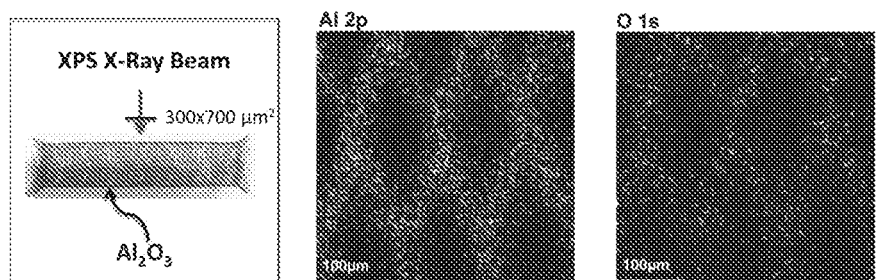
FIG. 24: XPS elemental intensity maps generated for a Pipeline® Flow Diverting Device coated with 300 cycles of PE-ALD deposited $Al_2O_3$.
Figure 25:
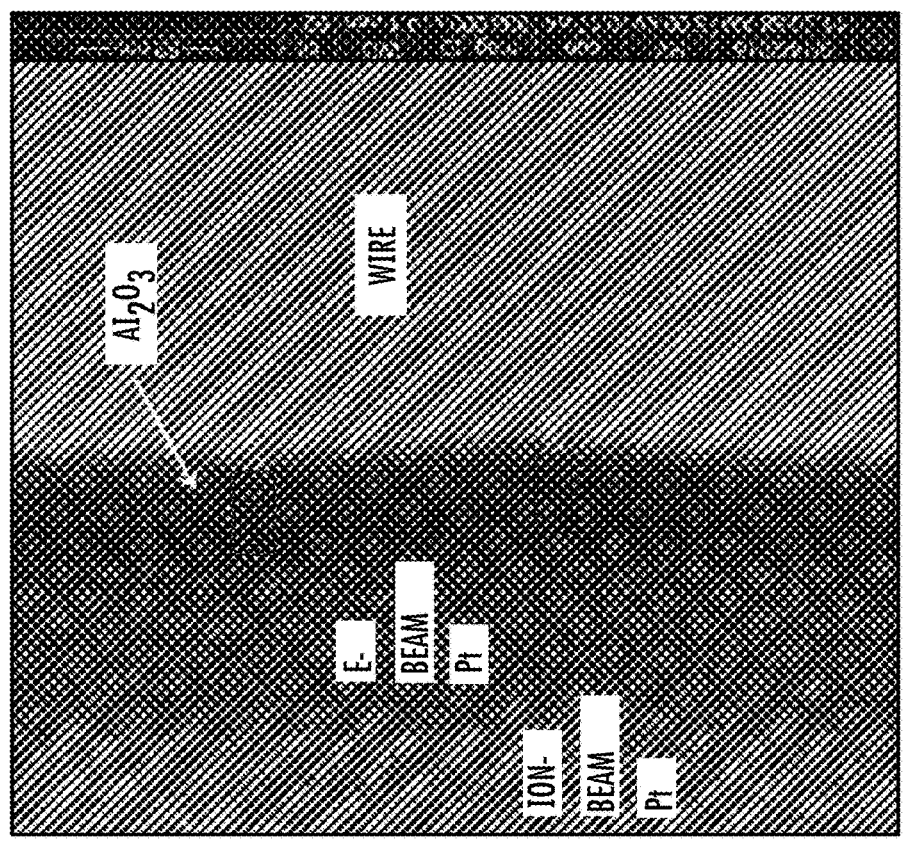
FIG. 25: (Left) FIB rectangular etch on a Pipeline® Flow Diverting Device coated with 300 cycles of PE-ALD deposited $Al_2O_3$ and platinum, the blue box denotes the approximate location of the SEM cross-sectional image. (Right) SEM cross-sectional image of the FIB etch.
Figure 25:
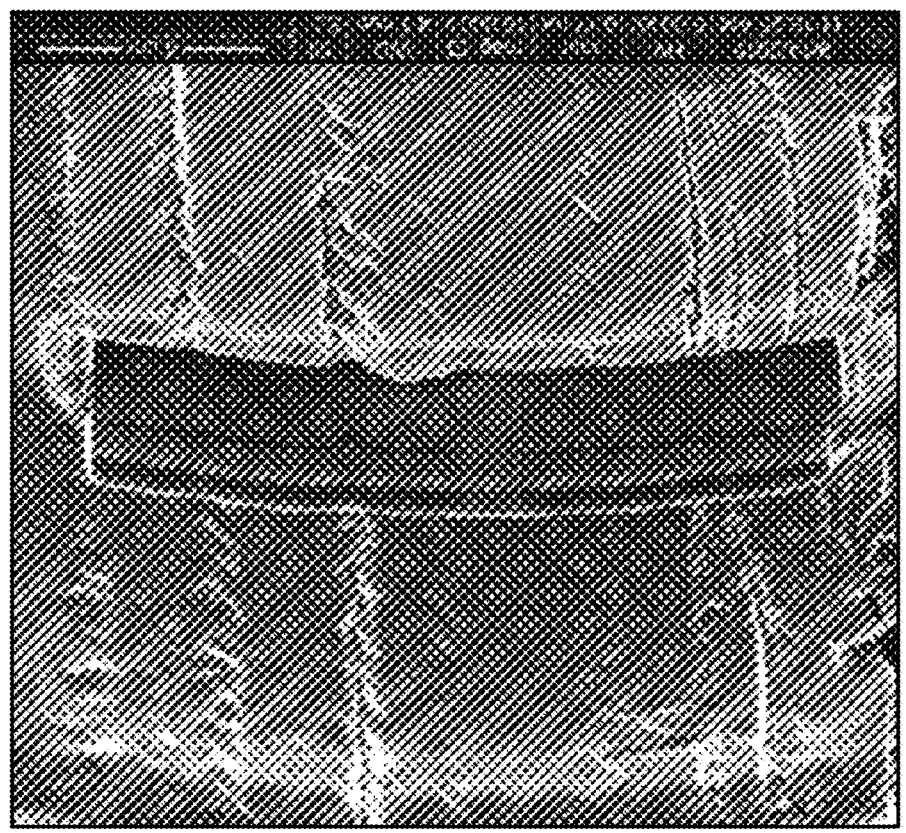

FIG. 24 indicates that the aluminum oxide coating is uniform across the device surface. To further assess the uniformity of the aluminum oxide coating, Focused Ion Beam (FIB) milling was used to etch through the aluminum oxide layer deposited by 300 cycles of PE-ALD on a MicroVention FRED™ tlow diverting device. FIB generates and directs a stream of high-energy ions from a massive element (usually Ga[1]) onto a sample. Collisions of the heavy ions with the atoms on the sample surface can result in the release of these atoms from the surface, a process called sputtering or milling. Alternatively the interaction of the heavy ion beam with the sample can result in a transfer of energy and associated release of secondary electrons that could be detected to form an image, or else the deposition of atoms or molecules into the sample surface from a gaseous layer above the sample. In this case the sputtering capability of FIB is needed to etch through the deposited aluminum oxide layer. However since the etching process is destructive, platinum metal was deposited (through both electron beam and ion beam processes) on top of the aluminum oxide layer to help preserve its integrity. Next FIB was used to etch a rectangular section on a single device wire—this etching cut through the platinum and aluminum oxide layers. To visualize the cross-section and the uniformity of the aluminum oxide layer therein, SEM imaging was used. The SEM images of the wire rectangular etch and the corresponding cross-section is shown in FIG. 25. It should be noted that the FIB and SEM imaging were both done at The University of Notre Dame.

The SEM cross-sectional image shown in FIG. 25 indicates that the aluminum oxide coating seems to be conformal to the Pipeline® device wire and uniformly deposited without holes. Image-processing software was used to measure the thickness of the aluminum oxide layer from the SEM image. The two measurements made, 30.1 nm and 30.5 nm, are similar to the aluminum oxide thickness of coated silicon wafers measured by ellipsometry at the University of Iowa (UI) and found to be 31.08±0.28 nm (n=10).

Next, XPS was used to assess the elemental composition of a Pipeline® device coated with 300 cycles aluminum oxide by PE-ALD and the silane APTES. The number of detected surface electrons versus kinetic energy is shown in the XPS survey scan given as FIG. 26.

Figure 26:
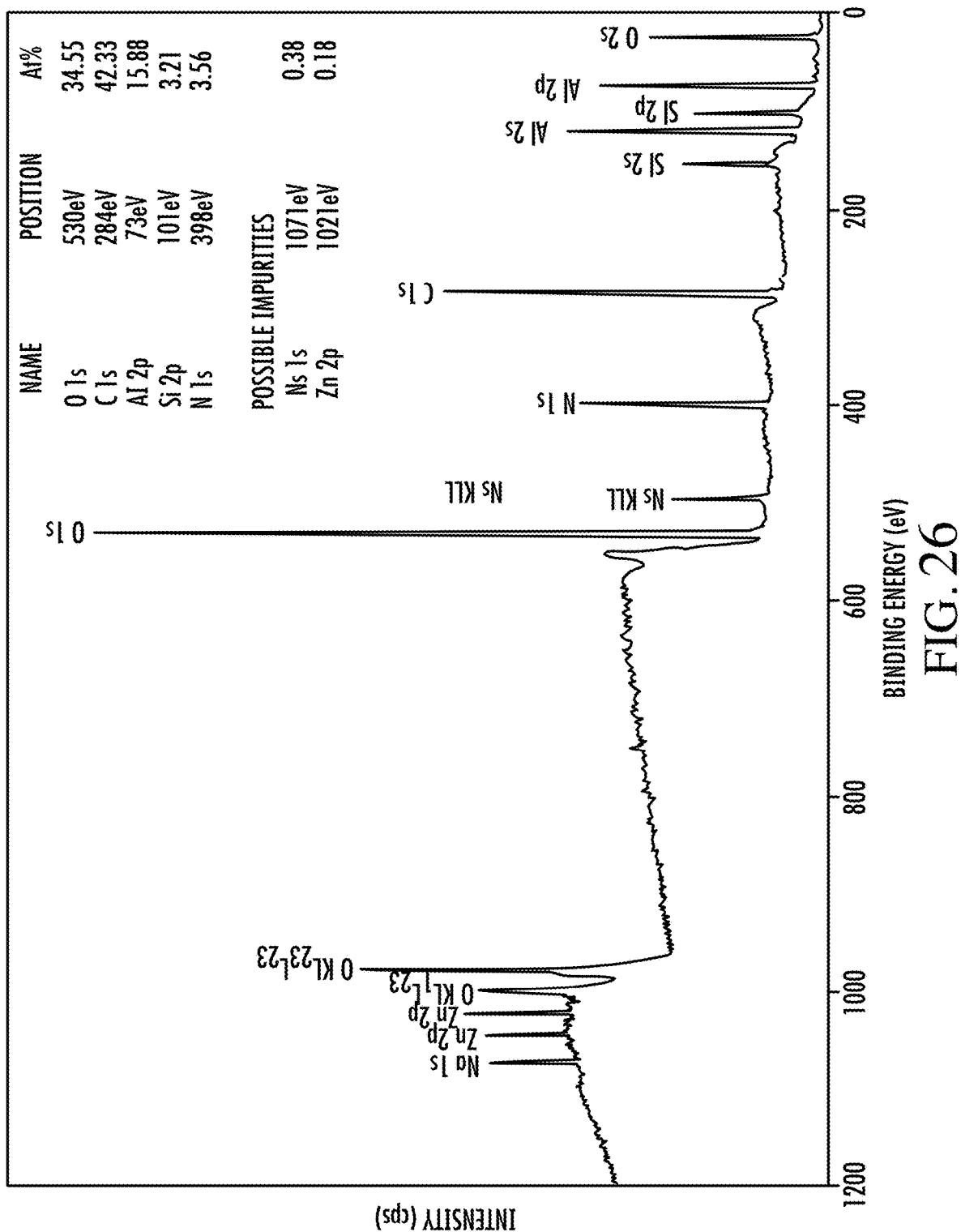
FIG. 26: XPS survey scan associated with a Pipeline® Flow Diverting Device coated with 300 cycles of PE-ALD deposited $Al_2O_3$ and the silane APTES.

FIG. 26 indicates that silicon and nitrogen (Si 2s, Si 2p and N 1s), characteristic of APTES, are present on the device surface; furthermore electrons from the aluminum oxide layer are still detected. Together this indicates that the APTES layer is thin; specifically it is less than 10 nm thick. To supplement this data, XPS elemental intensity maps were generated and are shown in FIG. 27.

Figure 27:
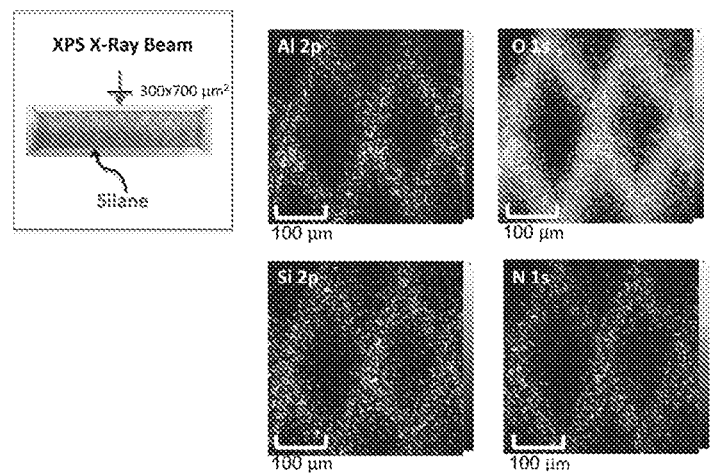
FIG. 27: XPS elemental intensity maps generated for a Pipeline® Flow Diverting Device coated with 300 cycles of PE-ALD deposited $Al_2O_3$ and the silane APTES.

Like the elemental maps for the aluminum oxide layer, the elemental maps shown in FIG. 27 indicate that the silane layer is uniform across the device surface. Furthermore FIG. 27 indicates that the APTES layer is thin since the signal from the underlying aluminum oxide layer is strong.

Finally, XPS was used to assess the elemental composition of a Pipeline® device coated with 300 cycles aluminum oxide by PE-ALD, the silane APTES, and the TCT coupler layer. The number of detected surface electrons versus kinetic energy is shown in the XPS survey scan given as FIG. 28.

Figure 28:
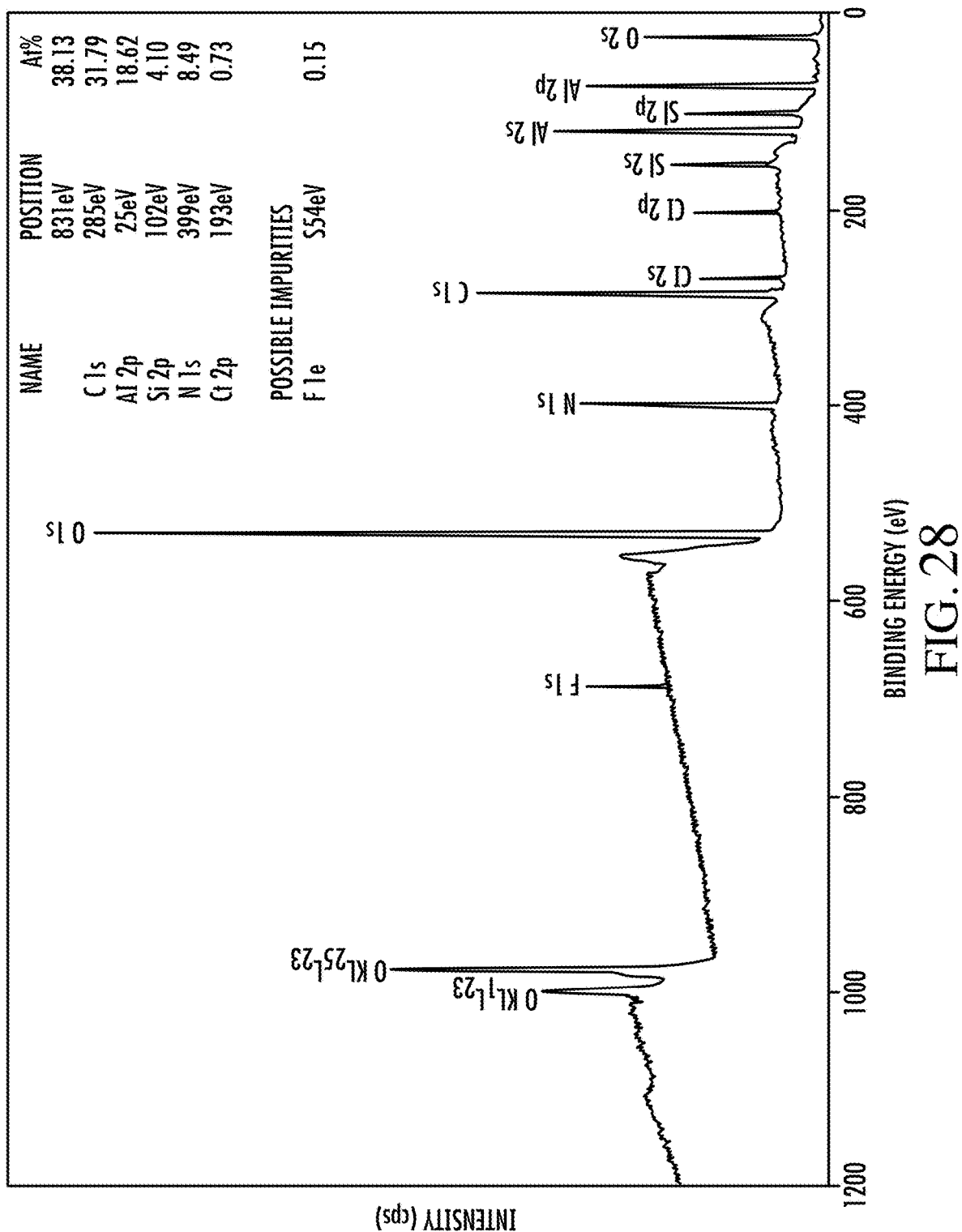
FIG. 28: XPS survey scan associated with a Pipeline® Flow Diverting Device coated with 300 cycles of PE-ALD deposited $Al_2O_3$, the silane APTES, and the TCT coupler layer.

FIG. 28 indicates that chlorine and nitrogen (Cl 2s, Cl 2p and N 1s), characteristic of TCT, are present on the device surface; furthermore electrons from both the aluminum oxide and APTES layers are detected. This indicates that the combined APTES and TCT layer is thin; specifically it is less than 10 nm thick. To supplement this data, XPS elemental intensity maps were generated and are shown in FIG. 29.

Figure 29:
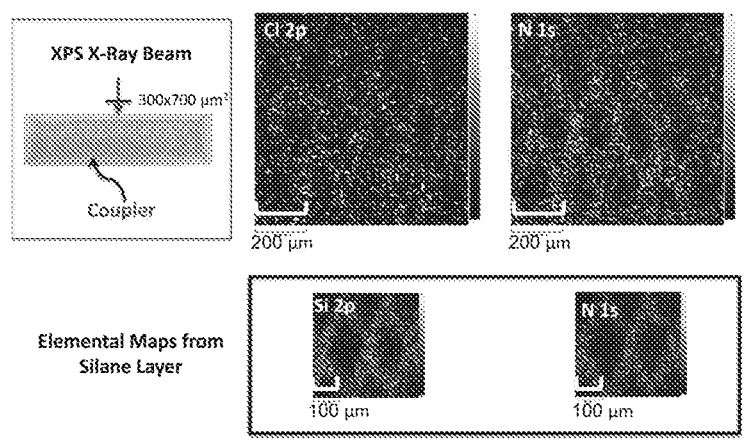
FIG. 29: (Top) XPS elemental intensity maps generated for a Pipeline® Flow Diverting Device coated with 300 cycles of PE-ALD deposited $Al_2O_3$, the silane APTES, and the TCT coupler layer. (Bottom) The XPS elemental maps for the Pipeline® device coated with 300 cycles of PE-ALD deposited $Al_2O_3$ and the silane APTES.

The XPS elemental maps shown in FIG. 29 depict what appears to be a uniform distribution of TCT on the Pipeline® device surface. However when comparing the Cl 2p and N 1s signals characteristic of the TCT layer, shown in the top of FIG. 29, to the Si 2p and N 1s signals characteristic of the APTES layer, shown in the bottom of FIG. 29, the Cl 2p and N 1s signals from the TCT layer are weaker and more diffuse. It is known that the XPS beam degrades chlorine, so this may contribute to the more diffuse chlorine signal.

The Coagulation Cascade:

The coagulation cascade is an enzymatic cascade of proenzyme activations ultimately leading to the conversion of prothrombin to thrombin. Thrombin, in turn, converts fibrinogen to fibrin, a polymer which forms the clot. Fibrin is then cross-linked and stabilized by the active form of factor XIII, or factor XIIIa. Specifically, the coagulation cascade begins in-vivo when an injured blood vessel wall exposes blood to cells underneath the endothelial layer, or cells expressing tissue factor (TF) on their cell membranes. Next, the expressed TF complexes with factors VH and VIIa (TF-VIIa) and this complex activates factor IX to factor IXa and factor X to factor Xa. Once activated, factor Xa converts prothrombin to thrombin. Initially, only a small amount of thrombin is generated, as its generation is ultimately suppressed by tissue factor pathway inhibitor (TFPI). This suppression occurs because TFPI can complex with factor Xa (Xa-TFPI), which inhibits the action of the TF-VIIa complex and, ultimately, the generation of more factor Xa. In addition to TFPI, thrombin is also inactivated by antithrombin (AT) when thrombin complexes with AT to form the T-AT complex and, to a lesser extent, by alpha2-macroglobulin (alpha2M) forming the T-alpha2M complex. The thrombin generation scheme can be seen in FIG. 30, which was originally printed in Hemker and Beguin's 1995 article in the journal *Thrombosis and Haemostasis*.

Figure 30:
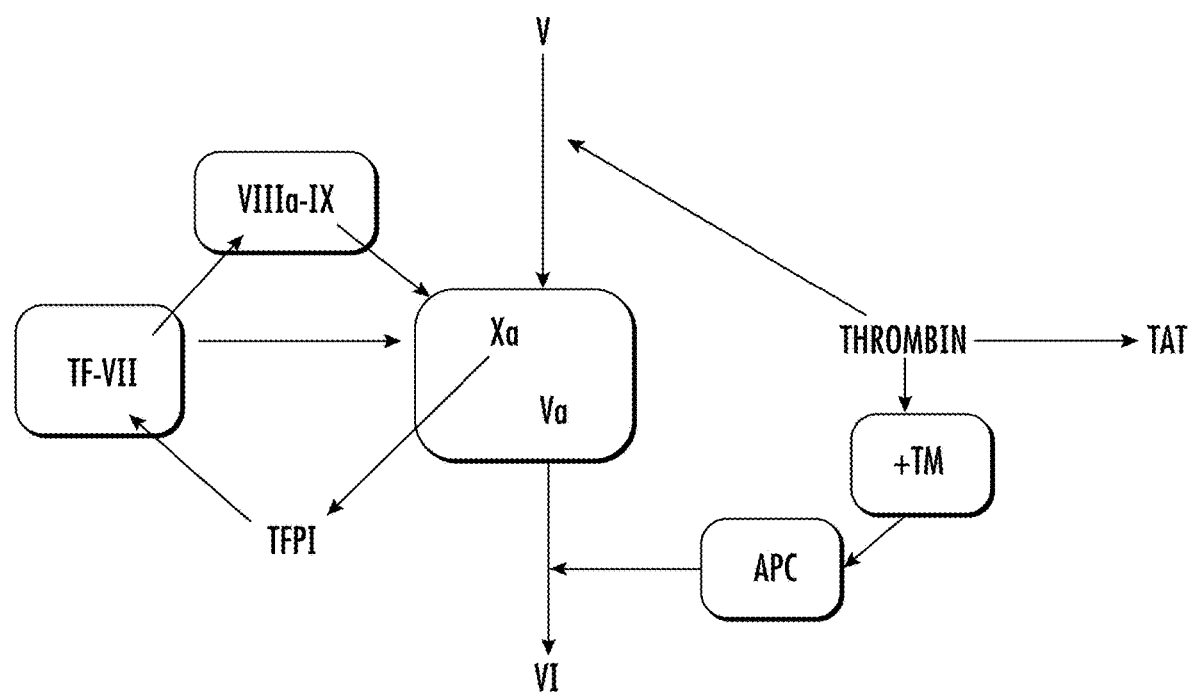
FIG. 30: Thrombin generation scheme. Lines with open arrow heads indicate a chemical conversion; lines with black arrow heads indicate activation of a proenzyme; dotted lines with open an-ow heads indicate an activating action and dotted lines with black arrow heads indicate an inhibitory action.

It should be noted that factor IX is activated to factor IXa by the TF-VIIa complex; as a result when it complexes with factor VIIIa (IXa-VIIIa) it forms an alternative factor X activator not effected by TFPI, but rather effected by the activation and inactivation of factor VIII. This is called the Josso Reinforcement Loop and, without being bound to any particular mechanism, may be the pathway whereby, at low TF levels, the precocious arrest of factor Xa generation via TFPI is prevented. The conversion velocity of prothrombin to thrombin is modulated by factors V and VIII, as shown in FIG. 30. Factors Va and VIIIa enhance the proteolytic activities of factors Xa and IXa, respectively, by approximately one thousand fold. However the generation and degradation of factors Va and VIIIa is governed by thrombin, so too is the activation and inactivation of factors Va and VIIIa. Factor V is activated by meizothrombin at a phospholipid cell membrane, whereas factor VIIIa is kept in solution by von Willebrand factor and activated by free thrombin in solution. Activated protein C, and its cofactor protein S, inactivate factors Va and VIII, leading to the downregulation of the blood coagulation cascade. Protein C is activated when its inactive form and thrombin bind to the cell surface glycoprotein thrombomodulin.

Figure 31:
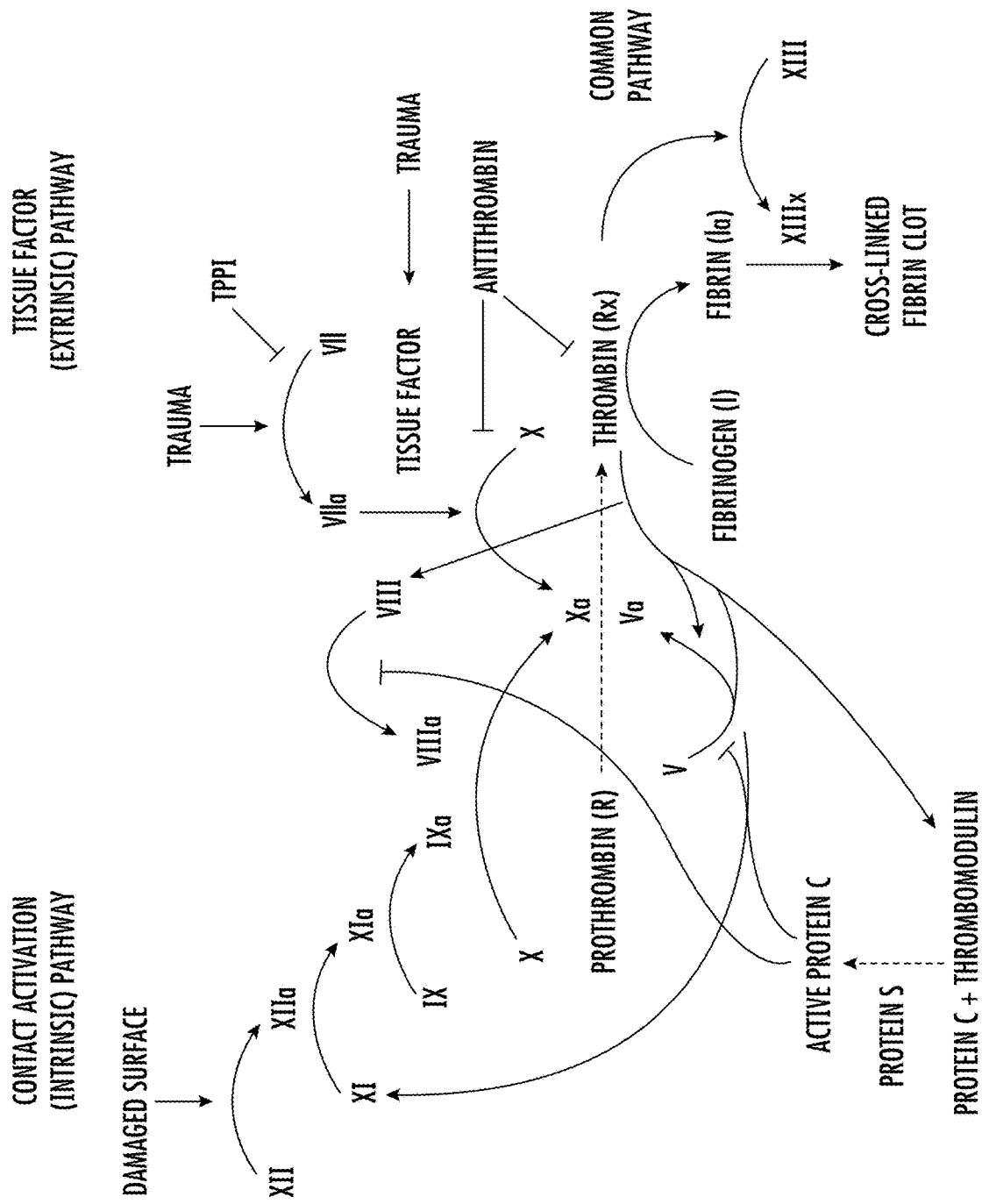
FIG. 31: The coagulation cascade. Green lines depict the thrombin's roles as a reaction catalyst. Red lines depict the primary regulatory mechanisms that keep coagulation in check.

For in-vitro testing purposes, one can think of the coagulation cascade as having two separate initiation pathways, the intrinsic and extrinsic pathways. The division of coagulation initiation into two pathways originates from in-vitro laboratory testing that measured clotting times after initiation by glass (intrinsic pathway) or by a mixture of TF and phospholipid cofactors (extrinsic pathway). The extrinsic pathway is the primary pathway by which a clot forms in-vivo and is previously described. In contrast, the intrinsic pathway begins when kallikrein activates factor XII to factor XIIIa, which in turn activates factor XI to factor XIa. Factor XIa activates factor IX and ultimately activates factor X While the intrinsic pathway plays only a minor role in the formation of fibrin in-vivo (in the sense that patients with prekallikrein and factor XII deficiencies do not have bleeding disorders), it is involved in inflammation processes. The pathway common to both, or the common pathway, begins with the conversion of prothrombin to thrombin and ends with the stabilization of the fibrin clot by factor XIIIa. A schematic of the entire coagulation cascade is shown in FIG. 31. The green lines in FIG. 31 depict thrombin's many roles as a reaction catalyst, whereas the red lines depict the primary regulatory mechanisms that keep coagulation in check.

Coagulation is also mediated by a complex interaction with platelets. After vessel injury, and a brief period of arteriolar vasoconstriction, platelets begin to adhere to the injured endothelium and promote the aggregation of more platelets to the injury site, with the intent to produce a platelet plug to stop the bleeding. First platelets activate and adhere to the subendothelial collagen exposed by vessel damage. The platelets are able to adhere due to collagen-specific receptors on their surface. Platelet adhesion is strengthened by von Willebrand factor (vWF), which is released by the damaged endothelial cells and from the platelets themselves, and acts to form additional links between collagen and the platelet surface receptors. The adhered and active platelets then begin to recruit additional platelets to the injury site, ultimately forming an aggregate. They do so by releasing the contents of their alpha granules into the blood plasma, which include factors like ADP, serotonin, platelet-activating factor, vWF and thromboxane A2. The release of these factors activates additional platelets and stimulates a $G_q$-linked protein receptor cascade that increases the concentration of calcium in the cytosol of platelets. The increased calcium level in platelets ultimately activates phospholipase A2, which modifies platelet integrin membrane glycoprotein IIb/IIIa to bind fibrinogen. The fibrinogen crosslinks with glycoprotein IIb/IIIa and facilitates platelet aggregation. Upon activation, platelets also change shape from discoid to a spiny formation, which aids in platelet aggregation. It should also be noted that release of the platelet alpha granule contents into the blood plasma leads to a high local concentration of procoagulant proteins, like fibrinogen and factors V, VIII, XL and XIII all of which support fibrin formation and stabilization. Finally because activated platelets contain the contractile proteins actin and myosin they are able to bind to fibrin strands in the dot and help draw them closer together, aiding in clot contraction and facilitating the movement of the injured tissue edges back together.

It is vital that coagulation is controlled in order to ensure that blood clots will only form where needed. One control mechanism is the hepatic clearance of activated coagulation factors. Additionally several coagulation inhibitors natively exist in blood plasma like AT, protein C, and TFPI, as shown in FIG. 31. Specifically AT complexes with thrombin and blocks its active site; additionally it inhibits factors IXa, Xa, and XIa. Protein C inhibits coagulation in its active form, activated protein C (APC), which is generated by the thrombin-thrombomodulin complex. APC and its cofactor protein S degrade factors Va and VIIIa so that they no longer facilitate thrombin generation and factor Xa formation. TFPI can complex with factor Xa (Xa-TFPI), which inhibits the action of the TF-VIIIa complex and, ultimately, the generation of more factor Xa. It should also be noted that healthy endothelia cells promote anti-coagulation. For one, healthy endothelia facilitate APC formation by allowing the cell membrane glycoprotein thrombomodulin to complex with thrombin and activate protein C. Healthy endothelia also secrete prostacyclin and nitric oxide, both of which are inhibitors of platelet activation and aggregation. Furthermore tissue plasminogen activator (T-PA) is secreted by healthy endothelia. T-PA is a catalyst for the cleavage of plasminogen to plasmin which cleaves fibrin and thereby inhibits excessive fibrin formation.

In general, all of the in-vitro coagulation assays that have been reported in the literature and used for clinical screening of coagulation protein defects examine the rate of clot formation. This means that they all initiate coagulation, thrombin generation, and ultimately fibrin clot formation. As a result soluble proteins are generated that are detected by either increased impedance or decreased optical clarity, based on the measurement instrumentation used. Any defect in the clotting process will manifest itself as a time delay in clot formation; this also means that the addition of any inhibitory antibody or anticoagulant will also effect the clot formation time. The three most common in-vitro assays to measure the rate of clot formation are the activated partial thromboplastin time (aPTT), the prothrombin time (PT), and the thrombin clotting time (ThCT). The aPTT assay only assesses the functionality of the intrinsic and common coagulation pathway proteins; to perform this assay, equal parts of a negatively charged surface, a phospholipid mixture, and patient citrated-blood plasma are incubated. Calcium chloride is added, in a concentration of 30 nM, to recalcify the citrated plasma and the time to clot formation is then measured. In contrast, the PT assay only assesses the functionality of the extrinsic and common coagulation pathway proteins. In this assay either tissue-derived or recombinant TF is incubated with phospholipids and patient citrated-plasma. The plasma is then recalcified by adding calcium chloride (to a concentration of 30 nM) and the time to clot formation is measured. In contrast to the aPTT and PT assays, the ThCT assay directly measures the conversion of fibrinogen (soluble) to fibrin (insoluble). In the ThCT assay an excess of thrombin is added to patient citrated plasma and the clotting time is measured. It is important to realize that the aPTT and PT assays have different sensitivities for detection of coagulation abnormalities depending upon the factor tested, the commercial reagents used in the assay, as well as the measurement equipment used. Since the ThCT assay only measures the conversion of fibrinogen to fibrin, it is generally accepted that dotting times outside the 95% confidence interval of dotling times collected for a population of at least 20 donors suggests reduced fibrinogen levels, abnormal fibrinogen function, or the presence of a thrombin inhibitor. Rotational viscometry can also be used to measure time to clot formation; in fact the methodology, called the thromboelastography (or TEG), is not new and was pioneered by Hartert in 1948. Specifically the TEG measures the torque applied to a stationary pin (connected to a torsion wire) by whole blood or plasma in a heated viscometer during oscillating rotation. The torque measured is minimal in an unclotted sample, but increases during clot formation due to increased sample viscosity and clot-mediated bridge formation between the pin and the cup walls: this torque is increasingly transferred to the pin. There is currently insufficient evidence to prefer using TEG over other standard coagulation tests; particularly TEG estimates of fibrinogen have shown moderate to poor correlation to those observed in PT assays.

The Calibrated Automated Thrombogram (CAT) In-Vitro Assay:

Another metric that can be used to assess in-vitro coagulation is the amount of thrombin generated in a sample. This is because the traditional in-vitro assays that assess clot formation do not measure the sample's full thrombin generation capacity, since fibrin clots form early in the thrombin generation process when approximately 95% of thrombin has yet to form. Determining the extent of plasma's thrombin generation capacity is important; this is because thrombin is pivotal in the coagulation cascade and functionally can both amplify and dampen it. Specifically thrombin can amplify the cascade since it catalyzes the conversion of fibrinogen to fibrin, promotes increased thrombin formation through activation of factors XI, V and VIII, promotes clot stabilization by activation of anti-fibrinolytic factors, activates damaged endothelia to synthesize factors like vWF and tissue plasminogen activator, as well as acts as a platelet activator. In contrast, thrombin can function to dampen the cascade when it complexes with hTM; this complex activates protein C, a prominent anticoagulant. Because of thrombin's vital role in the cascade, it is thought to be a metric predictive of a patient's thrombosis risk. In fact, thrombin generation assays in platelet-poor plasma (PPP) are sensitive to all clotting factor deficiencies, except for factor XIII; furthermore, they are sensitive to all anticoagulant drugs tested. They are also sensitive to a lack of AT, as well as resistance to proteins C, S, and APC, which manifest as increased thrombin generation. Thrombin generation assays in platelet-rich plasma (PRP) are sensitive to vWF, anti-platelet drugs, and agents that increase platelet reactivity. Despite the usefulness of such assays, their application has been limited mostly due to technical issues. This is because these assays traditionally measured thrombin generation by sub-sampling a clotting plasma sample, a labor and time-intensive methodology. However current thrombin generation assays use a fluorogenic substrate and thereby facilitate a continuous measurement of thrombin generation. Furthermore, advances in software and instrumentation have contributed to the automation of large portions of the current assay workflow and allow for reproducible data collection outside of specialized labs.

Figure 32:
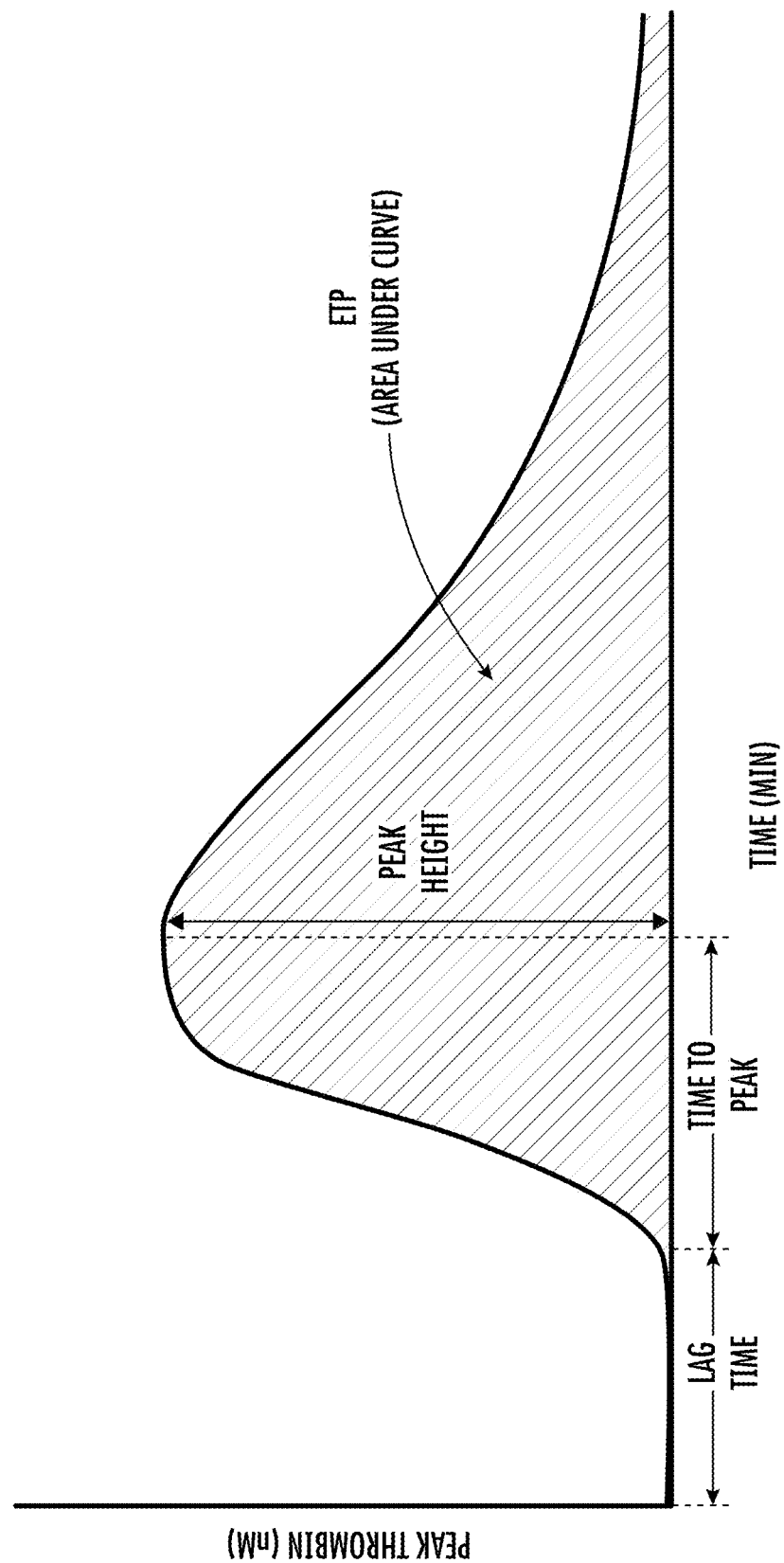
FIG. 32: Thrombin generation time course in recalcified, activated plasma. Four major parameters are identified. Peak Height refers to peak thrombin concentration.

There are currently two commercially available fluorogenic thrombin generation assays—the Calibrated Automated Thrombogram (or CAT) developed by Hemker et al and marketed by Thrombinoscope, a Stago Group Company based in Maastricht, Netherlands and the Technothrombin TGA method marketed by Technoclone in Vienna, Austria. While these assays differ in their technical details, both utilize a fluorogenic substrate specific to thrombin that is added to recalcified plasma (either PRP or PPP). When the substrate is cleaved by thrombin it fluoresces and the resulting signal is measured by a 390 nm excitation/460 nm emission filter set on a microplate reader; thus, thrombin generation is correlated to the signal intensity of a specific fluorophore. This signal takes the shape of a skewed-bell shape profile because native AT and alpha2M in the plasma inhibit thrombin formation and so the concentration of active thrombin eventually falls to a basal equilibrium level. Several important parameters can be measured from the free thrombin time course curve, which are lag time, peak thrombin concentration, time until peak thrombin concentration, and the endogenuous thrombin potential (ETP). Lag time is taken as the time to first detectable free thrombin measurement Peak thrombin is the maximum concentration of free thrombin generated over the course of the experiment; time to peak thrombin generation is the time from the first detectable free thrombin until the peak thrombin activity. ETP is the area under the free thrombin versus time curve. All of these parameters are shown in FIG. 32.

The Technothrombin TGA and CAT assays have one important difference and that is that the CAT assay uses an internal standard to generate the free thrombin time course; in other words, the CAT assay allows for computation of free thrombin activity as a function of time by comparing the fluorescent signal of a thrombin generating sample to that from a known and stable concentration of thrombin that is measured simultaneously in a parallel plasma sample. Producing a constant and stable fluorescent signal from a known thrombin concentration is not trivial: this is because thrombin is readily inactivated in plasma by AT and alpha2M, thus it cannot be used for calibration. Instead the stable complex of thrombin-alpha2M is used as a calibrator in the CAT assay. Furthermore because the florescent signal produced by the thrombin-alpha2M complex differs when incubated in buffer and plasma, the CAT assay carries out calibration by incubating the thrombin-alpha2M complex in the same plasma that is used to test the thrombin generating sample. The use of an internal calibration standard is important in fluorogenic thrombin generation assays because the rate of fluorescent signal increase is not linearly related to the amount of thrombin produced in these tests. The reason for this is three-fold, first the fluorogenic substrate is consumed throughout the experiment so that as the reaction proceeds the velocity of fluorophore formation per unit substrate decreases (substrate consumption). Second, the absorbance of either emission or excitation light by plasma elements prevents the equal excitation and capture of light from deeper in the assay liquid, meaning that fluorescence intensity is not linearly related with fluorophore concentration (inner filter effect). Finally while it is known that alpha2M inhibits physiologic thrombin function it does not inhibit the thrombin-mediated cleavage of the substrate to its fluorogenic state, resulting in residual fluorescent signal that has no physiological relevance (alpha2M effect); this means that only the fluorescent signal from free thrombin (i.e. thrombin not bound to alpha2M) has physiological relevance. Thus, the CAT assay uses its internal calibration standard as a means to adjust the free thrombin signal from a thrombin generating sample to account for discrepancies caused by substrate consumption, the inner filter effect, and the alpha2M effect. As a result, the CAT assay is superior in methodology to the Technothrombin TGA assay; hence it was chosen as the fluorogenic thrombin generation assay to test the inventive coating technology.

The methodology and data analysis for the assay were determined independently. Specifically the assay methodology was pieced together from information contained in the *Thrombogram Guide*, a CAT methodology and software guide produced and distributed by Thrombinoscope. The thrombin calibrator (or known amount of thrombin, our purchased calibrator has activity equivalent to 700 nM human thrombin), fluorescent substrate and buffer (including $CaCl_2$), and the PRP reagent (which is the recombinant TF trigger used to initiate thrombin generation in PRP) were all purchased as part of a kit through Thrombinoscope, as were 50 Immulon 2HB 96-well microplates (U-bottom).

The CAT methodology, as outlined in the *Thrombogram Guide*, can be roughly broken down into the three generic steps of PRP preparation, preparation of the test microplate, and collection of the associated kinetic fluorescence intensity measurements from a fluorimeter. The PRP preparation step begins by collecting human whole blood into 3.2% sodium citrate using a 20 gauge needle (commensurate with the standard hospital blood collection procedure). Within 30 minutes of blood collection the whole blood sample should be centrifuged in a swinging-bucket centrifuge to separate the PRP. In this thrombogram test, one unit of human whole blood (~450 mL) was obtained from a single donor from ZenBio, Incorporated. The human whole from ZenBio was obtained one day post collection and stored at 2° C. A test thrombogram assay was run on the same day. The test thrombogram assay consisted of running wells containing the thrombin calibrator, a suite of diluted thrombin calibrators (between 0-75% thrombin calibrator), blank wells (or wells containing PRP, PRP reagent, and fluorescent substrate only), wells containing glass shards (in addition to PRP, PRP reagent, and fluorescent substrate), and wells containing pieces of linear low-density polyethylene tubing (LLDPE, in addition to PRP, PRP reagent, and fluorescent substrate) in the fluorimeter and collecting the corresponding kinetic signal intensity measurements. The thrombogram assay testing coated devices was run on day two post collection. To separate the PRP for the thrombogram assay, 100 mL of the whole blood unit was poured, under a sterile cell culture hood, into two plastic 50 mL centrifuge tubes. These tubes were centrifuged for 10 minutes between 18-20° C. at 150 g in a swinging bucket centrifuge; following this, the blood was centrifuged again at the same temperature and speed for five minutes in order to maximize the supernatant that could be collected. The supernatant was then collected via Pasteur pipette cautiously, in order to avoid sucking up white cells from the buffy coat, placed in a plastic test tube, and gently mixed—this is the PRP. Next 100 µL of this PRP was transferred to a small test tube and the platelet count was measured on the Sysmex XE-2100 CBC analyzer in 2174 Med Labs, which is the same model used clinically to measure human complete blood counts (CBC). The remaining PRP was stored in a tissue culture shaker at 37° C. After the PRP platelet count was recorded, approximately half of the PRP was pipetted into new plastic centrifuge tubes and spun again at 2000 g for 10 minutes at room temperature: this spinning was repeated for five minutes at the same speed and temperature to maximize the supernatant that could be collected. The supernatant was then pipetted off and transferred to a new plastic centrifuge tube—this is the PPP. This PPP was then used to adjust the PRP to approximately 150 platelets/nL and also stored in the tissue culture shaker at 37° C. To ensure the adjusted platelet count was approximately 150 platelets/nL, the platelet count of 100 µL of the adjusted PRP was measured via the Sysmex XE-21 00 CBC analyzer. After it was confirmed that the platelet count of the PRP was properly adjusted, the thrombogram test microplate was prepared. To do this one vial of the fluorescent substrate buffer (purchased from Thrombinoscope and called Fluo-Buffer) was warmed in a water bath for approximately 10 minutes; 10 mL of deionized (DI) water was also warmed in the bath. Once warm, 40 uL of fluorescent substrate (also purchased from Thrombinoscope and called Fluo-Substrate) was added to the Fluo-Buffer under the cell culture hood and was immediately vortexed, forming FluCa solution. To reconstitute the thrombin calibrator (purchased from Thrombinoscope), 1 mL of DI water was added to the vial. After 10 minutes, the thrombin calibrator vial was shook carefully; likewise to reconstitute the PRP reagent (purchased from Thrombinoscope) 1 mL of DI water was added to the vial under the cell culture hood and after 10 minutes the vial was shook carefully. The stents used in the assay were two 5×26 mm FRED™ flow diverting devices (manufactured by MicroVention). Half of a FRED™ device was coated with all the inventive coating layers following the established coating protocol (called a TM stent reacted with 0.02 mg/mL of hTM in PBS), half of a device was coated with all the layers except the hTM protein again following the protocol (called a TCT stent), and the remaining device was left bare. Because Thrombinoscope advises to run the CAT assay components in triplicate, the TM stent piece was cut into three smaller pieces of approximately the same size. These small TM stent pieces were each placed in a separate well of the 96-well microplate. Likewise both the bare stent and the TCT stent piece were cut into three smaller pieces, each similarly sized, and placed into individual wells. Three small glass shards were cut from the tip of a sterile glass pipette; three small pieces of sterile LLDPE (purchased from Freelin-Wade), of similar size as the glass, were cut and placed in individual wells. Next the thrombin calibrators were added to the microplate. Undiluted calibrator, as well as calibrator diluted by 25%, 50%, 75%, and 100% with PPP were added to individual wells in 20 µL aliquots (and in triplicate). Additionally 5 µL of the 0.02 mg/mL hTM-PBS solution that the TM stents were incubated in was added to individual wells in triplicate. A schematic of the constituents of the microplate is shown as FIG. 33.

Figure 33:
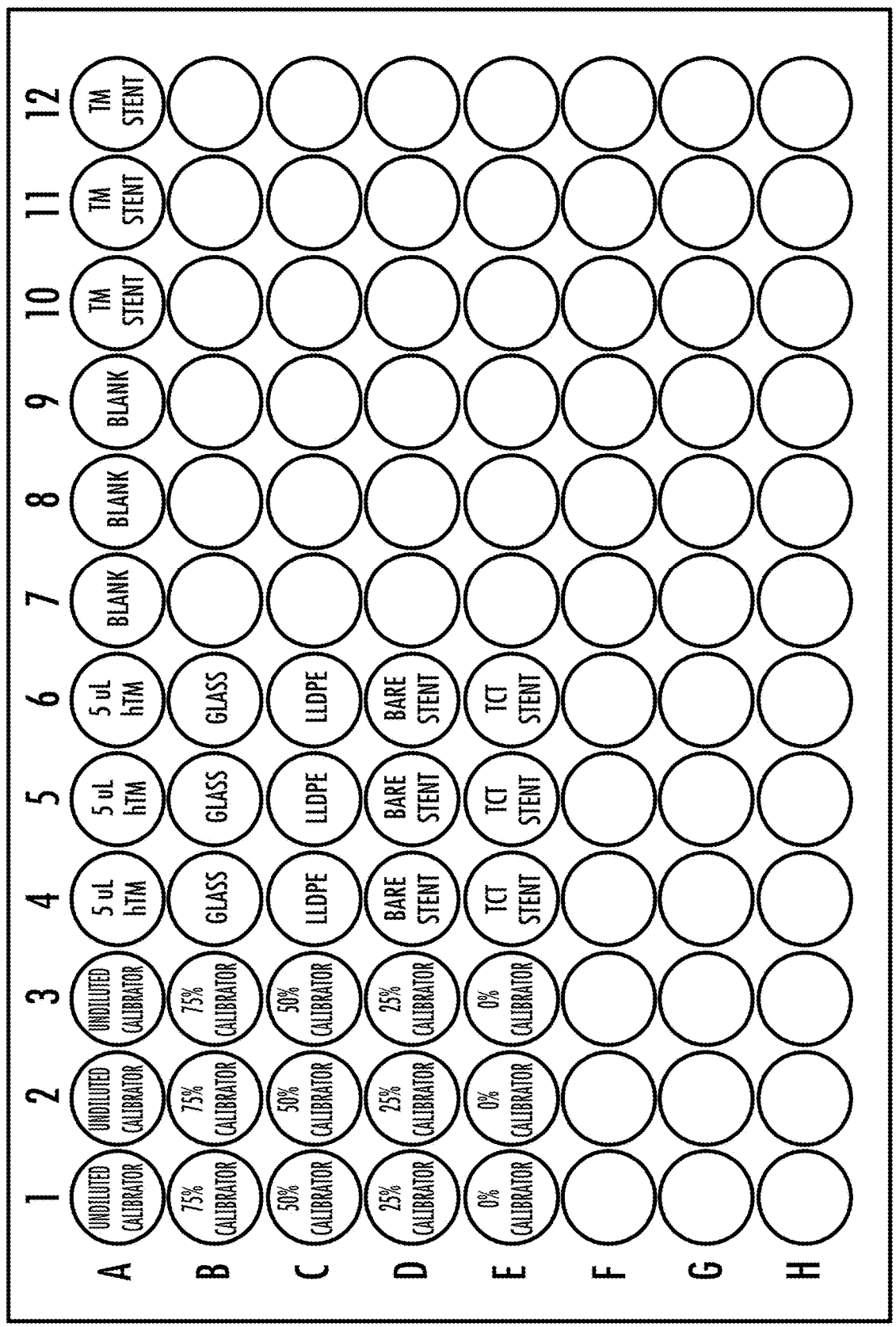
FIG. 33: Constituents of the 96-well plate run in the CAT assay. LLDPE refers to Linear Low-Density Polyethylene; hTM refers to the human recombinant thrombomodulin purchased from Sigma-Aldrich; TCT stent refers to a stent coated with every layer except the hTM layer: TM stent refers to a stent coated with every layer.

Next, 80 µL PRP was added to each of the wells containing thrombin calibrator (wells in microplate columns 1-3, refer to FIG. 33). Likewise 80 µL PRP was added to the remaining wells; additionally, 80 µL PRP reagent was added to these wells. The SpectraMax M5 fluorimeter (manufactured by Molecular Devices) was turned on and allowed to warm to 37° C. After adding 20 µL of FluCa to each well, the microplate was placed on a shaker for three minutes and then immediately placed in the fluorimeter. The kinetic measurement was set to take a reading every 23 seconds for duration of one hour 15 minutes; the M5's excitation filter was set to 390 nm and the emission filter was set to 460 nm. After changing these settings, the kinetic measurement reading of the florescent signal from thrombin commenced. After one hour 15 minutes, the data was outputted into a text file and saved.

To analyze the collected thrombin fluorescent signals from each well over time, the strategies outlined in H. C. Hemker's 2013 paper *Data Management in Thrombin Generation* was used. The general idea of the data analysis is to correct the experimentally measured thrombin calibrator signal intensities for the substrate consumption and inner filter effects by determining their ideal values, and to ultimately compute a value called the calibration factor from this corrected calibrator data. Once the calibration factor is known, it can be applied to the ideal, or corrected, tluorescence signal intensities from thrombin generating (i.e. unknown) samples, yielding a total ideal thrombin concentration integral for each. To account for the alpha2M effect on the unknown samples, the fluorescent signal corresponding to free thrombin alone is mathematically dissected from each total thrombin concentration integral. Equations can then be fitted to each total free thrombin concentration integral, the derivatives of which are the free thrombin generation time-courses for each unknown sample.

In regard to this data analysis it should be mentioned that the raw fluorescent signal intensity data must to be properly organized. Originally the signal intensity data outputted from the SpectraMax M5 fluorimeter is separated by timepoint, as shown in FIG. 34.

For analysis purposes the signal intensity data should be organized relative to microplate well, as shown as FIG. 35.

MATLAB® computer code was written to transpose the raw signal intensity data such that it is organized relative to microplate well, or organized as shown in FIG. 35. Once the data was organized in this manner all manipulations were done in Microsoft Excel. To start, each series of triplicate thrombin calibrator wells was averaged so that one average signal intensity curve (or average fluorescence curve) corresponded to the undiluted calibrator, as well as each diluted calibrator. Because of substrate consumption and the inner filter effect, experimentally measured fluorescence curves, like those corresponding to thrombin calibrators, will stop increasing and eventually plateau even while enzymatic activity continues. To correct for substrate consumption and the inner filter effect Hemker et al. developed a mathematical transformation called the H-Transform, which transforms the experimentally measured fluorescent signal into the signal that would be obtained if substrate consumption and the inner filter effect did not play a role in the signal measurement and acquisition. While the H-Transform is an approximation, correction for substrate consumption and the inner filter effect based on theory would require determining five parameters for each fluorescence curve (two kinetic parameters related to substrate consumption, as well as three parameters characterizing the inner filter effect), which is theoretically difficult and practically impossible. In contrast, the H-Transform requires a single parameter, α, and is shown as Equation 4.

$$F_{ideal} = \alpha(\arc \tan(F_{exp}/\alpha)) \tag{4}$$

In Equation 4, $F_{exp}$ is the experimentally measured fluorescence intensity, α is a constant, and $F_{ideal}$ is the fluorescence intensity in the absence of substrate consumption and the inner filter effect (i.e. the transformed, ideal intensity). The correct value of α is the one that converts the fluorescent signal into a straight line when the fluorescence intensity is constant; in other words, when the amidolytic activity (or the amide bond cleavage activity) of thrombin on the fluoro-substrate is constant. Constant amidolytic activity in human plasma is always due to the thrombin-alpha2M complex, used as the thrombin calibrator in the CAT assay, since free thrombin in human plasma rapidly decays. The easiest way to determine a is to take the first derivative of the experimentally measured thrombin calibrator curve, pass a trend-line through the values, and alter α until the trend-line is horizontal. The intercept of this horizontal trend-line with the ordinate is a value called the ideal calibrator reaction velocity. Note that the first derivative of these ideal calibrator curves was computed using the numerical approximation given as Equation 5 (or the first-order divided difference formula).

$$f'(t) = \underline{f(t_2) - f(t_1)}/(t2-t1) \tag{5}$$

In Equation 5, $f$ represents the ideal fluorescence signal intensity and $t_1$ and $t_2$ represent two adjacent measurement time-points.

The ideal calibrator reaction velocity for the undiluted thrombin calibrator was used to compute the calibration factor, or the factor that transforms any ideal fluorescence signal to a total ideal thrombin concentration integral. This single calibration factor was then used to transform the diluted and undiluted ideal calibrator intensities to total ideal thrombin concentration integrals. Each total ideal thrombin integral was differentiated using Equation 5, yielding the associated steady-state thrombin generation time-course for each calibrator. Note that since Equation 5 is first-order, the derivative it yields is much nosier than the original signal. Therefore a trend-line was passed through each steady-state thrombin generation time-course, the intercept of which represents the calculated steady-state thrombin concentration for each calibrator. These steady-state thrombin generation time-courses are important since they can be used to gauge the accuracy of the CAT data analysis methods, given that the true thrombin concentration of each calibrator, whether diluted or not, is known a priori. As such, the purpose of diluting the purchased thrombin calibrator in this CAT assay was to enable a comparison between the known and computed thrombin calibrator concentrations. This comparison was done by plotting the known and calculated thrombin calibrator concentrations and seeing if a significant difference between the two existed. This comparison plot is shown as FIG. 36.

Figure 36:
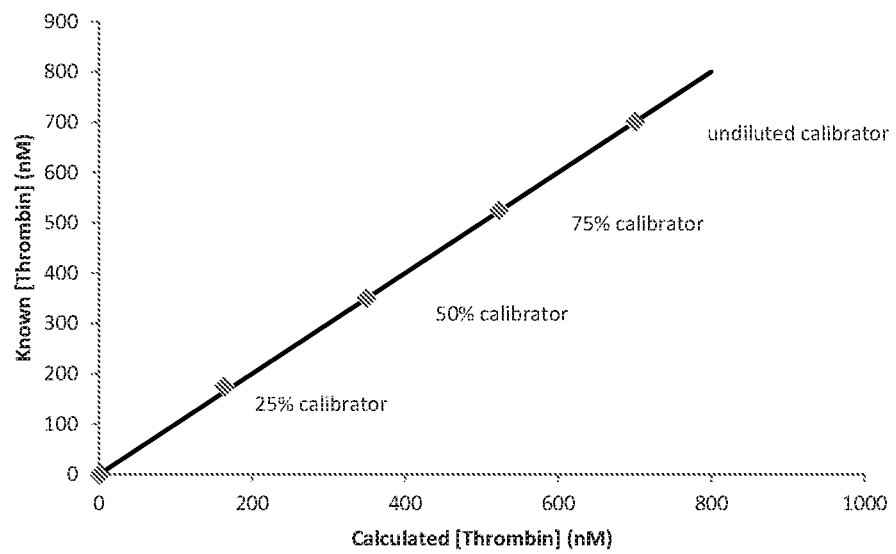
FIG. 36: Comparison plot between the known and computed thrombin calibrator concentrations used in the CAT assay. The thrombin calibrator concentrations were computed via the data analysis method outlined by Hemker and Kremers.

If the known and calculated thrombin calibrator concentrations were identical they would lie on the black line shown in FIG. 36. As such, the agreement between the two is very strong, indicating that both the CAT assay protocol and analysis methods are sound.

To compute the thrombin generation time-courses for the unknown samples, the corresponding experimentally measured fluorescence intensities are first converted to their ideal values using the H-Transform (Equation 4, with α determined from the average undiluted thrombin calibrator curve). Next the calibration factor was used to convert these ideal fluorescence signals to total ideal thrombin concentration integrals. From these total thrombin integrals, the fluorescent signal corresponding to free thrombin alone was mathematically dissected from it using the algorithm outlined by Hemker and Beguin in 1995; this was done to account for the alpha2M effect. This algorithm was programmed as a METLAB® executable and the corresponding output total ideal free thrombin concentration integrals were inserted into Microsoft Excel. At this point in the data analysis a smooth curve was fitted through each total ideal free thrombin concentration integral; the generic form of this equation is given as Equation 6.

$$T = \varepsilon \times n \times \exp(-(t-\tau)(k_{dec}))) \tag{6}$$

In Equation 6, T is the total ideal free thrombin concentration, ε is the ETP, τ is the time to peak thrombin concentration, n is the peak thrombin concentration, π is the number of measuring points per minute, and $k_{dec}$ is the decay constant of thrombin; it can be calculated from the relation $k_{dec} = 2.72\ \pi/\varepsilon$, where the constant 2.72 is the basis of the natural logarithm Once the total ideal free thrombin integrals are properly fitted to Equation 6, the associated free thrombin generation time-courses for the unknown samples are found analytically by differentiating Equation 6 with respect to time, yielding Equation 7.

$$[\text{Thrombin}] = k_{dec} \times n \times \varepsilon \times \exp(k_{dec}(\tau t-t) - \exp(k_{dec}(\tau t-t))) \tag{7}$$

Figure 37:
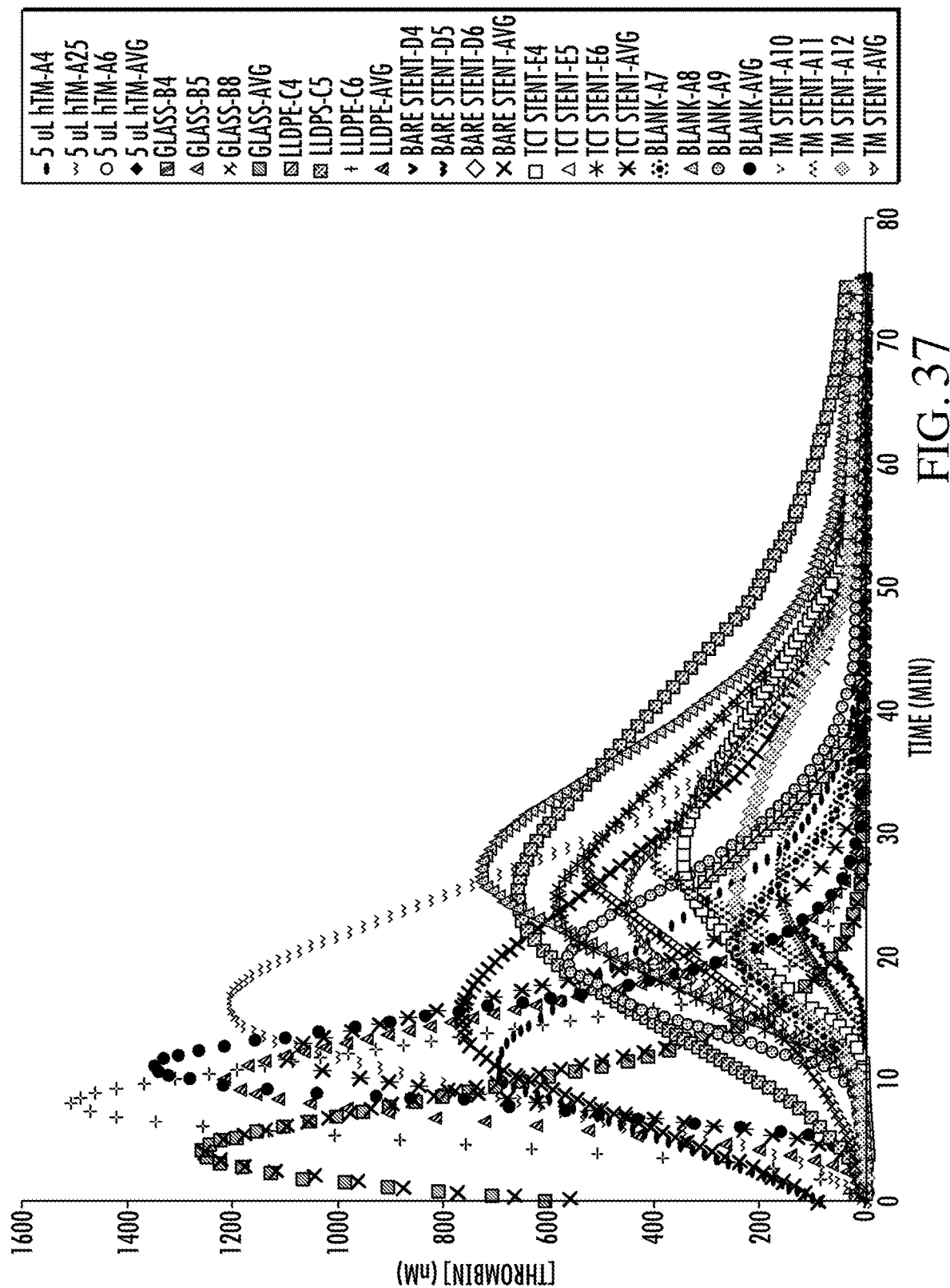
FIG. 37: Free thrombin generation time-courses (or thrombograms) associated with the unknown samples run in the in-house CAT assay. The alphanumeric well numbers associated with each sample are given in the plot legend; avg indicates that the curve is the average of the measured triplicate wells.

The free thrombin generation time-courses, or thrombograms, for the unknown samples run in this in-house CAT assay are shown as FIG. 37.

As evidenced in FIG. 37, several single value metrics exist to describe a given thrombogram. One such metric of overall thrombogenicity is peak thrombin concentration. This metric is shown in FIG. 38 for all the samples run in the in-house CAT assay.

Figure 38:
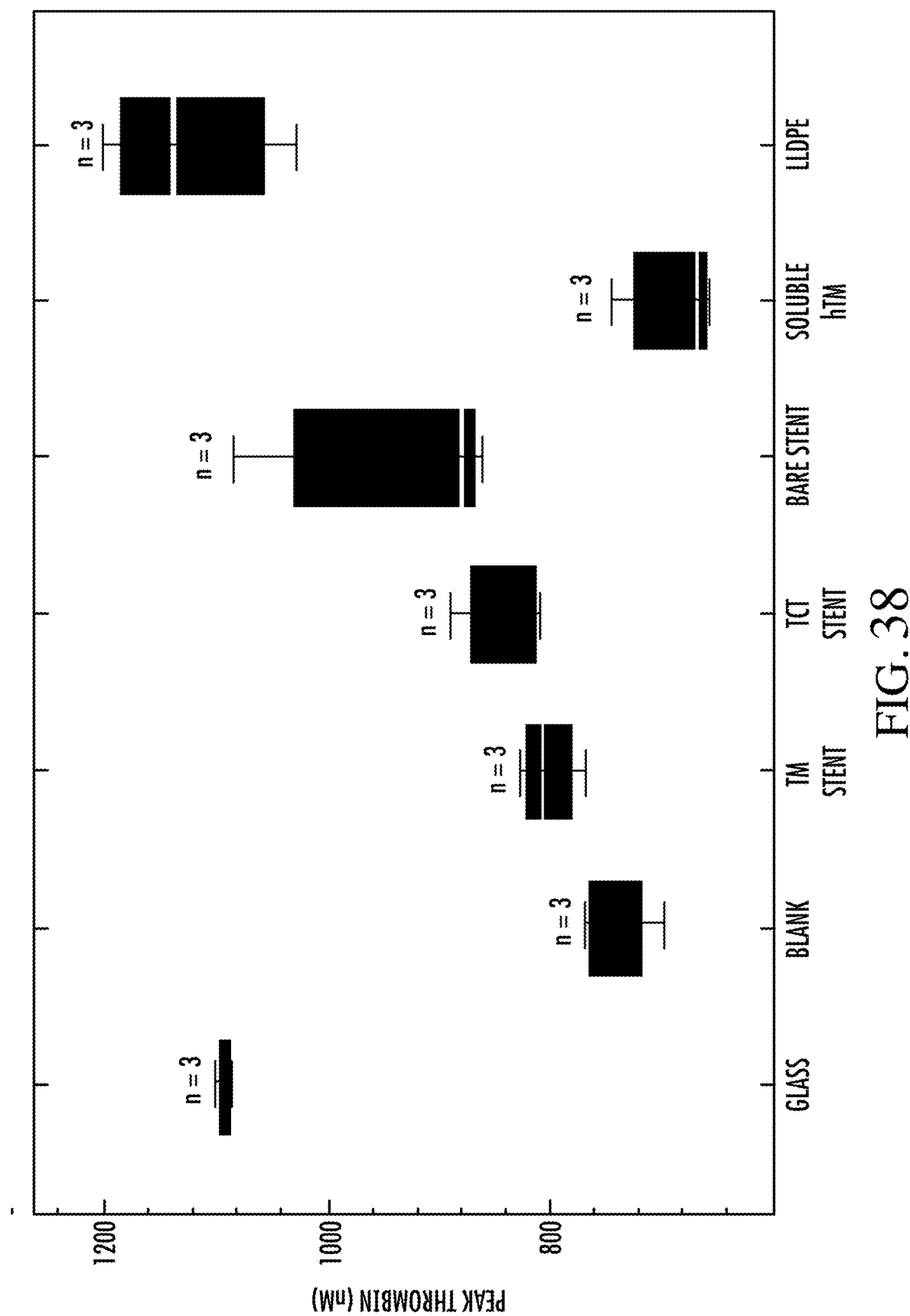
FIG. 38: The peak thrombin concentration associated with the thrombogram of each sample run in an in-house CAT assay.

In FIG. 38 both the TM and TCT stents generated less thrombin, and therefore exhibited less thrombogenicity, than the bare devices, as well as the positive controls glass and LLDPE. The blank and the soluble hTM, the two negative controls, generated less thrombin than both the TM and TCT stents. This thrombogram indicates that the bioactive function of the bound hTM in the inventive coating reduces device thrombogenicity to a greater extent than that of the combined aluminum oxide, silane, and TCT layers.

In addition to the in-house thrombogram testing done at the UI, in-vitro thrombogenicity testing was also done by a commercial vendor. The testing protocol used by this company was not made available: nevertheless it is generally known that the test used was a fluorogenic assay measuring thrombin generation in human plasma, so it is expected that the actual testing protocol is similar to the CAT assay method previously described. For the initial in-vitro assay done by the commercial vendor, one Pipeline® flow diverting device coated with the inventive technology (i.e. a TM stent) was shipped to the company on ice. The test results, in terms of peak thrombin generation, are shown in FIG. 39.

Figure 39:
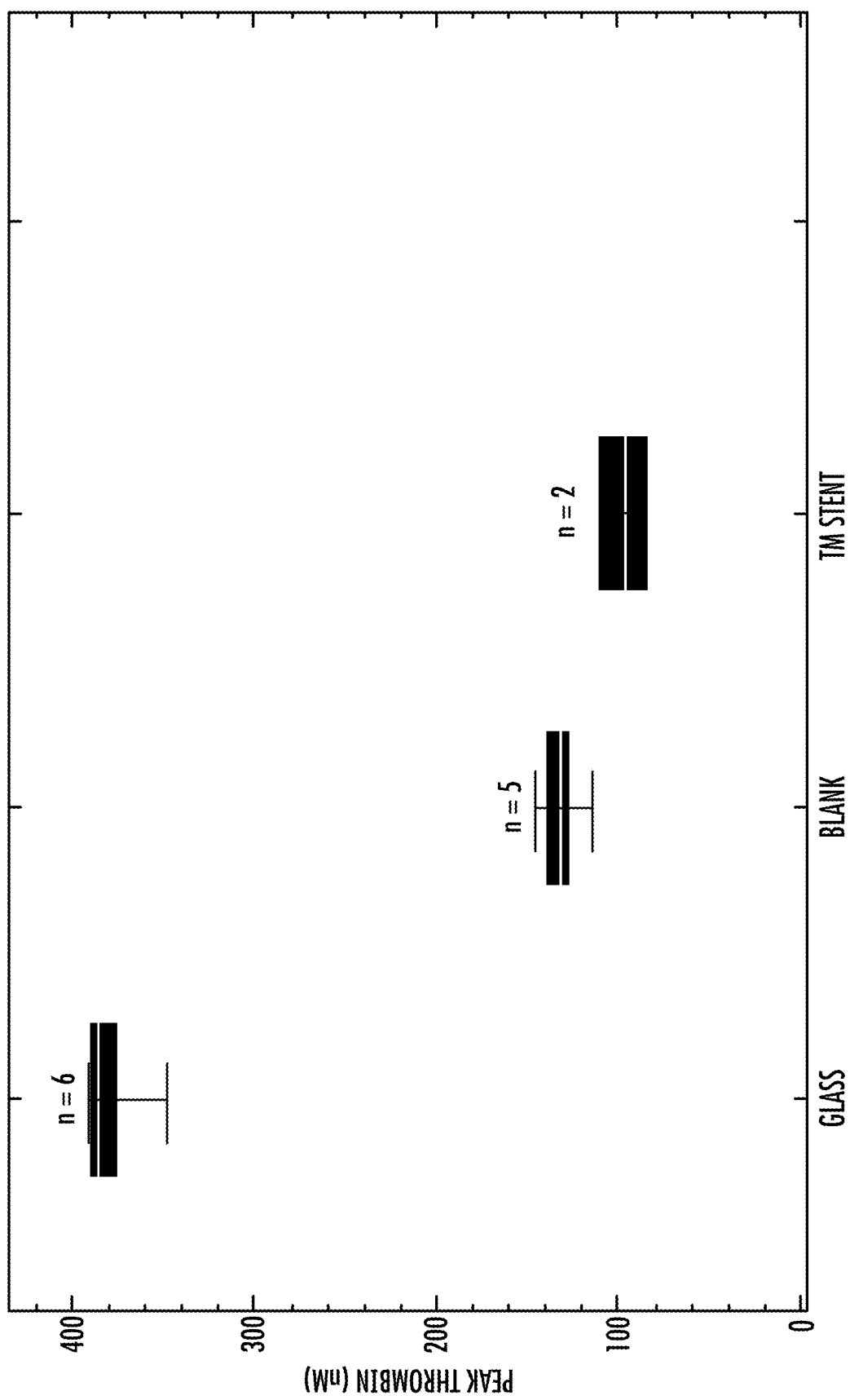
FIG. 39: The peak thrombin concentration associated with the thrombogram of each sample tested. The coated samples in this test were shipped to the analyst on ice.
Figure 40:
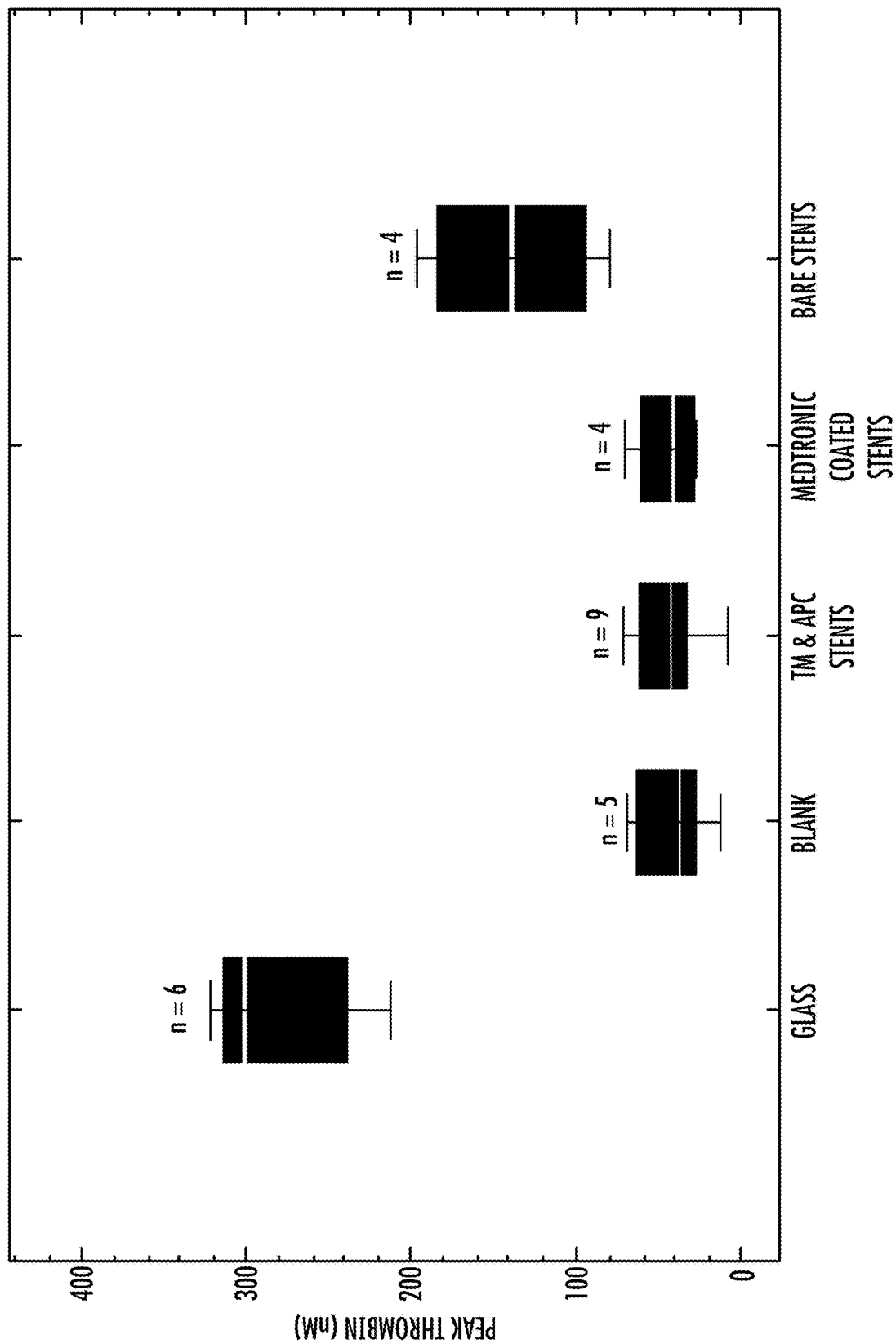
FIG. 40: The peak thrombin concentration associated with the thrombogram of each sample tested. The coated samples in this test were shipped to the analyst at room temperature.

Like the in-house thrombogram results shown in FIG. 38, FIG. 39 indicates that the TM stent is comparable to the blank wells. Next six coated Pipeline® devices were sent to the commercial vendor; three were TM stents, while the remaining three were coated with both TM and APC (incubation solution consisted of 10 µg TM+0.25 mg APC in 500 µL PBS). These coated devices were then shipped to the commercial vendor at room temperature. The peak thrombin generation test results are shown in FIG. 40. Note that the commercial vendor lumped the coated devices sent to them together in a single analysis. The commercial vendor also tested against their own coating technology (called the Shield, currently in research and development) and bare Pipeline® devices.

FIG. 40 indicates that the inventive coating technology, regardless of being incubated with TM alone or a combination of TM and APC, has thrombogenicity comparable to the blank wells. In addition, the inventive coating technology is comparable to the commercial vendor's Shield technology, and is less thrombotic than glass and bare metal devices. These results are in keeping with the in-vitro results previously discussed. The final in-vitro thrombogenicity test done by the commercial vendor was on 3 Pipeline® devices coated with all the inventive coating layers except hTM (i.e. TCT stents). These TCT stents were sent to the commercial vendor at room temperature. The test results are shown as FIG. 41.

Figure 41:
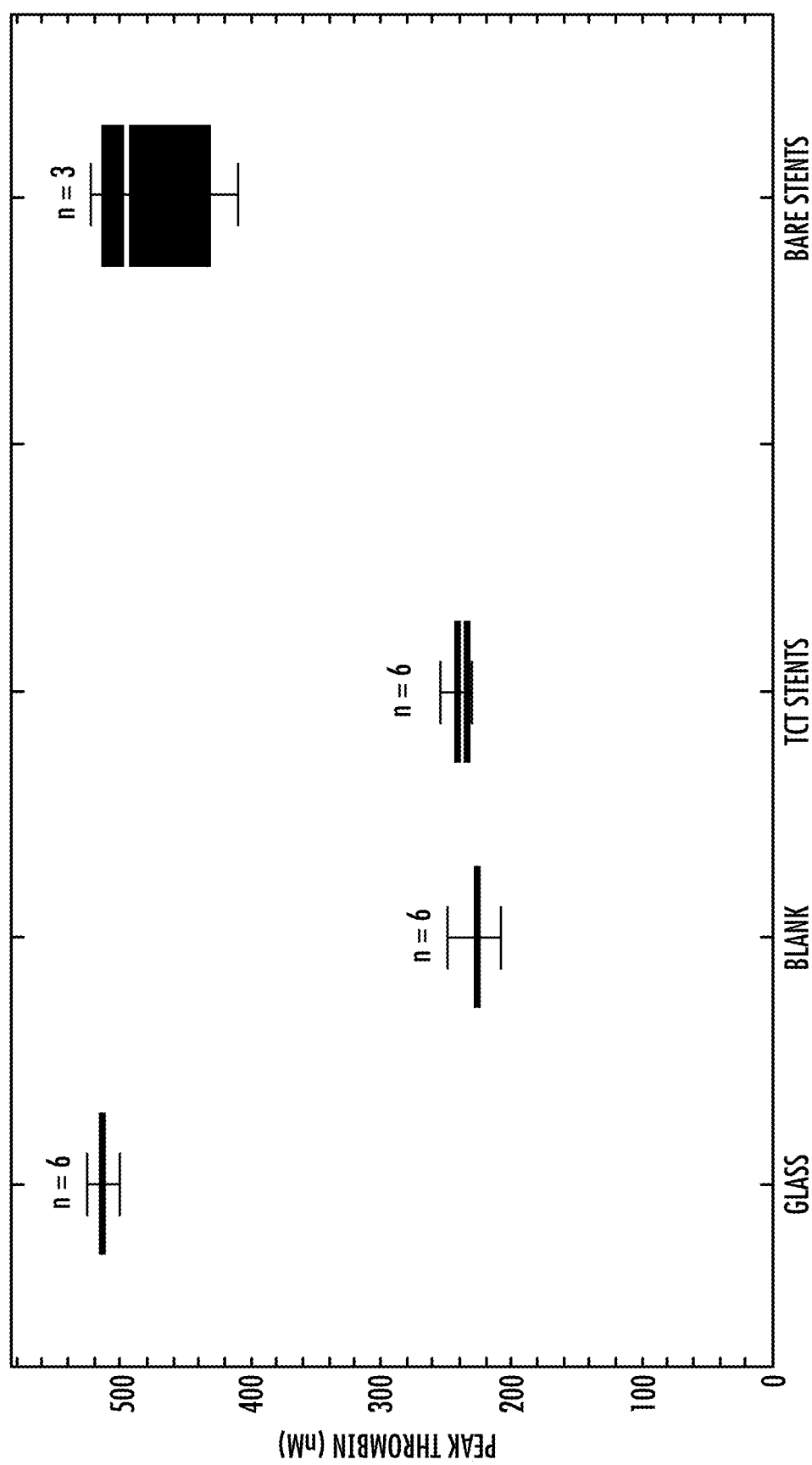
FIG. 41: The peak thrombin concentration associated with the thrombogram of each sample tested. The coated samples in this test were shipped to the analyst at room temperature.

FIG. 41 indicates that the TCT stents have thrombogenicity comparable to the blank wells, the implication of which is that the TCT stents have a thrombotic response comparable to those coated with the bioactive hTM protein.

The Protein C Activation In-Vitro Assay: The bioactivity of the immobilized hTM in the inventive coating technology was assessed in-vitro via the Protein C Activation Assay. This assay measures hTM functionality indirectly, specifically by measuring the change in optical density produced by a chromogenic substrate specific to APC in buffered solution. Once the change in optical density is measured, it is compared to the optical density signals from standard amounts of soluble hTM. From this comparison the amount of functional hTM bound to a device can be computed.

The Lentz Lab protocol for the Protein C Activation Assay was used for this test. The functionality of hTM bound via the inventive coating deposition protocol to two Enterprise® stent-assisted coiling devices (manufactured by Codman Neurovascular) was assessed, as compared to a bare Enterprise® device. First the samples containing the unknown amount of hTM were prepared (in this case the two TM stents) in cell lysate extract (20 mM Tris-HCl pH 8.0, 100 mN NaCl, 3 mM $CaCl_2$, 0.6% triton X-100) in microfuge tubes. The TM stents were not cut, but rather partially submerged in the lysate solution. The bare metal stent was also partially submerged in the cell lysate extract in another microfuge tube. Next 5 uL of the soluble hTM standards (0, 2.5, 5.0, 10.0, and 20 nM) were added in triplicates into separate microfuge tubes. Also 5 µL of cell lysate extract (200 µg/ml) was added to separate microfuge tubes, again in triplicate. Following this, the pre-mix to add to each tube was made (consisting of assay buffer, 325 nM human alpha-thrombin, and 1.5 µM protein C) and 20 µL was added to each microfuge tube. The assay buffer consisted of DI water, tris-HCl with pH=7.4, $CaCl_2$, NaCl, and Bovine Serum Albumin (BSA). All the samples were mixed, centrifuged at 1000 rpm, and incubated in a water bath at 37° C. for 30 minutes. After incubation, 2 µL of stop solution (consisting of assay buffer, anti-thrombin HL and heparin) was added to each sample, vortexed, and spun down. The samples were then assayed immediately. To start, the chromogenic substrate S-2366 was brought to room temperature. Following this, 5 µL of each sample or control was added to individual wells of a 96-well microplate. With a multi-pipettor, 100 uL of S-2366 was then added to each well. The 96-well plate was then placed in a microplate reader with absorbance set at 405 nm for five minutes. Only the absorbance rates for the three devices and the TM standards were recorded, and the absorbance rates were used to create the absorbance vs. time raw data for the control and TM-coated devices and is as shown in FIG. 42.

The TM standard curve was then generated by plotting the absorbance rates of each TM standard against their respective TM concentrations; a linear trend-line was passed through this and its equation was used to linearly interpolate the measured absorbance rates of the bare and TM-coated devices onto the standard curve. In this way the amount of active hTM bound to the coated devices was determined. This standard curve is shown as FIG. 43.

Figure 42:
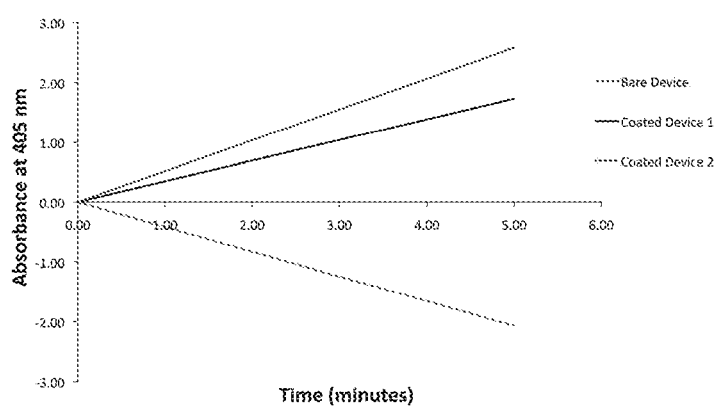
FIG. 42: The derived absorbance vs. time raw data for the bare and coated Enterprise® devices tested in the activated protein C assay. The raw data was generated using the recorded absorbance rates over the measurement time period.
Figure 43:
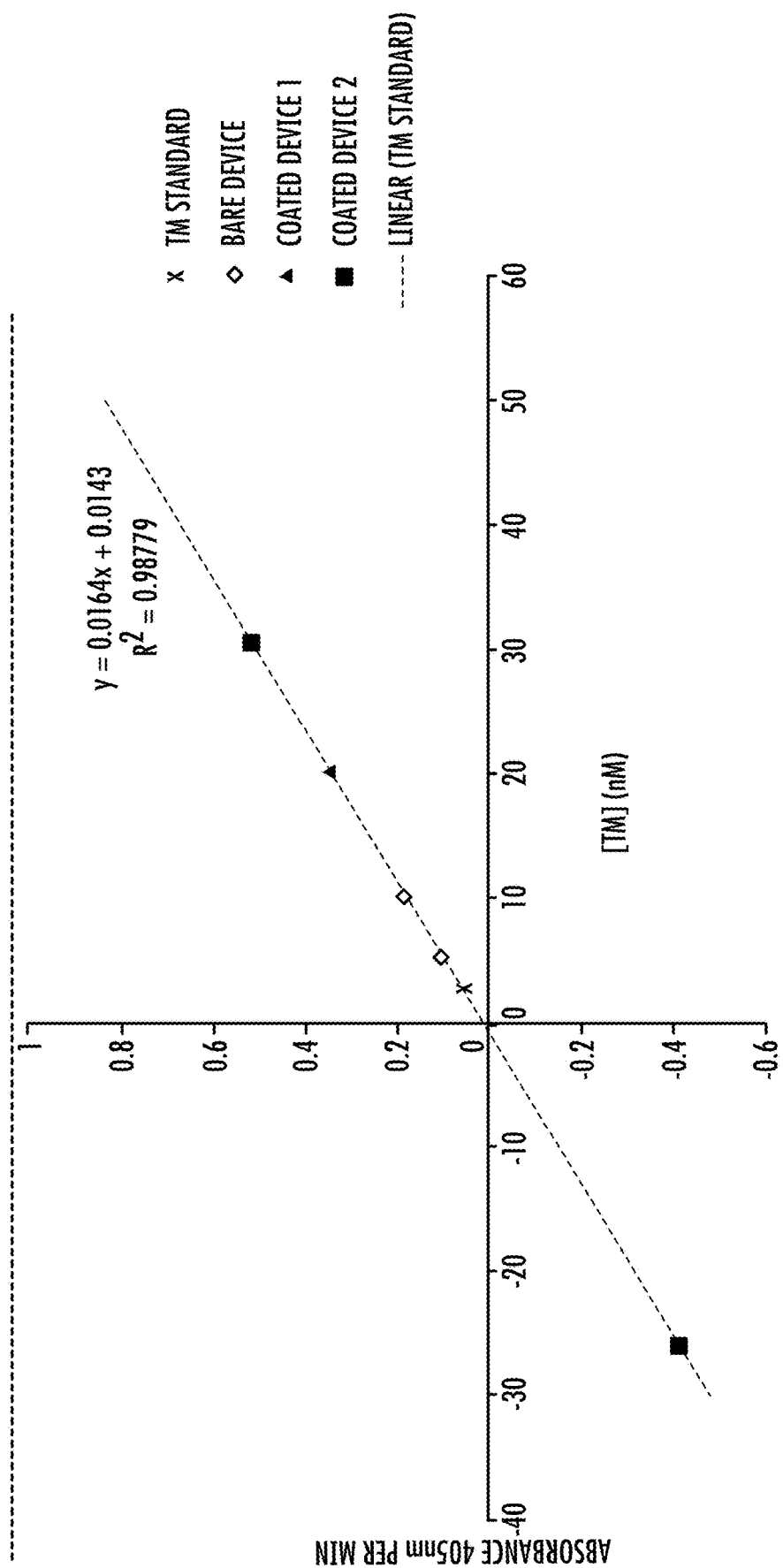
FIG. 43: The TM standard curve associate with the activated protein C assay. The measured absorbance rates for the bare and TM-coated Enterprise® devices are linearly interpolated on this curve to determine the amount of active hTM bound to the coated devices.

The negative absorbance rate associated with the bare Enterprise® device, shown in FIGS. 42 and 43, was a surprising result. While the precise mechanism is unknown, it is believed that metal ions, characteristic of both the bare metal stent and the mouse heart tissue, act to attenuate the function of the chromogenic substrate S-2366 and therefore produce negative absorbance over time. Additionally differences in the absorbance rates were found to exist between the two TM-coated devices, as shown in FIG. 42. A potential explanation for this difference is that the devices were submerged to a different extent in the buffer solution, causing different amounts of protein C activation and ultimately absorbance rates. Since this was the first time the assay had been done with solid devices, the degree of device submersion in the buffer was not considered initially to be a source of error. Nevertheless, from the linearly interpolated TM concentrations of the TM-coated devices onto the standard curve (FIG. 43) it is estimated that between 20.2-30.5 nM of the bound hTM is functional and that this hTM is bound to approximately 5 mm of the device, which is an estimate of the average device submersion in the buffer solution.

In-Vivo Porcine Model—A Survival Study: A porcine model was chosen to test the thrombogenicity of the inventive coating technology in-vivo. Nevertheless, this in-vivo test was done at the UI, and was a preliminary study to assess survival of pigs with implanted TM-coated stents only. The study design consisted of bilaterally-inserting 10 TM-coated stems into the common carotids of five mini Yucatan pigs. The pigs were of mixed sex and weighed between 44-88 pounds each. The coated devices used were LVIS™ stent-assisted coiling devices manufactured by MicroVention; these devices were coated following the inventive coating deposition protocol, were shipped to MicroVention to be inserted back into deployment catheters and sterilized via Micro Vention' s standard electron beam sterilization technique, and then shipped back to the UI for deployment in the pigs. The general care, anesthesia, operating room (OR), and euthanasia protocols for the animals used in this study were in compliance with the Institutional Animal Care and Use Committee (IACUC). Briefly, one TM-coated LVIS™ device was inserted into each common carotid artery of a pig under general anesthesia (i.e. two devices per pig were implanted). Device deployment and subsequent vascular wall apposition was checked with digital fluoroscopic x-ray during surgery. After surgery a neurovascular check was performed on each pig every six hours for five days; this was done to check for signs of neurological deficit. On the fifth day the animals were again put under general anesthesia and subjected to both MRI and time-of-flight MRA head and neck scans. Each animal was then brought to the OR where the animal was euthanized and the carotid arteries were subsequently excised for gross inspection.

The primary finding of this preliminary in-vivo survival study was that all animals were alive at five days post device implantation surgery and none exhibited neurological deficits on exam, meaning all animals survived and were in good health at the study endpoint. One pig developed a groin hematoma, a complication associated with the surgical access site, and developed a limp; however, the appropriate pain-relieving therapy for this complication was administered by a veterinarian. The MRI head and neck scans indicated no brain lesions or strokes in any of the animals; likewise, the time-of-flight MRI head and neck scans indicated good blood flow distal to the implantation site in each animal. The gross inspection of the implanted devices indicated that eight stents were patent, while two stents exhibited major thrombosis thought to be caused by crimping of the stem ends. Due to the age of the digital fluoroscopic x-ray used during surgery to position and deploy each device, it is unknown whether the device crimping occurred during deployment or during the excision procedure.

It should be mentioned that a limitation to this study is lack of a good animal model for acute stroke. In pigs and sheep, lack of a true capillary bed between the pharyngeal artery and internal carotid blocks full access to the internal carotid and therefore does not allow a clot to be delivered to the substance of the brain. Excessive collateral circulation in dogs compromise their use as stroke models and smaller animals have blood vessels that are much smaller than the average adult human, limiting their use. Nevertheless, the merit of the porcine model is that it roughly duplicates the vascular dimensions of an adult human, which is why this model was chosen for the UI survival study.

Ex-Vivo Primate Shunt Model: To assess the extent of platelet and fibrin accumulation in-vivo, an established baboon model of arterial-type thrombosis was chosen. Nevertheless, in this model vascular thrombosis is induced in a permanent arterio-venous shunt in trained and conscious baboons. This model has been used extensively to quantify the haemocompatibility of biomaterials, including stents, as well as the antithrombotic efficacy of both established and novel antithrombotic drugs. Specifically a baboon is a good thrombosis model because of its hemostatic similarity to humans, its large size, the logistical ease of acquiring frequent blood samples from it, and the animals' general acceptance of chronically patent arterio-venous cannulas.

All primate experimentation was performed at the Oregon National Primate Research Center (ONPRC) in Beaverton, Oreg. under the umbrella of an IACUC-approved protocol. Specifically two male primates, between the ages of 3-5 years old, were used in this study and all treatments and controls were tested in the same animal to limit variability. Additionally the FRED™ flow diverting device, manufactured by MicroVention, was used in this study; these devices were coated following the inventive coating deposition protocol, were shipped to MicroVention to be inserted back into deployment catheters and sterilized via MicroVention's standard electron beam sterilization technique, and then shipped to the ONPRC for deployment in the primates.

Figure 44:
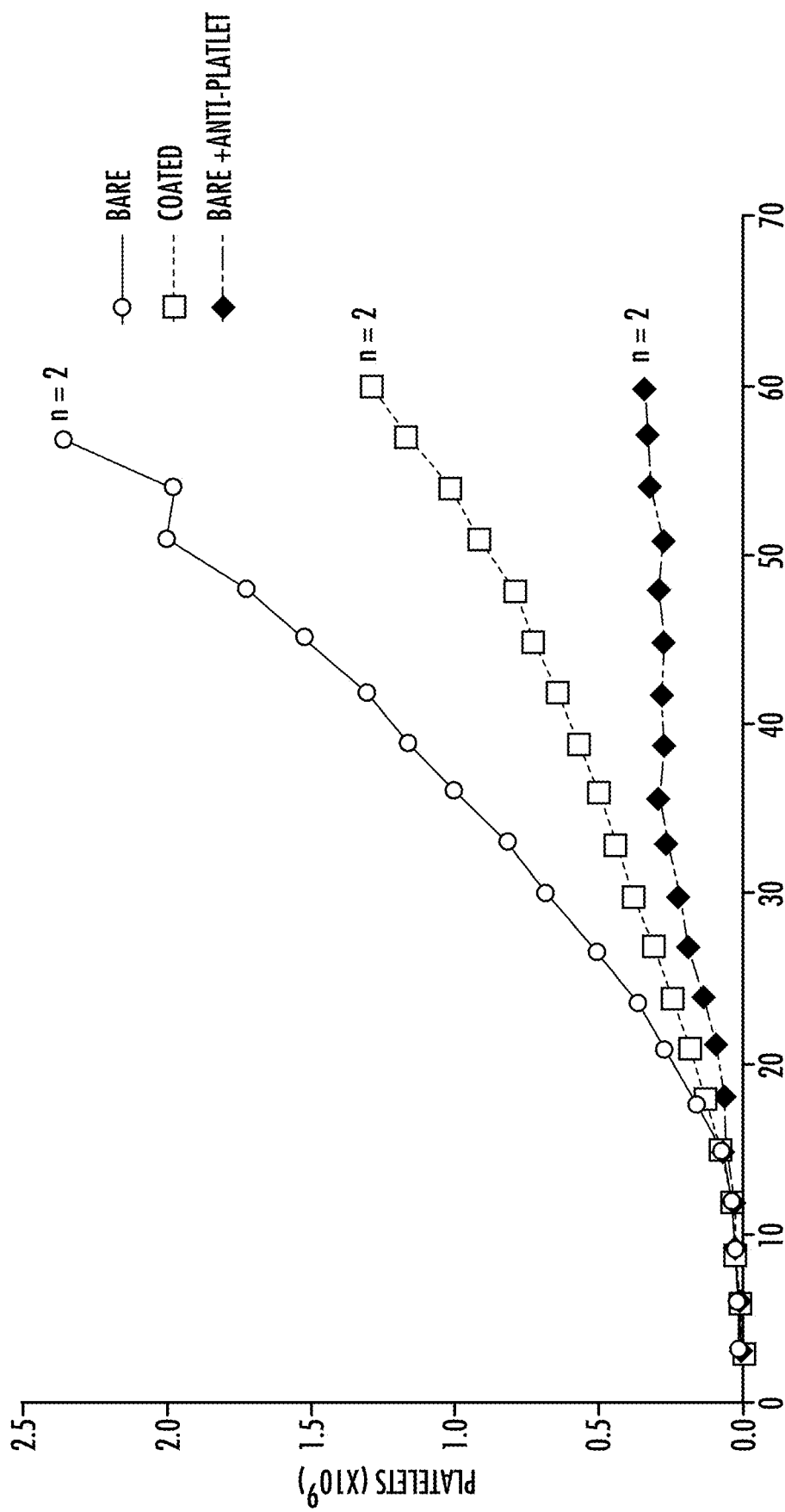
FIG. 44: The platelet deposition on bare FRED™ devices (bare), TM-coated FREDs™ (coated), and bare FREDs™ deployed in combination with dual anti-platelets (bare+: anti-platelet) in an ex-vivo primate shunt model.

The study design consisted of comparing the extent of platelet and fibrin accumulation in the following devices deployed in the arterio-venous shunt of the same primate; a bare device, a TM-coated device, and a bare device deployed in combination with dual systemic anti-platelet therapy. To measure platelet deposition in the deployed devices, mean blood flow rate through the shunt was first continuously measured by a Doppler Ultrasonic Flow Meter and held constant by an external screw clamp. Autologous platelets were radiolabeled one day prior with Indium-111 oxine and re-injected into the baboon on the day of testing. Platelet deposition was then measured over a one hour perfusion period using a high sensitivity 99Tc collimator and scintillation camera (GE 400T, General Electric). Imaging of the 172 keV $^{111}$ photon peaks was done at three-minute intervals (approximately) and recorded. The extent of platelet deposition on a bare FRED™ device, a TM-coated device, and a bare device deployed in combination with dual systemic antiplatelet therapy in the primate shunt is shown as FIG. 44.

Figure 45:
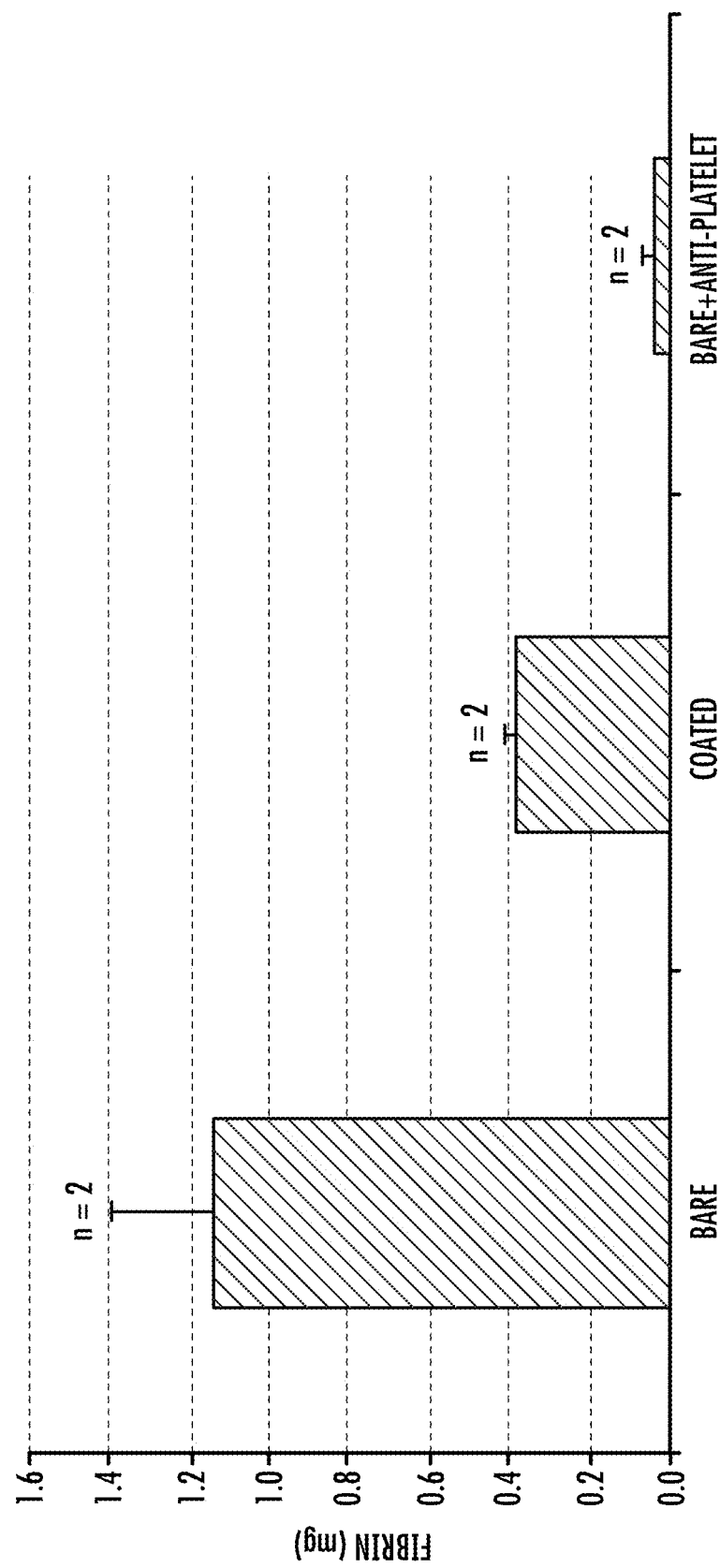
FIG. 45: The fibrin deposition on bare FRED™ devices (bare), TM-coated FREDs™ (coated), and bare FREDs™ deployed in combination with dual anti-platelets (bare+anti-platelet) exposed to blood for one hour in an ex-vivo primate shunt model. This experiment was run at the Oregon National Primate Research Center.
Figure 46:
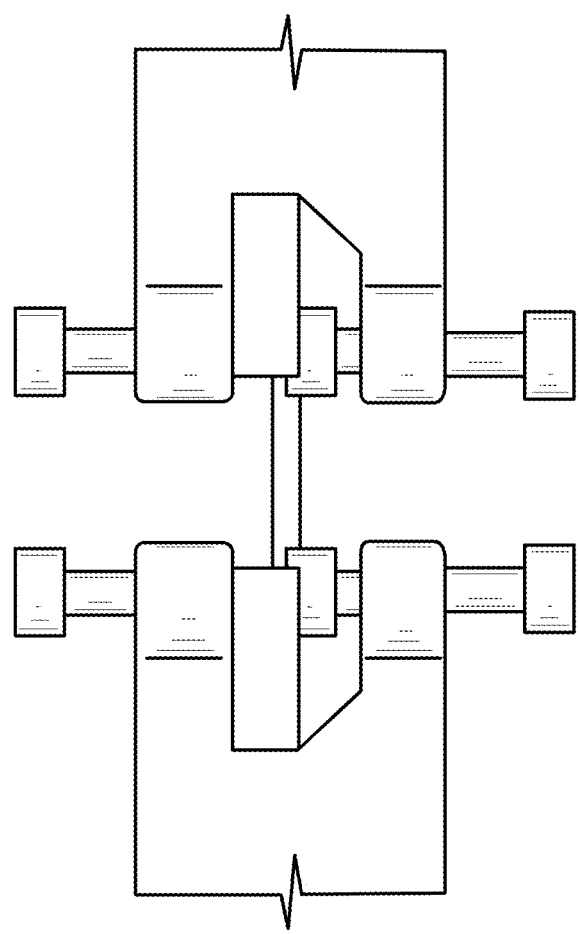
FIG. 46: A Pipeline® flow diverting device clamped in the MTS uniaxial extension tester.

Following the 60-minute exposure to blood, the deployed stent was removed from the shunt. The amount of fibrin deposition was measured by first perfusing the removed stents in a glutaraldehyde-PBS solution. The stents were subsequently dehydrated in increasing concentrations of ethanol, critical point dried, and weighed. The stent weight was then compared to the weight prior to deployment in the shunt to determine the amount of fibrin accumulation over time. The fibrin deposition on a bare FRED™ device, a TM-coated device, and a bare device deployed in combination with dual systemic anti-platelet therapy after the hour-long exposure to blood flow in the primate shunt is shown as FIG. 45.

The primary finding of this primate study is that the inventive coating technology accumulates fewer platelets and has decreased fibrin deposition when compared to a bare metal device, but still accumulates more platelets and fibrin over time than the bare device and systemic administration of dual anti-platelet drugs, the current standard of care. However a device coated with the inventive technology used in conjunction with systemic dual antiplatelet therapy would have less thrombogenicity than the current standard of care using bare metal stents.

Assessing the Effect of the Coating on Device Mechanics.

Methodology for Determining Device Stiffness—Uniaxial Extension: One way to assess the stiffness of a neurovascular stent or flow diverting device is to stretch the device along one axis (i.e. uniaxial extension) and measure the force required to hold the stretch. Stiff devices will require more force to stretch, while flexible devices will stretch easily when small forces are applied to them. Such uniaxial tensile testing can be done to assess stiffness of both neurovascular stents and flow diverting devices; however for flow diverting devices the respective change in device diameter in response to a uniaxial force is another metric of physical importance, since these devices are first stretched uniaxially and then loaded into their respective deployment microcatheters. It is therefore the capability of the flow diverting device to decrease in diameter when stretched that determines the ease in which the device can be placed its microcatheter. This means that the stiffness of flow diverting devices can be determined by measuring the respective device diameter change in response to a uniaxially applied force. Additionally, the stiffness of neurovascular stent and flow diverting devices is important because the cerebral blood vessels can be highly tortuous and if said devices are too stiff they will not be able to conform to the tortuous vessel geometry, ultimately leading to adverse complications for the patient.

Given the importance of neurovascular device stiffness, a uniaxial tensile testing methodology was developed to assess neurovascular device stiffness. This method was developed specifically for flow diverting devices, since the test measures the respective device diameter change in response to a uniaxially applied force. The developed uniaxial tensile testing methodology uses a uniaxial extension tester (manufactured by MTS Systems Corporation, Eden Prairie, Minn.) to extend a flow diverting device at a fixed rate and measure the corresponding extension force. In this methodology a digital camera is used to film the tensile test; subsequently an image processing software called ImageJ is used to measure the diameter of the device from the film. To assess the repeatability of the developed testing methodology, a single Pipeline® flow diverting device was extended 12 times in the uniaxial extension tester and the force-device diameter data was measured following the testing methodology. A photo of the device clamped into the uniaxial extension tester prior to extension is shown as FIG. 49.

Initially testing was done with this single flow diverting device to assess the repeatability of deformation. To do this the device was stretched by approximately 170% (from an initial compressed position) in the uniaxial tester and the corresponding force-device diameter data was measured following the testing methodology (n=3). Next to assess whether the device placement in the clamps affected the force or diameter measurements, the device was taken out of the clamps, re-positioned in them then extended by 170% from the same initially compressed position (n=3).

In order to make the developed testing methodology easier to execute given a broad range of How diverting device sizes, the same Pipeline® device was again extended in the extension tester, but this time the extension was done from an initial position whereby the measured force was zero (i.e. a zero position). From this zero position the device was compressed by 7% and then extended by approximately 134% (n=3). Again these tests were filmed with a digital camera and the corresponding device diameter was measured via lmageJ. To assess whether the device placement in the clamps affected the force or diameter measurements, the device was taken out of the clamps, re-positioned in them, and then extended by 134% from the zero position (n=3) The force-device diameter data measured from these six tests, as well as the six tests performed from the initially compressed position, is shown as FIG. 50.

Figure 47:
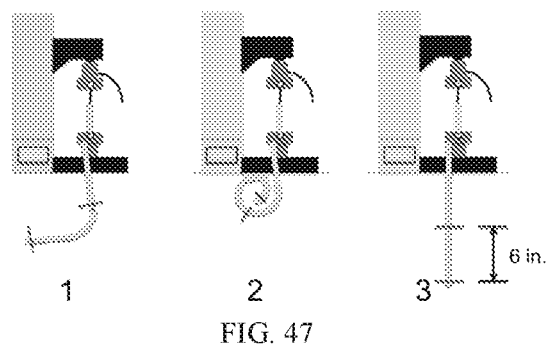
FIG. 47: The configuration of the microcatheters used in assessing the MTS extension tester load cell sensitivity. Configuration 1 allows for the device to be pulled through a single bend in the catheter. Configuration 2 allows for the device to be pulled through a highly tortuous catheter. Configuration 3 allows for the device to be pulled through a straight catheter. The device is pulled a total of six inches in all configurations.

Methodology for Computing Device-Associated Friction in Microcatheter:

The friction associated with pushing a neurovascular stentor flow diverting device through its microcatheter is an important clinical metric since it influences a neuroradiologist's decision regarding what brand of device to use in his or her clinic. Devices that are easier to push through their microcatheters, or are more pushable, are more attractive to neuroradiologists. In addition to clinical importance, Medtronic has also verbally indicated that their Shield coating technology, currently in research and development, offers increased pushability through the microcatheter as compared with bare devices. Therefore, because device pushability is clinically importance and is a metric neurovascular stent and flow-diverter manufacturers use to market their devices, we developed a methodology for assessing neurovascular device-associated friction. The developed friction testing methodology uses a uniaxial extension tester (manufactured by MTS Systems Corporation, Eden Prairie, Minn.) to pull a flow diverting device at a fixed rate through its microcather. The MTS extension tester measures the force required to pull the device through the microcatheter; this extension force is equal in magnitude but opposite in direction to the device-associated frictional force. Specifically in this testing methodology both the device guidewire and deployment microcatheter are clamped into the uniaxial extension tester. The damp holding the catheter is kept fixed while the damp holding the guidewire is allowed to move at a fixed extension rate, effectively pulling the device through catheter; the load cell within the uniaxial extension tester measures the associated pulling force. To assess the sensitivity of the extension tester load cell to measure small changes in device friction, a single FRED™ flow diverting device was pulled by the uniaxial extension tester through six inches of its microcatheter oriented in three different configurations shown in FIG. 47; the idea being that device-associated friction should increase when pulled through a highly tortuous catheter configuration, and the load cell used in testing should capture this increase.

I claim:

1. A coated medical device, comprising:
at least one metal surface, at least a portion of which is coated with a metal oxide nanolayer;
at least a portion of the surface of the metal oxide nanolayer is coated with covalently bonded organosilane groups substituted with at least one reactive organic substituent;
and a polyfunctional linker attached to the at least one reactive organic substituent;
an active pharmaceutical agent bonded to or complexed with at least a portion of the polyfunctional linker;
the polyfunctional linker is a compound with two or more reactive groups that can react with the at least one reactive organic substituent and the optional active pharmaceutical agent;
the polyfunctional linker is 2, 4, 6-trichloro-1, 3, 5-triazine.

2. The coated medical device of claim 1, wherein the medical device is selected from the group consisting of an intra-cranial stent, a carotid stent, a cardiac stent, a peripheral vascular stent, a vascular graft, a cardiac valve, and an intra-vascular device.

3. The coated medicals device of claim 1, wherein the at least one metal surface comprises a metal or alloy selected from the group consisting of biomedical grade titanium, iron, nickel, magnesium, cobalt, and chromium.

4. The coated medical device of claim 1, wherein at least 90% of the metal surface is coated with the metal oxide nanolayer.

5. The coated medical device of claim 1, wherein the metal oxide nanolayer comprises a metal oxide selected from the group consisting of silicon oxide, aluminum oxide, titanium oxide, hafnium oxide, zirconium oxide, zinc oxide, tin oxide, strontium oxide, ytterbium oxide, $Zn_{1-x}Sn_xO_y$, ZTO, $SrTiO_3$, $SrCO_3$), and combinations thereof.

6. The coated medical device of claim 1, wherein the metal oxide nanolayer has a thickness of less than about 30 nm.

7. The coated medical device of claim 1, wherein the organosilane groups have the general formula:

$$(X-R)_n Si-Y_{4-n} \text{ or}$$

$$Y_3 Si-R-Z-R-SiY_3$$

wherein n is an integer from 1-3,
each X is independently H, substituted or unsubstituted vinyl, halo, hydroxyl, substituted or unsubstituted amino, acryloxy, methacryloxy, -SH, or substituted or unsubstituted ureido, each R is independently alkyl aryl, or arylalkyl, Z is disulfide or tetrasulfide, and
Each Y is independently halo or alkoxy.

8. The coated medical device of claim 1, wherein the active pharmaceutical agent is selected from the group consisting of hepatocyte growth factor, anti-thrombotic agents, antiplatelet agent and combinations thereof.

9. The coated medical device of claim 1, wherein the surface tension of the organosilane coated surface ranges from about 0-30°.

* * * * *